(12) United States Patent
Fischer et al.

(10) Patent No.: US 8,618,065 B2
(45) Date of Patent: Dec. 31, 2013

(54) CYCLOSPORIN DERIVATIVES

(75) Inventors: Gunter Fischer, Halle (DE); Miroslav Malesevic, Halle (DE); Frank Erdmann, Halle (DE); Jan Kühling, Halle (DE); Michael Bukrinsky, Potomac, MD (US); Stephanie Constant, Herndon, VA (US)

(73) Assignee: Max-Planck-Gesellschaft zur Foerderung der Wissenschaften E.V., Munich (DE)

( * ) Notice: Subject to any disclaimer, the term of this patent is extended or adjusted under 35 U.S.C. 154(b) by 0 days.

(21) Appl. No.: 13/397,256

(22) Filed: Feb. 15, 2012

(65) Prior Publication Data

US 2012/0196749 A1    Aug. 2, 2012

Related U.S. Application Data

(63) Continuation of application No. PCT/EP2010/005053, filed on Aug. 17, 2010.

(30) Foreign Application Priority Data

Aug. 17, 2009   (DE) .......................... 10 2009 037 551

(51) Int. Cl.
*A61K 38/12*      (2006.01)
*A61P 19/02*      (2006.01)
*A61K 38/16*      (2006.01)

(52) U.S. Cl.
USPC ......... 514/20.5; 514/16.6; 514/21.1; 530/317

(58) Field of Classification Search
None
See application file for complete search history.

(56) References Cited

U.S. PATENT DOCUMENTS

| | | | |
|---|---|---|---|
| 4,672,044 | A | 6/1987 | Schreiber |
| 6,395,770 | B1 | 5/2002 | Broder et al. |
| 6,423,233 | B1 | 7/2002 | Keri et al. |
| 6,596,499 | B2 | 7/2003 | Jalink |
| 7,090,995 | B2 | 8/2006 | Cabantchik et al. |
| 2005/0048671 | A1 | 3/2005 | Methfessel et al. |

FOREIGN PATENT DOCUMENTS

| | | |
|---|---|---|
| DE | 198 59 910 A1 | 6/2000 |
| EP | 0 296 122 A2 | 12/1988 |
| EP | 0 649 022 A1 | 4/1995 |
| JP | AU-2006200519 * | 10/2006 |
| WO | WO 98/42734 A1 | 10/1998 |
| WO | WO 03/097706 A1 | 11/2003 |

OTHER PUBLICATIONS

English translation of international preliminary report on patentability dated Feb. 21, 2012 of international application PCT/EP 2010/005053 on which this application is based.

Mascarell, L. et al, "Cyclosporin A therapy differently affects immunological-relevant gene expression following immunization", Immunology Letters, 2002, pp. 137 to 143, 84, Elsevier Science B.V.
Guillen, C. et al, "Regulatory Effects of Cytokines and Cyclosporine A on Peripheral Blood Mononuclear Cells from Stable Multiple Sclerosis Patients", Immunopharmacology and Immunotoxicology, 1999, pp. 527 to 549, 21(3), Marcel Dekker, Inc.
Wilasrusmee, C. et al, "Angiocidal effect of Cyclosporin A: a new therapeutic approach for pathogenic angiogenesis", International Angiology, 2005, Abstract, vol. 24, Issue 4.
Von Haehling, S. et al, "Cachexia: a therapeutic approach beyond cytokine antagonism", International Journal of Cardiology, 2002, pp. 173 to 183, 85, Elsevier Science Ireland Ltd.
Yamada, A. et al, "Usefulness and Limitation of DiBAC4(3), a Voltage-Sensitive Fluorescent Dye, for the Measurement of Membrane Potentials Regulated by Recombinant Large Conductance Ca2+-Activated K+ Channels in HEK293 Cells", Jpn. J. Pharmacol., 2001, pp. 342 to 350, 86.
Berth-Jones, J., "The use of ciclosporin in psoriasis", Journal of Dermatological Treatment, 2005, pp. 258 to 277, 16, Taylor & Francis.
Hansen, J. M. et al, "Effects of nitric oxide blockade and cyclosporin A on cardiovascular and renal function in normal man", Journal of Hypertension, 1999, pp. 1707 to 1713, 17, Lippincott Williams & Wilkins.
Lederman, M.M. et al, "Cyclosporin A Provides No Sustained Immunologic Benefit to Person with Chronic HIV-1 Infection Starting Suppressive Antiretroviral Therapy: Results of a Randomized, Controlled Trial of the AIDS Clinical Trials Group A5138", The Journal of Infectious Diseases, 2006, pp. 1677 to 1685, 194.
Wulff, B.C. et al, "Sirolimus Reduces the Incidence and Progression of UVB-Induced Skin Cancer in SKH Mice even with Co-administration of Cyclosporine A", Journal of Investigative Dermatology, 2008, pp. 2467 to 2473, 128.
Zhao, G.J. et al, "Clinical and magnetic resonance imaging changes correlate in a clinical trial monitoring cyclosporine therapy for multiple sclerosis", Journal of Neuroimaging, 1997, Abstract, vol. 7, Issue 1.
Odaka, M. et al, "Intractable chronic inflammatory demyelinating polyneuropathy treated successfully with ciclosporin", J Neurol Neurosurg Psychiatry, 2005, pp. 1115 to 1120, 76.
Eberle, M. K. et al, "Synthesis of the Main Metabolite (OL-17) of Cyclosporin A", J. Org. Chem., 1992, pp. 2689 to 2691, 57, American Chemical Society.
Sukkar, T.Z. et al, Gingival fibroblasts grown from cyclosporin-treated patients show a reduced production of matrix metalloproteinase-1 (MMP-1) compared with normal gingival fibroblasts, and cyclosporin down-regulates the production of MMP-1 stimulated by pro-inflammatory cytokines, Journal of Periodontal Research, 2007, pp. 580 to 588, 42.
Kawai, R. et al, "Physiologically Based Pharmacokinetic Study on a Cyclosporin Derivative, SDZ IMM 125", Journal of Pharmacokinetics and Biopharmaceutics, 1994, pp. 327 to 365, vol. 22, No. 5, Plenum Publishing Corporation.

(Continued)

*Primary Examiner* — Satyanarayana R Gudibande
(74) *Attorney, Agent, or Firm* — Walter Ottesen P.A.

(57) ABSTRACT

A cyclosporin derivative of general Formula (I) or a pharmaceutically compatible salt thereof, which have a pharmaceutical effectiveness, for example in the case of chronic inflammatory diseases. The cyclosporin derivatives are preferably free from a peptide section capable of passing through the membrane of a biological cell.

8 Claims, 5 Drawing Sheets

(56) References Cited

OTHER PUBLICATIONS

Iwamura, H. et al, "Comparative Study of Glucocorticoids, Cyclosporine A, and JTE-607 [(-)-Ethyl-N-{3,5-dichloro-2-hydroxy-4-[2-(4-methylpiperazin-1-yl)ethoxy]benzoyl}-L-phenylalaninate Dihydrochloride] in a Mouse Septic Shock Model, The Journal of Pharmacology and Experimental Therapeutics, 2004, pp. 1256 to 1263, vol. 311, No. 3.

Noli, C. et al, "Prospective open pilot study on the use of ciclosporin for feline allergic skin disease", Journal of Small Animal Practice, 2006, pp. 434 to 438, vol. 47, Issue 8.

Kawasaki, H. et al, "Cyclosporine Inhibits Mouse Cytomegalovirus Infection via a Cyclophilin-Dependent Pathway Specifically in Neural Stem/Progenitor Cells", Journal of Virology, 2007, pp. 9013 to 9023, vol. 81, No. 17.

Pilarski, L.M. et al, "Drug resistance in multiple myeloma: cyclosporin A analogues and their metabolites as potential chemosensitizers", Leukemia, 1998, pp. 505 to 509, 12.

Wiernik, P. H. et al, "Objective Response of Multiple Myeloma to Cyclosporin A", Leukemia and Lymphoma, 1994, pp. 167 to 170, vol. 16, Harwood Academic Publishers GmbH.

International Search Report dated Jan. 20, 2011 of international application PCT/EP 2010/005053 on which this application is based.

Lexikon der Biochemie: in zwei Baenden/[Red. und Fachuebers. Angelika Fallert-Mueller], 1999, p. 505, Spektrum Akademischer Verlag.

DeLuca, D., "Chapter 7 Immunofluorescence Analysis", Antibody as a Tool, J.J. Marchalonis and G.W. Warr, eds., 1982, pp. 189 to 231, John Wiley & Sons Ltd.

Tsimberidou, A. et al, "Gemtuzumab, Fludarabine, Cytarabine, and Cyclosporine in Patients with Newly Diagnosed Acute Myelogenous Leukemia or High-Risk Myelodysplastic Syndromes", Cancer, 2003, pp. 1481 to 1487, 97, American Cancer Society.

Tsimberidou, A. M. et al, "Mylotarg, fludarabine, cytarabine (ara-C), and cyclosporine (MFAC) regimen as post-remission therapy in acute myelogenous leukemia", Cancer Chemother Pharmacol, 2003, pp. 449 to 452, 52, Springer-Verlag.

Barik, S., "Immunophilins: for the love of proteins", Cell. Mol. Life Sci., 2006, pp. 2889 to 2900, 63, Birkhaeuser Verlag, Basel.

Wang, F. et al, "Synthesis and Peptidyl-Prolyl Isomerase Inhibitory Activity of Quinoxalines as Ligands of Cyclophilin A", Chem. Pharm. Bull., 2006, pp. 372 to 376, 54(3), Pharmaceutical Society of Japan.

Uchida, T. et al, "Pin1 and Par14 Peptidyl Prolyl Isomerase Inhibitors Block Cell Proliferation", Chemistry & Biology, 2003, pp. 15 to 24, vol. 10, Elsevier Science Ltd.

Wang, Q.B. et al, "Injection of bradykinin or cyclosporine A to hippocampus induces Alzheimer-like phosphorylation of Tau and abnormal behavior in rats", Chinese Medical Journal, 2002, Abstract, vol. 115, Issue 6.

Damoiseaux, J.G.M.C. et al, "Multiple Effects of Cyclosporin A on the Thymus in Relation to T-Cell Development and Autoimmunity", Clinical Immunology and Immunopathology, 1997, pp. 197 to 202, vol. 82, No. 3, Academic Press.

Gurachevsky, A. et al, "Application of spin label electron paramagnetic resonance in the diagnosis and prognosis of cancer and sepsis", Clinical Chemistry and Laboratory Medicine, 2008, Abstract, vol. 46, Issue 9.

Fukushima, A. et al, "Cyclosporin A inhibits eosinophilic infiltration into the conjunctiva mediated by type IV allergic reactions", Clinical and Experimental Ophthalmology, 2006, pp. 347 to 353, 34, Royal Australian and New Zealand College of Ophthalmologists.

Jain, A.B. et al, "Cyclosporin and tacrolimus in clinical transplantation—A comparative review", Clinical Immunotherapeutics, 1996, Abstract, vol. 5, Issue 5.

Galat, A., "Peptidylprolyl Cis/Trans Isomerases (Immunophilins): Biological Diversity—Targets—Functions", Current Topics in Medicinal Chemistry, 2003, pp. 1315 to 1347, 3, Bentham Science Publishers Ltd.

Ravot, E. et al, "New Uses for Old Drugs in HIV Infection the Role of Hydroxyurea, Cyclosporin and Thalidomide", Drugs, 1999, pp. 953-963, 58(6), Adis International Limited.

Rao, M.R. et al, "Changes in the Cardiovascular Nitric Oxide Pathway in Cyclosporin-A Treated Rats", Drug and Chemical Toxicology, 1998, pp. 27 to 34, 21(1), Marcel Dekker, Inc.

Periyasamy, S. et al, "The Immunophilin Ligands Cyclosporin A and FK506 Suppress Prostate Cancer Cell Growth by Androgen Receptor-Dependent and -Independent Mechanisms", Endocrinology, 2007, pp. 4716 to 4726, 148(10), The Endocrine Society.

Tsuruoka, S. et al, "Dosing time-dependent variation of bone resorption by cyclosporin A in rats' femurs", European Journal of Pharmacology, 2007, pp. 226 to 231, 564, Elsevier B.V.

De Clercq, E., "Emerging antiviral drugs", Expert Opin. Emerging Drugs, 2008, pp. 393 to 416, 13(3), Informa UK Ltd.

Eckstein, J.W. et al, "A new class of cyclosporin analogues for the treatment of asthma", Expert Opin. Investig. Drugs, 2003, pp. 647 to 653, 12(4), Ashley Publications Ltd.

Binder, A. et al, "Bestimmung von Aciditaetskonstanten aus digitalen potentiometrischen Titrationskurven ohne Kenntnis der genauen Einwaage", Z. Anal. Chem., 1975, pp. 359 to 361, 274, Springer-Verlag.

Mrowietz, U., "Concepts of the mechanisms of action of cyclosporin in psoriasis. A review with guidelines on therapy", Hautarzt, 1993, Abstract, 44(6).

Traber, R. et al, "162. Isolierung und Strukturermittlung der neuen Cyclosporine E, F, G, H und I", Helvetica Chimica Acta, 1982, pp. 1655 to 1677, vol. 65, Fasc. 5, Schweizerische Chemische Gesellschaft. (Abstract in English).

Tosco, P. et al, "Physicochemical Profiling of Sartans: A Detailed Study of Ionization Constants and Distribution Coefficients", Helvetica Chimica Acta, 2008, pp. 468 to 482, vol. 91, Verlag Helvetica Chimica Acta AG, Zurich, Switzerland.

Xie, J.-R et al, "Cardioprotective effects of cyclosporine A in an in vivo model of myocardial ischemia and reperfusion", Acta Anaesthesiologica Scandinavica, 2007, pp. 909-913, 51.

Dzik, J.M. et al, "Effect of cyclosporin A on immunological response in lungs of guinea pigs infected with *Trichinella spiralis*", Acta Biochimica Polonica, 2002, pp. 233 to 247, col. 49, No. 1.

Schmid, F. X, "Prolyl Isomerases", Advances in Protein Chemistry, 2002, pp. 243 to 282, vol. 59, Academic Press.

Umland, S.P. et al, "Effects of Cyclosporin A and Dinactin on T-Cell Proliferation, Interleukin-5 Production, and Murine Pulmonary Inflammation", Am. J. Respir. Cell Mol. Biol., 1999, p. 481 to 492, vol. 20.

Tai, D.C-S. et al, "Correction of motion artifact in transmembrane voltage-sensitive fluorescent dye emission in hearts", Am J Physiol Heart Circ Physiol, 2004, pp. H985 to H993, 287.

Liu, Y. et al, "A fluorescence polarization-based assay for peptidyl prolyl cis/trans isomerase cyclophilin A", Analytical Biochemistry, 2006, p. 100 to 107, 356, Elsevier Inc.

Schmutz, J.L. et al, "New nail and hair side-effects of cyclosporin", Annales De Dermatologie et de Venereologie, 2000, p. 769, vol. 127, Issue 8-9.

Leshnower, B.G. et al, "Cyclosporine Preserves Mitochondrial Morphology After Myocardial Ischemia/Reperfusion Independent of Calcineurin Inhibition", Ann Thorac Surg, 2008, pp. 1286 to 1292, 86, Elsevier Inc.

Ozkisacik, E.A. et al, "Effects of Cyclosporin A on Neurological Outcome and Serum Biomarkers in the Same Setting of Spinal Cord Ischemia Model", Ann Vasc Surg, 2006, pp. 243 to 249, 20.

Watanabe, T. et al, "Short report Effect of SDZ PSC 833 ([3'-keto-Bmt1]-[Val2]-cyclosporin) on serum protein binding and distribution to blood cells of doxorubicin, vincristine and etoposide in vitro", Anti-Cancer Drugs, 1997, pp. 400 to 404, vol. 8., Rapid Science Publishers.

Gafter-Gvili, A. et al, "Cyclosporin A-induced hair growth in mice is associated with inhibition of hair follicle regression", Arch Dermatol Res, 2004, pp. 265 to 269, 296, Springer-Verlag.

Cassarino, D. S. et al, "Cyclosporin A Increases Resting Mitochondrial Membrane Potential in SY5Y Cells and Reverses the Depressed Mitochondrial Membrane Potential of Alzheimer's Dis-

(56) References Cited

OTHER PUBLICATIONS ease Cybrids", Biochemical and Biophysical Research Communications, 1998, pp. 168 to 173, 248, Academic Press.

Awumey, E. M. et al, "Molecular and Functional Evidence for Calcineurin-A α and β Isoforms in the Osteoclast: Novel Insights into Cyclosporin A Action on Bone Resorption", Biochemical and Biophysical Research Communications, 1999, pp. 248 to 252, 254, Academic Press.

Pasero, G. et al, "Risks and benefits of low-dosage cyclosporin in rheumatoid arthritis—Emerging evidence of a therapeutic role", Biodrugs, 1997, Abstract, vol. 7, Issue 5.

Winkler, M., "Cyclosporin as Baseline Immunosuppression in Solid Organ Transplantation", BioDrugs, 2000, pp. 185 to 193, vol. 14, Issue 3, Adis International Limited.

Bernstein, I.L. et al, "How does auranofin compare with methotrexate and cyclosporin as a corticosteroid-sparing agent in severe asthma?", Biodrugs, 1997, abstract, vol. 8, Issue 3.

Wang, X.J. et al, "Peptidyl-Prolyl Isomerase Inhibitors", Biopolymers (Peptide Science), 2006, pp. 125 to 146, vol. 84, Wiley Periodicals, Inc.

Van Westrhenen, R. et al, "Cyclosporin A Induces Peritoneal Fibrosis and Angiogenesis during Chronic Peritoneal Exposure to a Glucose-Based, Lactate-Buffered Dialysis Solution in the Rat", Blood Purif, 2007, pp. 466 to 472, 25, S. Karger AG, Basel.

Schultz, K.R. et al, "Effect of gastrointestinal inflammation and age on the pharmacokinetics of oral microemulsion cyclosporin A in the first month after bone marrow transplantation", Bone Marrow Transplantation, 2000, pp. 545 to 551, 26, Macmillan Publishers Ltd.

Duncan, N. et al, "Optimizing the use of cyclosporin in allogeneic stem cell transplantation", Bone Marrow Transplantation, 2006, pp. 169 to 174, 38, Nature Publishing Group.

Panayi, G.S. and Tugwell, P., Chairmen, "The Use of Cyclosporin A Microemulsion in Rheumatoid Arthritis: Conclusions of an International Review", British Journal of Rheumatology, 1997, pp. 808 to 811, 36.

Eedy, D.J., "Genetic syndrome with ichthyosis: congenital ichthyosis, follicular atrophoderma, hypotrichosis, and woolly hair; second report", Correspondence, British Journal of Dermatology, 2002, pp. 604 to 631, 147.

Duefer, M. et al, "Diabetogenic Effect of Cyclosporin A is Mediated by Interference with Mitochondrial Function of Pancreatic B-Cells", Molecular Pharmacology, 2001, pp. 873 to 879, vol. 60, No. 4.

Dobson, S. et al, "Characterization of protein Ser/Thr phosphatases of the malaria parasite, *Plasmodium falciparum*: inhibition of the parasitic calcineurin by cyclophilin-cyclosporin complex", Molecular and Biochemical Parasitology, 1999, pp. 167 to 181, 99, Elsevier Science B.V.

Thali, M., "Cyclosporines: immunosuppressive drugs with anti-HIV-1 activity", Molecular Medicine Today, 1995, pp. 287 to 291, Elsevier Science Ltd.

Lu, K.P. et al, "Prolyl cis-trans isomerization as a molecular timer", Nature Chemical Biology, 2007, pp. 619 to 629 , vol. 3, No. 10.

Quesada, A.J. et al, "La ruta de senalizacion CA++/Calcineurina/NFAT en activacion endotelial y angiogenesis: efetos de la ciclosporina A", Nefrologia, 2003, pp. 44 to 48, vol. XXIII, Suplemento 3.

Pape, L. et al, "Cyclosporin A—induced remission of primary membranous glomerulonephritis in a child", Nephrology Dialysis Transplantation, 2004, p. 3207, vol. 19, No. 12, ERA-EDTA.

Kiyomasu, T. et al, "Cyclosporin A Treatment for Membranoproliferative Glomerulonephritis Type II", Nephron, 2002, pp. 509 to 511, 91, S. Karger AG, Basel.

Akdemir, G. et al, "Therapeutic efficacy of intraventricular cyclosporine A and methylprednisolone on a global cerebral ischemia model in rats", Neurological Research, 2005, abstract, vol. 27, Issue 8.

Rodella, L. et al, "Cyclosporine-A Delays the End-Plate Degeneration in Denerved Rat Muscles", Neuroscience Research Communications, 2002, pp. 85 to 92, vol. 31, No. 2, Wiley-Liss, Inc.

Chao, S. et al, "Juglone, an inhibitor of the peptidyl-prolyl isomerase Pin1, also directly blocks transcription", Nucleic Acids Research, 2001, pp. 767 to 773, vol. 29, No. 3, Oxford University Press.

Boehringer, D., et al, "Cyclosporin-A—Augentropfen bei Nummuli nach Adeno-virus-Keratokonjunktivitis", Ophthalmologe, 2008, pp. 592 to 594, 105, Springer Medizin Verlag.

Reinhard, T. et al, "Lokales Cyclosporin A bei Nummuli nach Keratoconjunctivitis epidemica-Eine Pilotstudie", Ophthalmologe, 2000, pp. 764 to 768, 97, Springer-Verlag.

Hackert, T. et al, "Ciclosporin aggravates tissue damage in ischemia reperfusion-induced acute pancreatitis", Pancreas, 2006, Abstract, vol. 32, Issue 2.

Arimori, K. et al, "Effect of P-Glycoprotein Modulator, Cyclosporin A, on the Gastointestinal Excretion of Irinotecan and Its Metabolite SN-38 in Rats", Pharmaceutical Research, 2003, pp. 910 to 917, vol. 20, No. 6, Plenum Publishing Corporation.

Kinahan, P.E. et al, "1997 International Meeting on Fully Three-Dimensional Image Reconstruction in Radiology and Nuclear Mediine", Physics in Medicine and Biology, 1998, cover sheet, vol. 43, Issue 4.

Malesevic, M. et al, "Simple and efficient synthesis of new trifunctional templates", Peptides, 2004, pp. 391 and 392, Proceedings of the 3rd International and Twenty-Eighth European Peptide Symposium, Kenes International, Israel.

Carroll, G.J. et al, "Letters to the Editor Effective control of incomplete reactive arthritis with cyclosporin", Rheumatology, 2001, pp. 945 to 947, 40.

Bouchta, N.B. et al, "Conversion from Tacrolimus to Cyclosporin is Associated with a Significant Improvement of Glucose Metabolism in Patients with New-Onset Diabetes Mellitus after Renal Transplantation", Transplantation Proceedings, 2005, pp. 1857 to 1860, 37, Elsevier Inc.

Dalmarco, E. M. et al, "Additional evidence of acute anti-infllammatory effects of cyclosporin A in a murine model of pleurisy", Transplant Immunology, 2004, pp. 151 to 157, 12, Elsevier B.V.

Steffan, J. et al, "A systematic review and meta-analysis of the efficacy and safety of cyclosporin for the treatment of atopic dermatitis in dogs", Veterinary Dermatology, 2006, pp. 3 to 16, 17.

\* cited by examiner

CYCLOSPORIN DERIVATIVES

CROSS REFERENCE TO RELATED APPLICATIONS

This application is a continuation application of international patent application PCT/EP 2010/005053, filed Aug. 17, 2010, designating the United States and claiming priority from German application 10 2009 037 551.1, filed Aug. 17, 2009, and the entire content of both applications is incorporated herein by reference.

FIELD OF THE INVENTION

The present invention relates to cyclosporin derivatives, a method for concentrating a cyclosporin derivative in an extracellular space of a multicellular object, the use of the cyclosporin derivatives according to the invention to produce a medicament and a pharmaceutical composition comprising a cyclosporin derivative according to the invention.

BACKGROUND OF THE INVENTION

The effect of biologically effective molecules, which are generally pharmaceutical active ingredients, develops mostly both inside and outside biological cells. Hitherto, primarily the problem has occurred that active ingredients whose effect is to develop only inside the cell cause undesired changes in the extracellular space even before passing through the cell membrane. The problem that additionally arises here is that one and the same active ingredient can develop a different effect inside and outside the cell. The actual effect thus comprises two components—the desired intracellular and the undesired extracellular. If the intracellular effect is to be achieved, the extracellular (side-)effect often also had to be accepted—because the transport to the cell generally includes the crossing of an extracellular space.

An equally important problem, but one not hitherto described in the state of the art, is the administration of active ingredients which are supposed to or can develop their effect outside the cell only. Above all in medicine a range of active ingredients is known which not only do not develop the intended effect in the cell but actually have a toxic effect or are harmful in some other way. To this is added the fact that, to achieve a specific extracellular effect, a much higher dose must be administered than is actually required in order to compensate for the "loss" of the active ingredients which have migrated into the inside of the cell.

Active ingredients can act extracellularly on molecules or structures. Such biological molecules of the extracellular space can be for example enzymes, inhibitors, activators or receptors. By "structures" is meant for example the extracellular matrix which is formed from the totality of the macromolecules which are found outside the plasma membrane of cells in tissues and organs.

Important active ingredients in current medical research are effectors which can inhibit inflammatory processes in biological objects, preferably in veterinary and human medicine. Effectors of peptidyl-prolyl-cis/trans-isomerases (PPIases), i.e. PPIase inhibitors, are of particular importance.

While these effectors can differ between the individual PPIase families (Nature Chemical Biology. 3(10):619-29, 2007; Cellular & Molecular Life Sciences. 63(24):2889-900, 2006; Current Topics in Medicinal Chemistry. 3(12):1315-47, 2003; Advances in Protein Chemistry. 59:243-82, 2001), they often have similar inhibiting power compared with sequence-similar family members. Because PPIases within a family can influence very different biochemical reactions, the diagnostic or pharmacological effect of administered active ingredients depends directly on the concentration reached in very different distribution spaces. Thus e.g. some of these PPIase inhibitors (e.g. Biopolymers 84 (2006)125-146; Chemical & Pharmaceutical Bulletin. 54(3):372-376, 2006; Chemistry & Biology. 10(1):15-24, 2003; Nucleic Acids Research. 29(3):767-773, 2001), such as e.g. therapeutically used cyclosporin, are only poorly soluble in water. (DE 19859910). Nevertheless, much higher concentrations are found inside cells after customary medicinal application. It is suspected that the active ingredients pass through the cell membrane and then bind to PPIases intracellularly present. For a cyclosporin derivative (SDZ IMM 125) thus (Anti-Cancer Drugs. 8(4):400-404, 1997; Journal of Pharmacokinetics & Biopharmaceutics. 22(5):327-65, 1994) an approximately 8× higher concentration was able to be detected in blood cells than in the surrounding plasma.

Cyclosporin (also ciclosporin) is a cyclic oligopeptide with an immunosuppressive and calcineurin-inhibiting effect. It is characterized by a selective and reversible immunosuppression mechanism. It selectively blocks the activation of T lymphocytes via the production of specific cytokines which participate in the regulation of these T cells. Above all the synthesis of interleukin-2 is inhibited, whereby simultaneously the proliferation of cytotoxic T lymphocytes which e.g. are responsible for the rejection of foreign tissue is suppressed. Cyclosporin acts intracellularly by binding to the so-called cyclophilines or immunophilines which belong to the family of cyclosporin-binding proteins.

Inhibitors of cyclophilines have a very broad therapeutic spectrum, such as e.g. the treatment of diseases of the respiratory tract, such as e.g. asthma, COPD, pneumonia or emphysema (Expert Opinion on Investigational Drugs 12 (2003), 647-653, Biodrugs 8 (1997) 205-215, American Journal of Respiratory Cell & Molecular Biology 20 (1999), 481-492), metabolic diseases such as diabetes (Transplantation Proceedings 37 (2005), 1857-1860, Molecular Pharmacology 60 (2001), 873-879), inflammatory diseases of the digestive tract (Bone Marrow Transplantation 26 (2000), 545-551, Pharmaceutical Research 20 (2003), 910-917), disorders of the immune system (Immunology Letters 84 (2002), 137-143, Acta Biochimica Polonica 49 (2002), 233-247), inflammations (Journal of Periodontal Research 42 (2007), 580-588, Journal of Neurology, Neurosurgery & Psychiatry 76 (2005), 1115-1120, Transplant Immunology 12 (2004), 151-157), cardiovascular diseases (Journal of Hypertension 17 (1999), 1707-1713, Drug & Chemical Toxicology 21 (1998), 27-34), neurological diseases (Annals of Vascular Surgery 20 (2006), 243-249), diseases associated with a disruption of angiogenesis (Blood Purification 25 (2007), 466-472, International Angiology 24 (2005), 372-379, Nefrologia 23 (2003), 44-48), for the suppression of the immune response in organ transplantation (Bone Marrow Transplantation 38 (2006), 169-174, Biodrugs 14 (2000), 185-193, Clinical Immunotherapeutics 5 (1996), 351-373) and of autoimmune diseases (Immunology & Immunopathology 82(3), 197-202, 1997), arthritic diseases (British Journal of Rheumatology 36 (1997), 808-811, Biodrugs 7 (1997), 376-385), dermatitides (Veterinary Dermatology 17 (2006), 3-16), psoriasis (Journal of Dermatological Treatment 16 (2005), 258-277, Hautarzt 44 (1993), 353-360), in allergies (Cornea 27 (2008), 625, Journal of Small Animal Practice 47 (2006), 434-438, Clinical & Experimental Ophthalmology 34 (2006), 347-353), in multiple sclerosis (Immunopharmacology & Immunotoxicology 21 (1999), 527-549, Journal of Neuroimaging 7 (1997), 1-7), diseases caused by ischemia, such as e.g. infarctions of the heart (Annals of Thoracic Surgery 86 (2008), 1286-1292, Acta Anaesthesiologica Scandinavica 51 (2007), 909-913), of the pancreas (Pancreas 32 (2006), 145-151) or of the brain (Annals of Vascular Surgery 20 (2006), 243-249, Neurological Research 27 (2005), 827-834), kidney diseases, such as e.g. glomerulonephritis (Nephrology Dialysis Transplantation 19 (2004), 3207, Nephron 91 (2002), 509-511), tumours (Journal of Investigative Dermatology 128 (2008), 2467-2473, Endocrinology 148 (2007), 4716-4726), in multiple myelomas (Leukemia 12 (1998), 505-509, Leukemia & Lymphoma 16 (1994), 167-170), in acute or chronic leukaemia (Cancer Chemotherapy & Pharmacology 52 (2003), 449-452, Cancer 97 (2003), 1481-1487), muscular degeneration (Neuroscience Research Communications 31 (2002), 85-92), cachexia (International Journal of Cardiology 85 (2002), 173-183, Drugs 58 (1999), 953-963, 1999), Reiter's Syndrome (Rheumatology 40 (2001), 945-947), bone degradation diseases (European Journal of Pharmacology 564 (2007), 226-231, Biochemical & Biophysical Research Communications 254 (1999), 248-252), in Alzheimer's disease (Biochemical & Biophysical Research Communications 248 (1998), 168-173, Chinese Medical Journal 115 (2002), 884-887), malaria (Molecular & Biochemical Parasitology 99 (1999), 167-181), septic and toxic shock syndrome (Journal of Pharmacology & Experimental Therapeutics 311 (2004), 1256-1263), myalgia (British Journal of Dermatology 147 (2002), 606-607), in a virus infection (Expert Opinion on Emerging Drugs 13 (2008), 393-416), such as e.g. HIV-1, HIV-2, HIV-3 (Journal of Infectious Diseases 194 (2006), 1677-1685, Molecular Medicine Today 1 (1995), 287-291, 1995), cytomegaloviruses (Journal of Virology 81 (2007), 9013-9023) or adenoviruses (Ophthalmologe 105 (2008), 592-594, Ophthalmologe 97 (2000), 764-768) and for promoting hair growth (Archives of Dermatological Research 296(6), 265-269, 2004, Annales de Dermatologie et de Venereologie 127 (2000), 769).

The complex of cyclosporin and cyclophilin then blocks the serine-threonine-phosphatase calcineurin. Its activity state in turn controls the activation of transcription factors such as, say, NF-Kappa B or NFATp/c which play an important role in the activation of various cytokine genes, also including that for interleukin-2. The immunocompetent lymphocytes are hereby arrested during the G0 or G1 phase of the cell cycle, because the proteins essential for cell division such as interleukin-2 can no longer be produced. T helper cells which increase the activity of the cytotoxic T cells responsible for rejection are the preferred point of attachment for cyclosporin.

In addition cyclosporin inhibits the synthesis and release of further lymphokines which are responsible for the proliferation of mature cytotoxic T lymphocytes and for further functions of the lymphocytes. The ability of cyclosporin to block interleukin-2 is critical for its clinical effectiveness: Transplant recipients who display a good tolerance of their transplants are characterized by a low production of interleukin-2. Conversely, in patients with a manifest rejection reaction, no inhibition of interleukin-2 production can be established.

SUMMARY OF THE INVENTION

The object of the present invention was to discover new, pharmaceutically active cyclosporin derivatives.

The object of the present invention was achieved by a cyclosporin derivative of general formula (I)

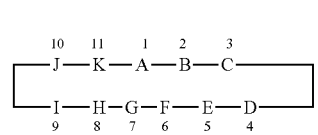

Formula I or a pharmaceutically compatible salt thereof,
wherein in Formula (I)
A is an amino acid residue of Formula (II),

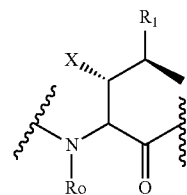

Formula II in which $R_1$ corresponds to a residue of Formula III

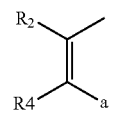

Formula III and is covalently bonded via the carbon atom a, or
in which $R_1$ corresponds to a residue of Formula IV

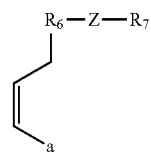

Formula IV and is covalently bonded via the carbon atom a, or
in which $R_1$ corresponds to a residue of Formula V

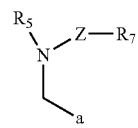

Formula V and is covalently bonded via the carbon atom a, or
in which $R_1$ corresponds to a residue of Formula VI

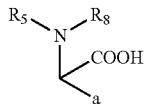

Formula VI and is covalently bonded via the carbon atom a, or
in which $R_1$ corresponds to a residue of Formula VII

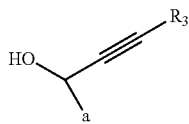

Formula VII and is covalently bonded via the carbon atom a, or
in which $R_1$ corresponds to a residue of Formula VIII

Formula VIII and is covalently bonded via the carbon atom a, or
in which $R_1$ corresponds to a residue of Formula IX

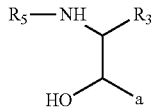

Formula IX and is covalently bonded via the carbon atom a,
wherein the C=O group in Formula II is covalently bonded to an alpha-amino group of B via an amide bond and the N—$R_o$ group in Formula II is covalently bonded to a carboxyl group of K via an amide bond,
B is an amino acid residue which is selected from the group consisting of:
  alpha-aminobutyric acid,
  alanine,
  threonine,
  valine,
  norvaline and
  alpha-aminobutyric acid, alanine, threonine, valine or norvaline modified in the side chain with a hydroxyl group,
C is a sarcosine residue,
D is an amino acid residue which is selected from the group consisting of:
  leucine,
  N-methyl leucine,
  valine,
  gamma-hydroxy-N-methyl leucine and
  gamma-hydroxy leucine,
E is an amino acid residue which is selected from the group consisting of:
  valine,
  norvaline and
  a modified valine or norvaline in which a carbon atom in the side chain is substituted by a hydroxyl group,
F is an amino acid residue which is selected from the group consisting of:
  leucine,
  N-methyl leucine,
  gamma-hydroxy-N-methyl leucine and
  gamma-hydroxy leucine,
G is an alpha-aminobutyric acid residue or an alanine residue,
H is a D-alanine residue,
I and J are residues which are selected, independently of one another, from the group consisting of
  leucine,
  N-methyl leucine,
  gamma-hydroxy-N-methyl leucine and
  gamma-hydroxy leucine,
and
K is N-methyl valine residue or valine residue,
wherein in Formulae II to IX
  $R_o$ represents H or $CH_3$,
  X represents H or
    hydroxyl or
    a hydroxyl group which is derivatized with an alkanoyl, aryloyl, alkylaminocarbonyl, arylaminocarbonyl, arylalkylaminocarbonyl, alkoxycarbonyl, aryloxycarbonyl, arylalkyloxycarbonyl group or a silyl protecting group,
  $R_2$ represents H or
    a substituted or unsubstituted monocyclic, bicyclic or tricyclic aryl or heteroaryl ring which is optionally substituted with $R_3$,
  $R_3$ is selected from the group consisting of:
    —Z—NY—$Y_1$,
    —Z—CO—Y,
    —Z—S—Y,
    —$Y_2$,
    —NY—$Y_1$,
    —CO—Y,
    —S—Y,
    —Z—O—Y and
    —O—Y,
  $R_4$ corresponds to the $R_2$ group as defined above, wherein $R_4$ and $R_2$ can be the same or different,
  Z is selected from the group consisting of:
    an unbranched, branched or cyclic alkyl group with 1 to 20 carbon atoms,
    an unbranched, branched or cyclic alkenyl group with 1 to 20 carbon atoms,
    an unbranched, branched or cyclic alkinyl group with 1 to 20 carbon atoms,
    a substituted or unsubstituted monocyclic, bicyclic or tricyclic aryl or heteroaryl ring and
    a group of the general formula —[$CH_2$]$_m$—O—($CH_2$)$_n$]$_o$, wherein m, n and o independently of each other are integers from 1 to 20,
  Y is selected from the group consisting of:
    H,
    the protected or unprotected amino acid residues Gly, D-Glu, D-Asp, D- and L-Cys($SO_3H$), unprotected peptide residues with a chain length of from 2 to 200 amino acid residues, containing one amino acid type or a combination of different amino acid types selected from Gly, D-Glu, D-Asp, D- and L-Cys ($SO_3H$), an alkyl, alkenyl, aryl, alkylaminocarbonyl, arylaminocarbonyl, arylalkylaminocarbonyl, alkylcarboxyl, alkoxycarbonyl, aryloxycarbonyl and arylalkyloxycarbonyl group, $Y_1$ corresponds to the Y group as defined above, wherein Y and $Y_1$ can be the same or different, $Y_2$ represents H, F, Cl, Br or I, $R_5$ is selected from the group consisting of:
   an alkyl, alkenyl, aryl, alkylaminocarbonyl, arylaminocarbonyl, arylalkylaminocarbonyl, alkylcarbonyl, alkoxycarbonyl, aryloxycarbonyl, arylalkyloxycarbonyl group,
   the amino acid residues Gly, D-Glu, D-Asp, D- and L-Cys($SO_3H$),
   peptide residues with a chain length of from 2 to 200 amino acid residues, containing one amino acid type or a combination of different amino acid types selected from Gly, D-Glu, D-Asp, D- and L-Cys ($SO_3H$),
   F, Cl, Br and I, $R_6$ is selected from the group consisting of:
   O, N and S,
   the protected or unprotected amino acid residues Gly, D-Glu, D-Asp, D- and L-Cys($SO_3H$), and
   peptide residues with a chain length of from 2 to 200 amino acid residues, containing one amino acid type or a combination of different amino acid types selected from Gly, D-Glu, D-Asp, D- and L-Cys ($SO_3H$), $R_7$ is selected from the group consisting of:
   a carboxyl, amino, thiol, hydroxyl group,
   F, Cl, Br, I,
   the protected or unprotected amino acid residues Gly, D-Glu, D-Asp, D- and L-Cys($SO_3H$), an alkyl, alkenyl, aryl, alkylaminocarbonyl, arylaminocarbonyl, arylalkylaminocarbonyl, alkoxycarbonyl, aryloxycarbonyl and arylalkyloxycarbonyl group,
   peptide residues with a chain length of from 2 to 200 amino acid residues, containing one amino acid type or a combination of different amino acid types selected from Gly, D-Glu, D-Asp, D- and L-Cys ($SO_3H$),
and $R_3$ corresponds to the $R_5$ group as defined above, wherein $R_8$ and $R_5$ can be the same or different.

The cyclosporin derivatives according to the invention have a pharmaceutical effectiveness, for example in the case of chronic inflammatory diseases.

The cyclosporin derivatives according to the invention can have a negative net charge at pH 6, which is why they cannot pass through a cell membrane under corresponding conditions.

The determination of the net charge of a peptide sequence can as a first approximation be established by means of a calculation, as stated e.g. in WO 2003/097706, or more precisely by corresponding biochemical experiments such as e.g. by means of isoelectric focusing (cf. Lexikon der Biochemie, 1$^{st}$ edition, 2005, Spektrum Akademischer Verlag) or by titration (cf. e.g. Fresenius' Journal of Analytical Chemistry 274 (1975), 359-361), Helvetica Chimica Acta 91 (2008), 468-482).

It is known to a person skilled in the art that the net charge of a molecule results from the sum of the part-charges of the individual functional groups.

The inventors of the present application have found that—in order to ensure that a cyclosporin derivative according to the invention will certainly remain in the extracellular space—the cyclosporin derivative should furthermore comprise no peptide section capable of passing through the membrane of a cell. By a "peptide section" is meant within the framework of the invention any section with more than one positively charged, i.e. basic, amino acid capable of passing through the membrane of a biological cell. The cyclosporin derivatives according to the invention are therefore preferably free from a peptide section capable of passing through the membrane of a biological cell. A peptide section or a peptide, such as must not be a constituent of the cyclosporin derivative according to the invention, can comprise for example one or more amino acids selected from the group consisting of arginine, lysine, histidine or combinations thereof. Peptides which are particularly capable of passing through the membrane of biological cells are in particular peptides from 5 to 20 of the amino acids listed above.

In a preferred embodiment of the cyclosporin derivative according to the invention, $R_1$ corresponds to a residue of Formula III

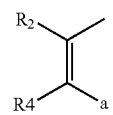

Formula III

In a further preferred embodiment of the cyclosporin derivative according to the invention, $R_1$ corresponds to a residue of Formula IV

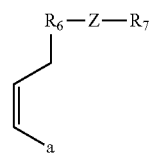

Formula IV

In a further preferred embodiment of the cyclosporin derivative according to the invention, $R_1$ corresponds to a residue of Formula V

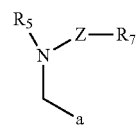

Formula V

In a further preferred embodiment of the cyclosporin derivative according to the invention, $R_1$ corresponds to a residue of Formula VI

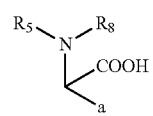

Formula VI

In a further preferred embodiment of the cyclosporin derivative according to the invention, $R_1$ corresponds, to a residue of Formula VII

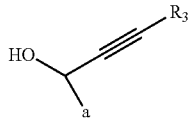

Formula VII

In a further preferred embodiment of the cyclosporin derivative according to the invention, $R_1$ corresponds to a residue of Formula VIII

Formula VIII

In a further preferred embodiment of the cyclosporin derivative according to the invention, $R_1$ corresponds to a residue of Formula IX

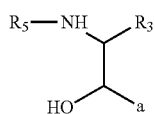

Formula IX

According to a quite particularly preferred embodiment of the present invention, the cyclosporin derivative of Formula (I) is selected from:

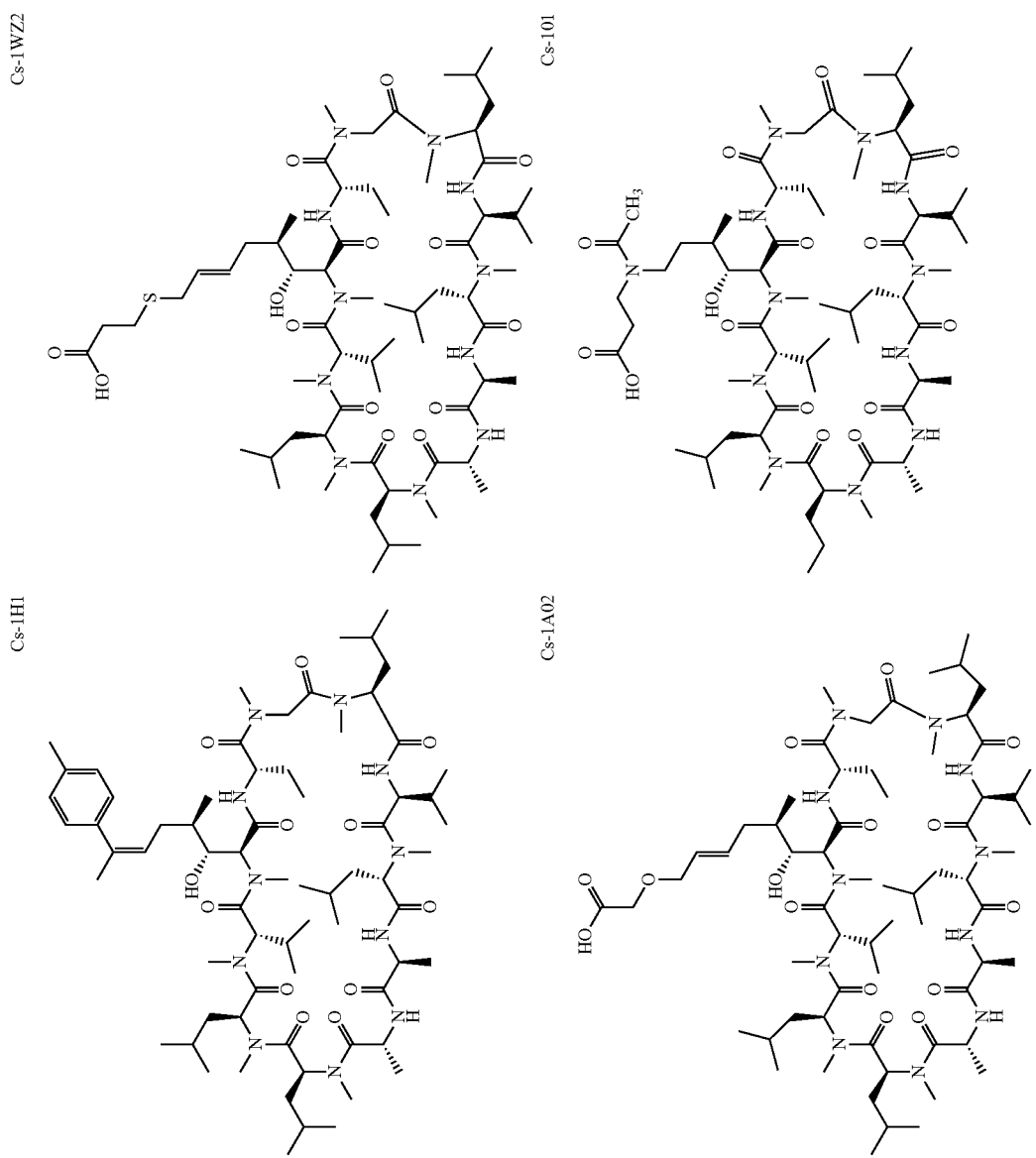

-continued
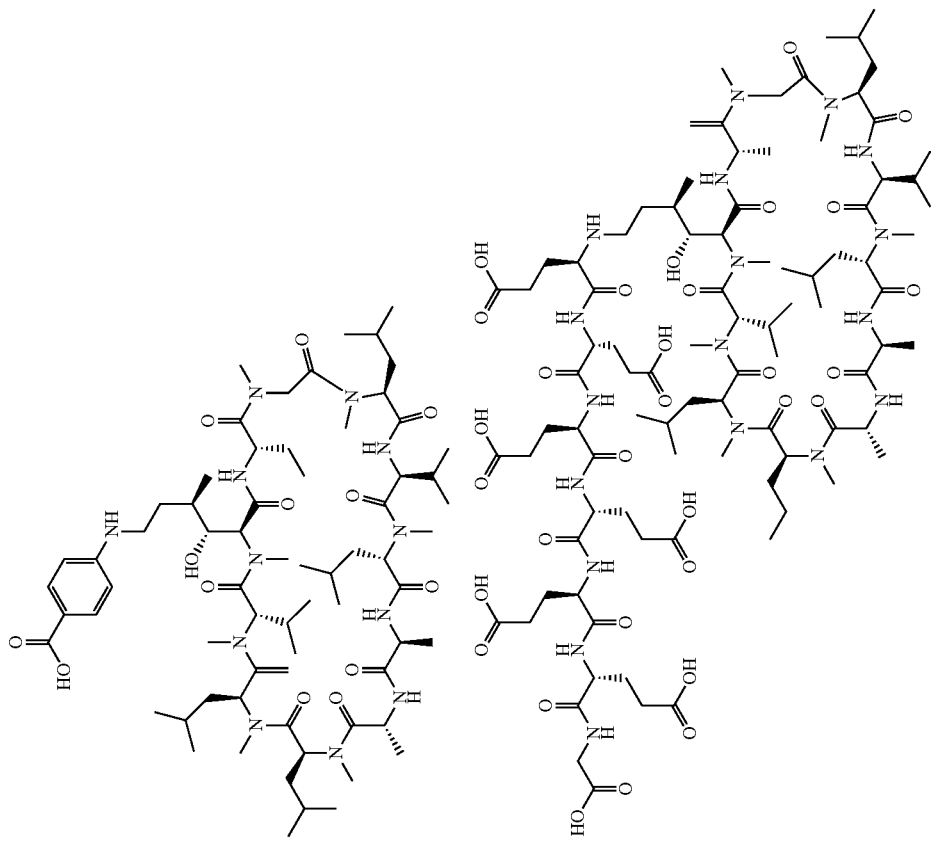
Cs-106
Cs-1011

-continued
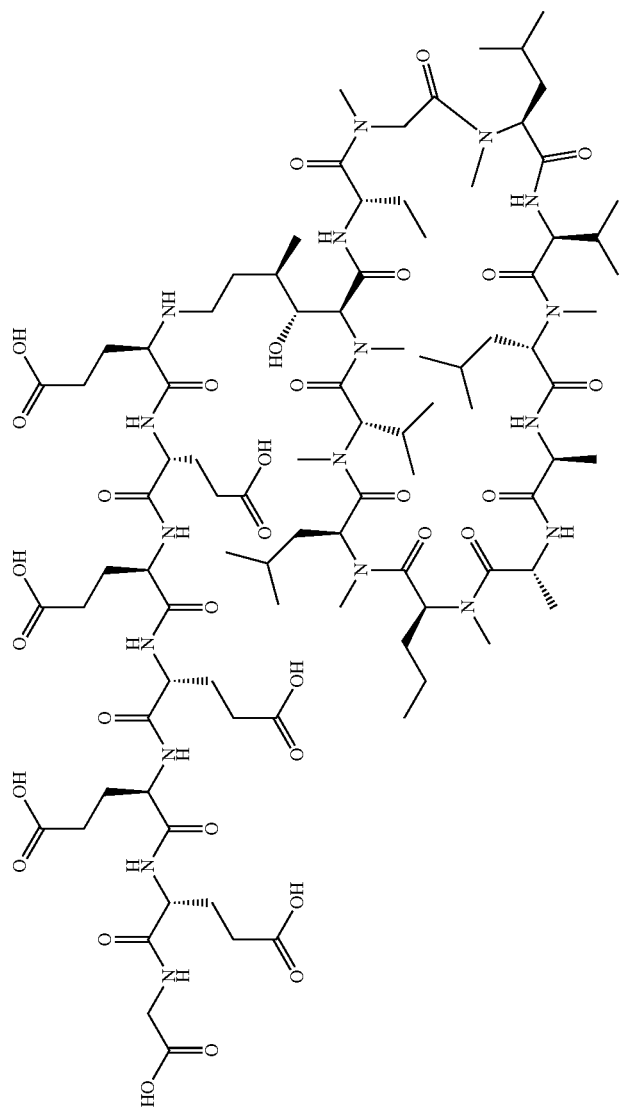
Cs-1011
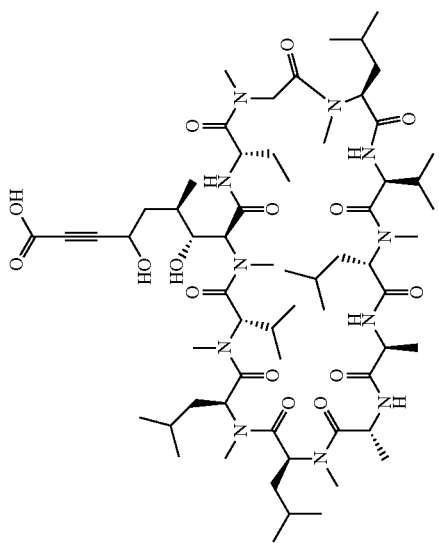
Cs-1Ad1
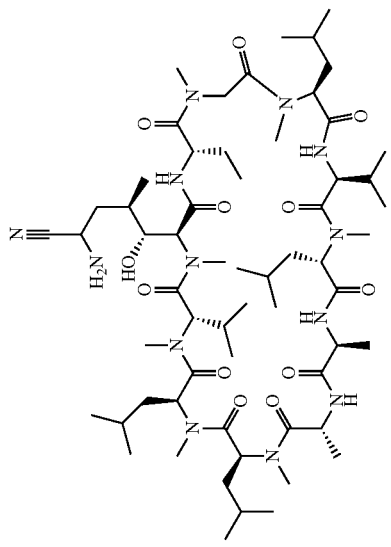
Cs-1S1

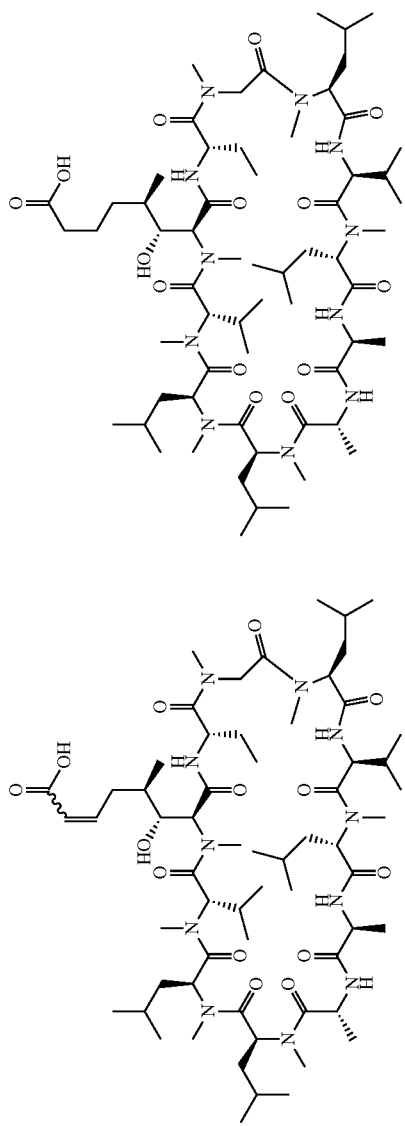
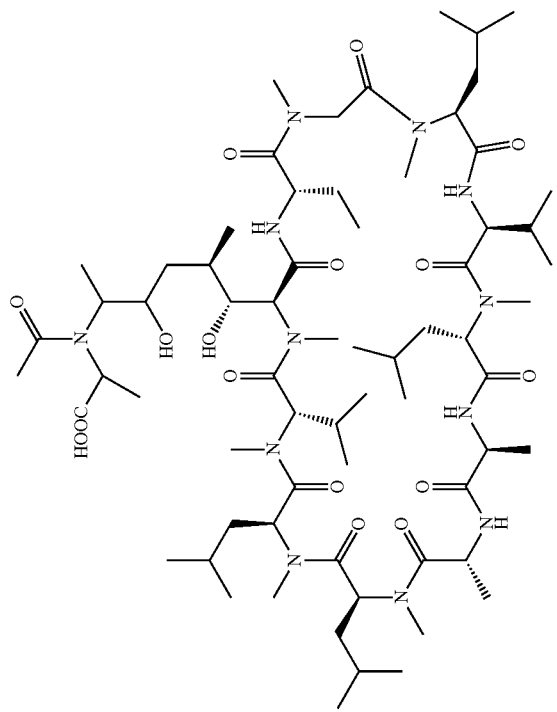

-continued
Cs-1H2
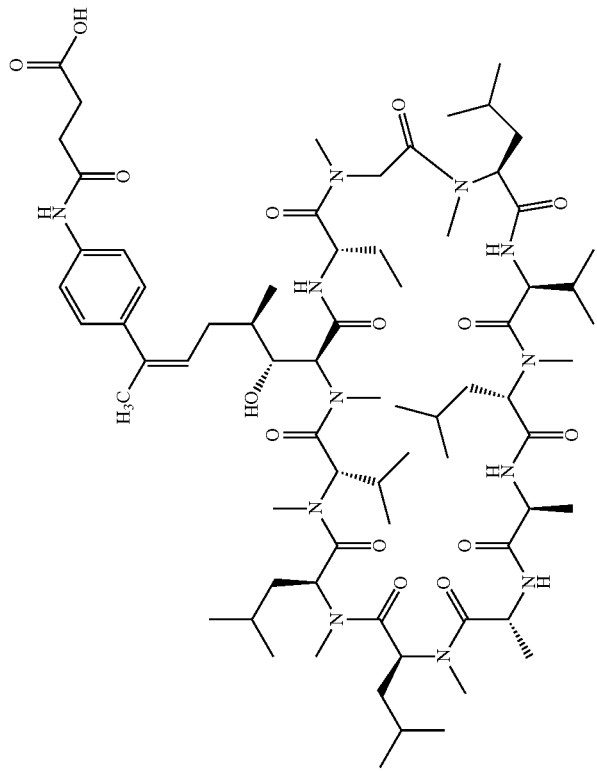

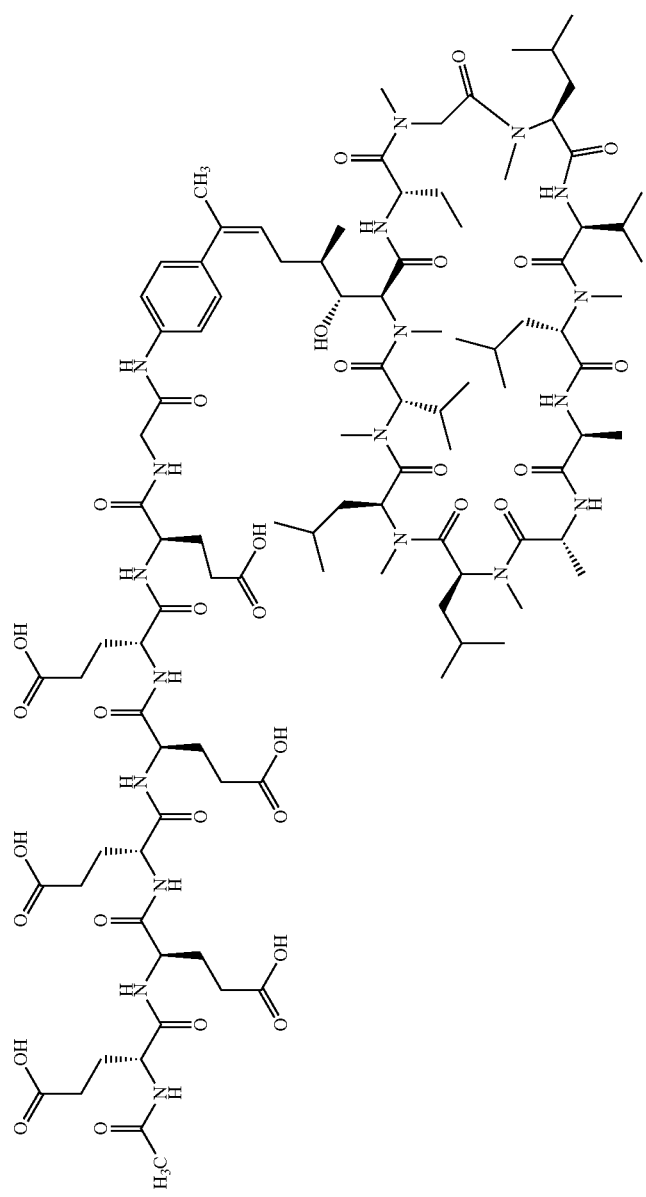

-continued
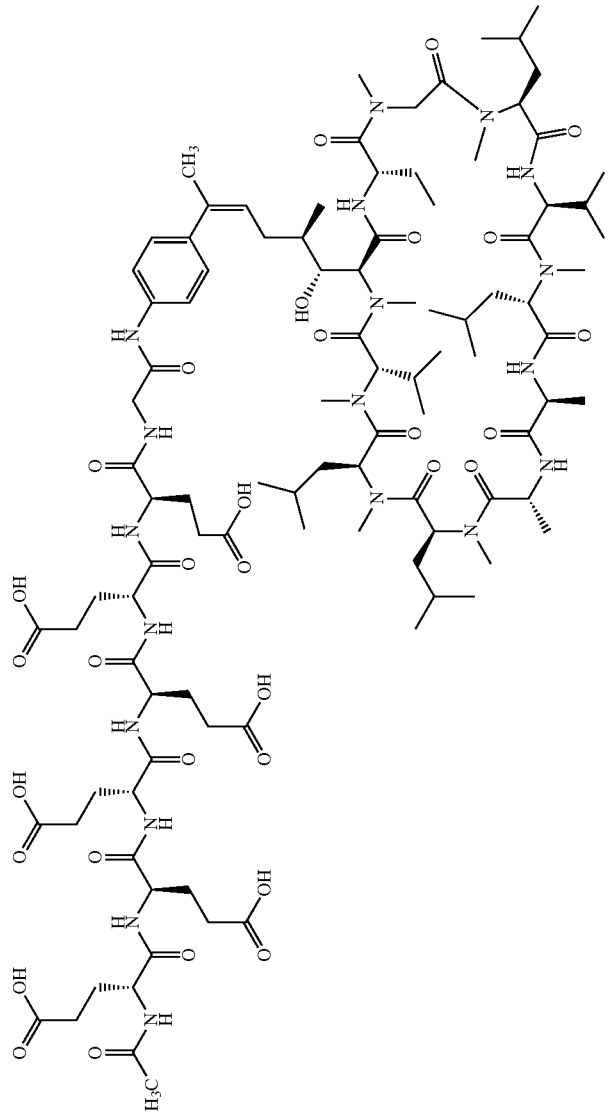
Cs-1H2-2
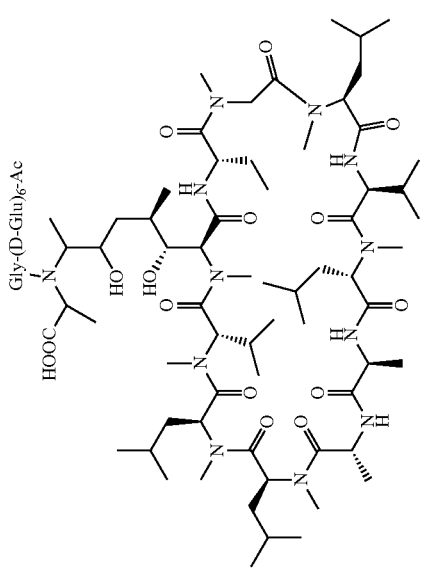
Cs-1S2
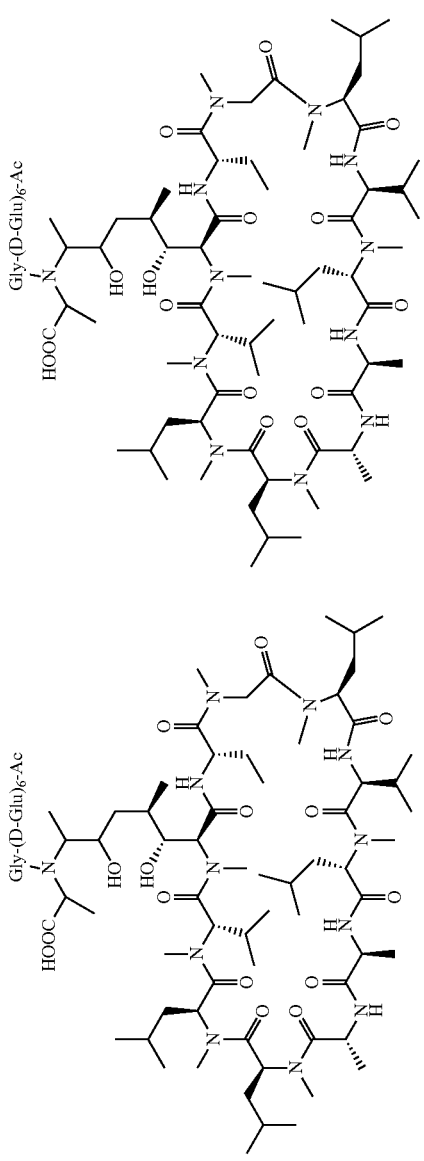
Cs-1E3

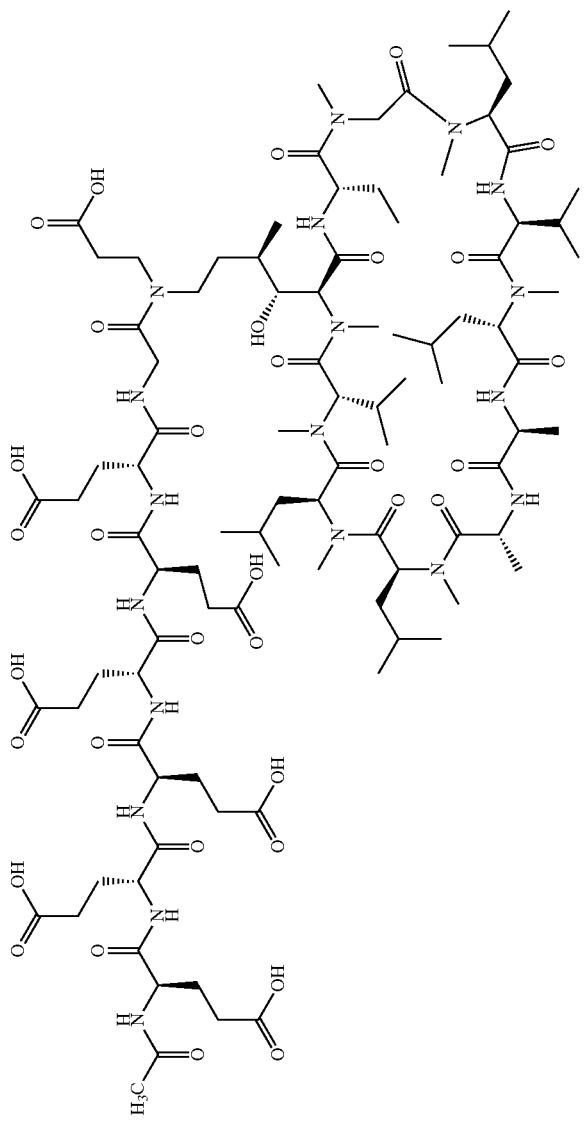

-continued
Cs-1H4
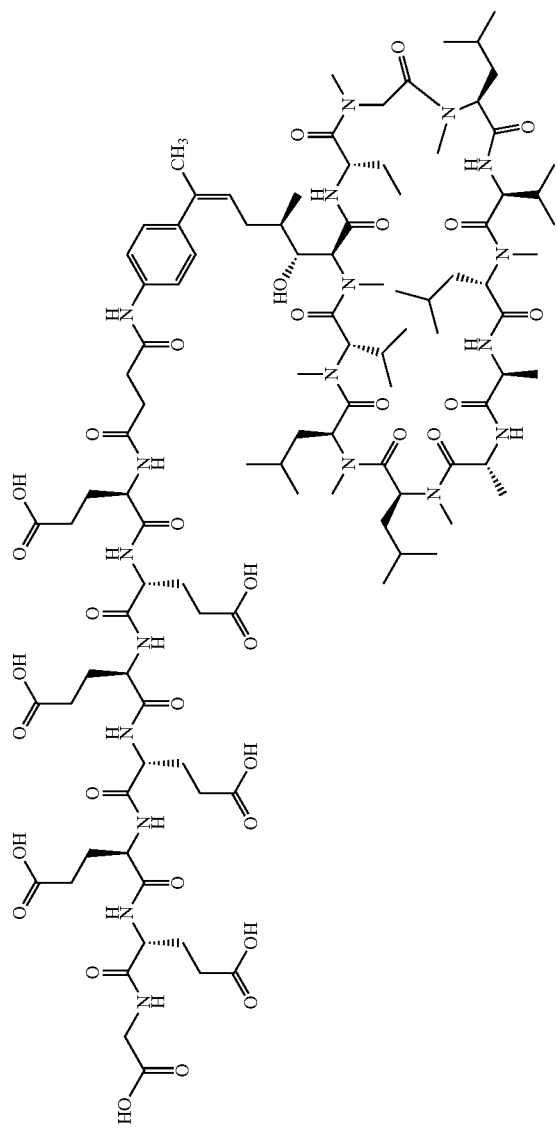

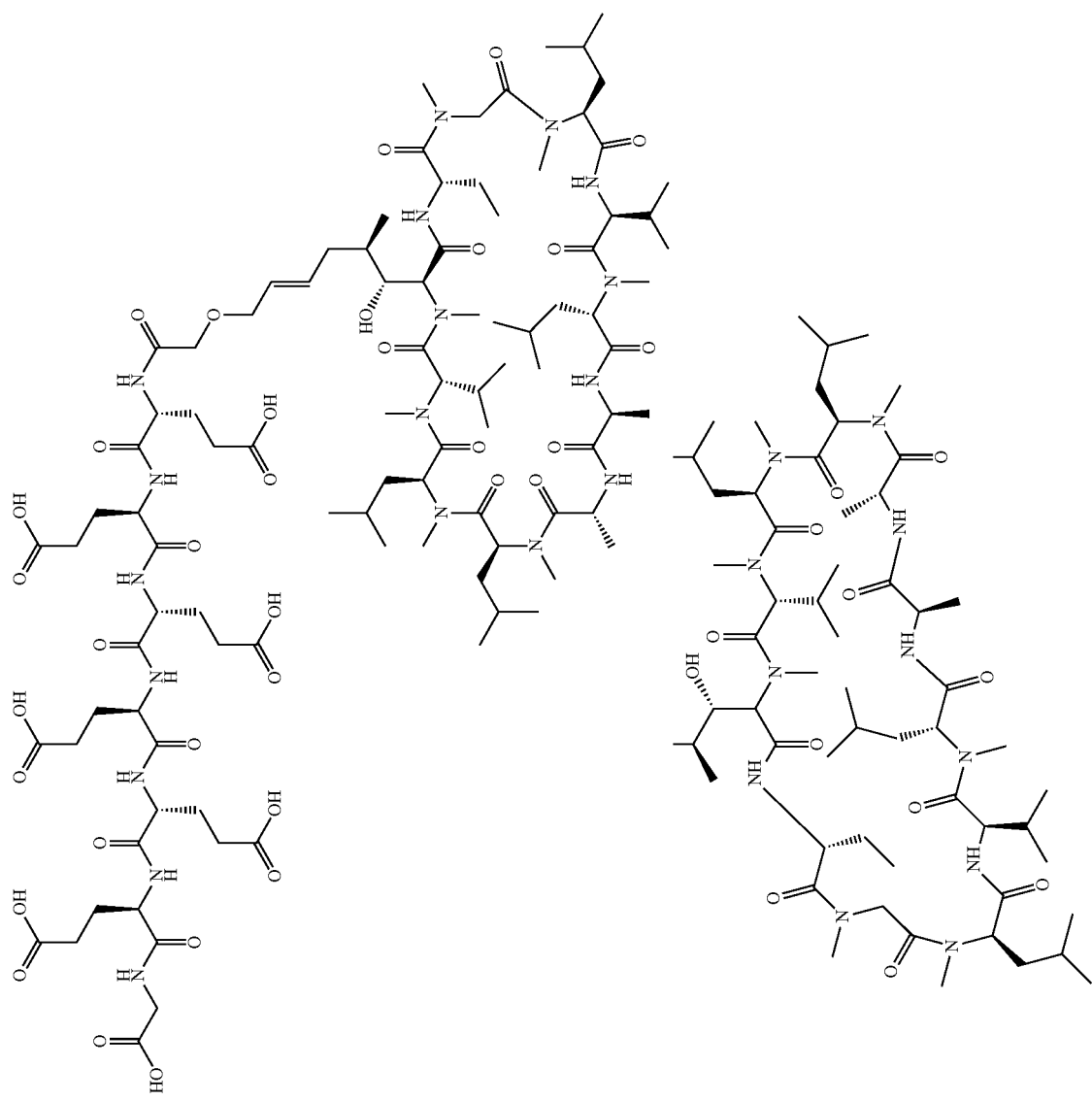
Cs-1WZ3

-continued
Cs-1A03
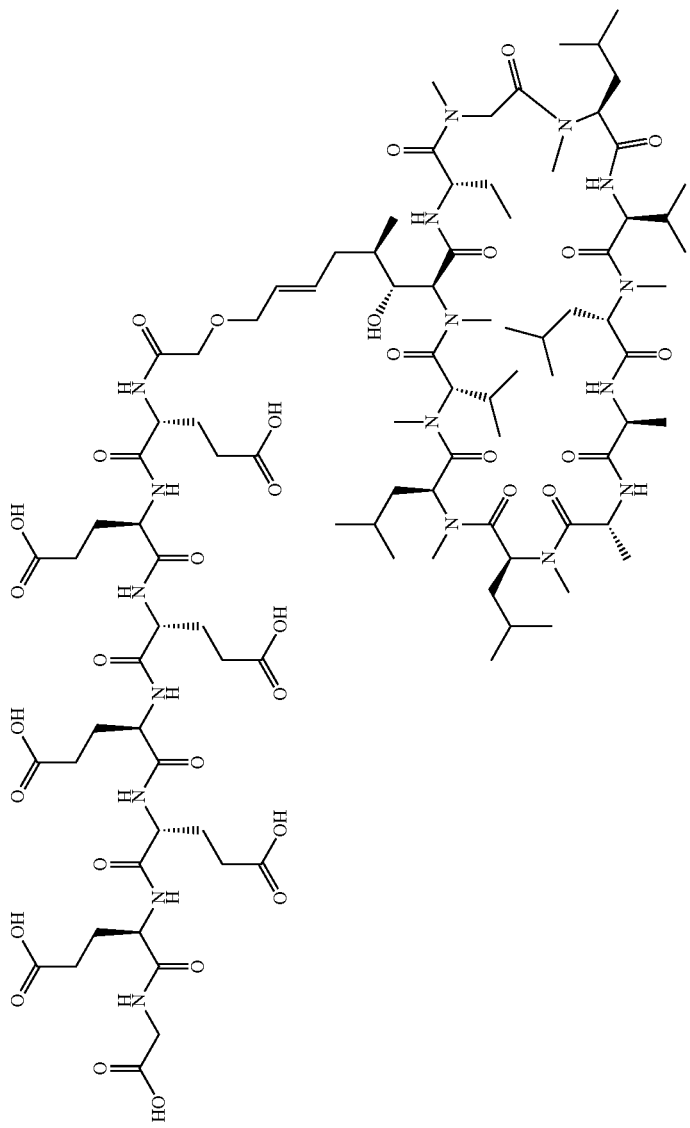

-continued
Cs-103
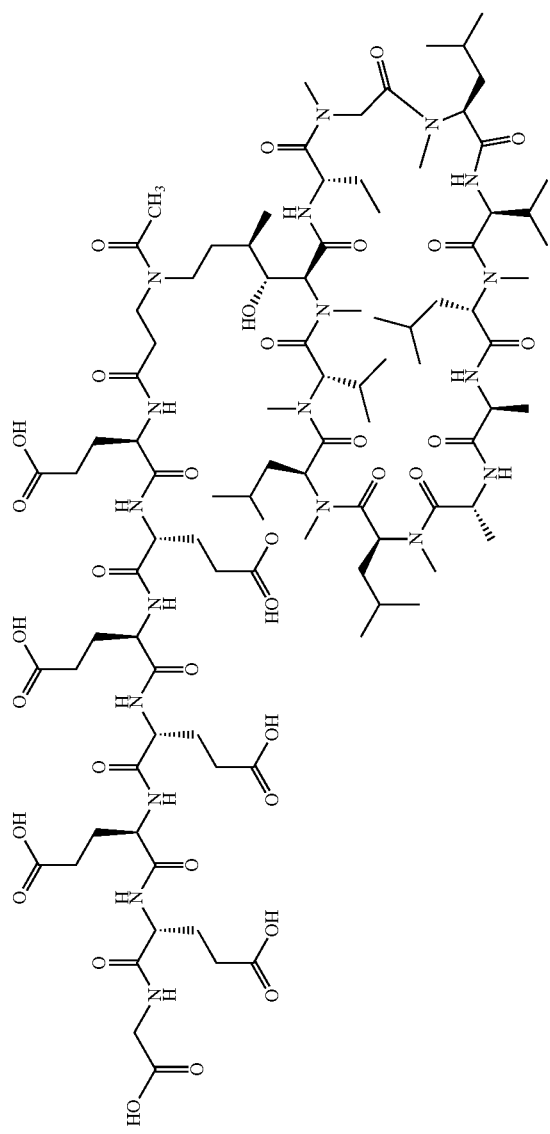

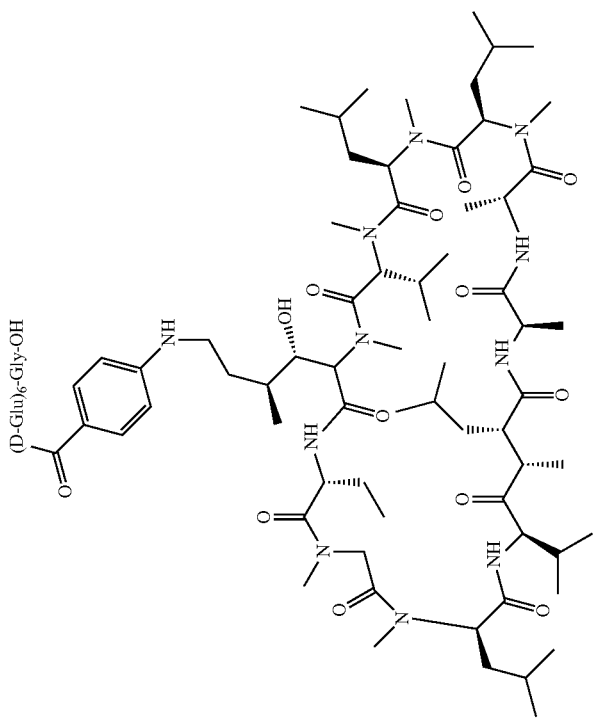
Cs-107

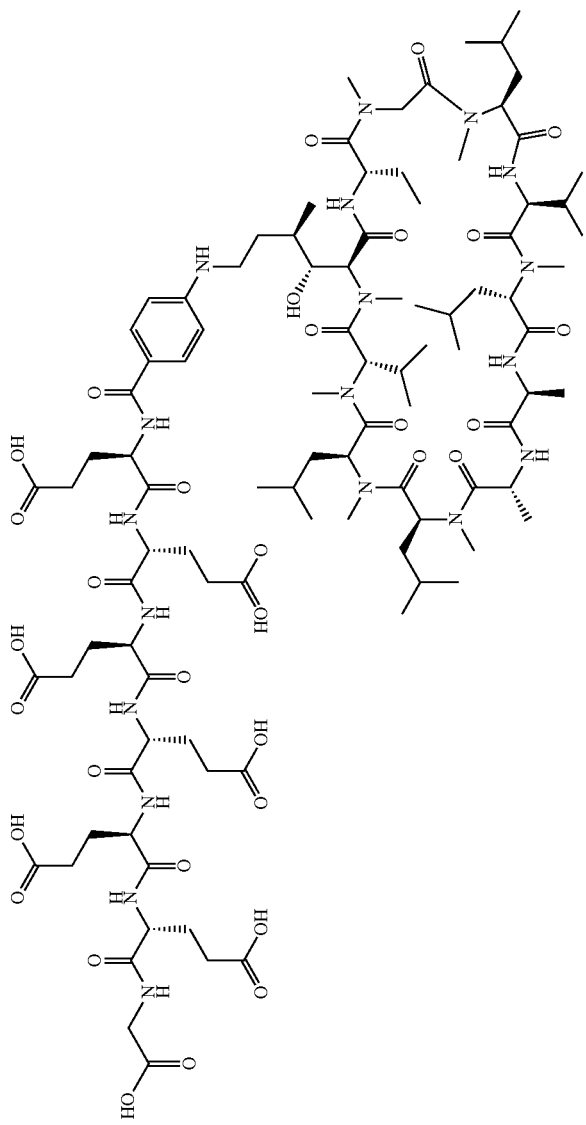
Cs-107

-continued
CsM5
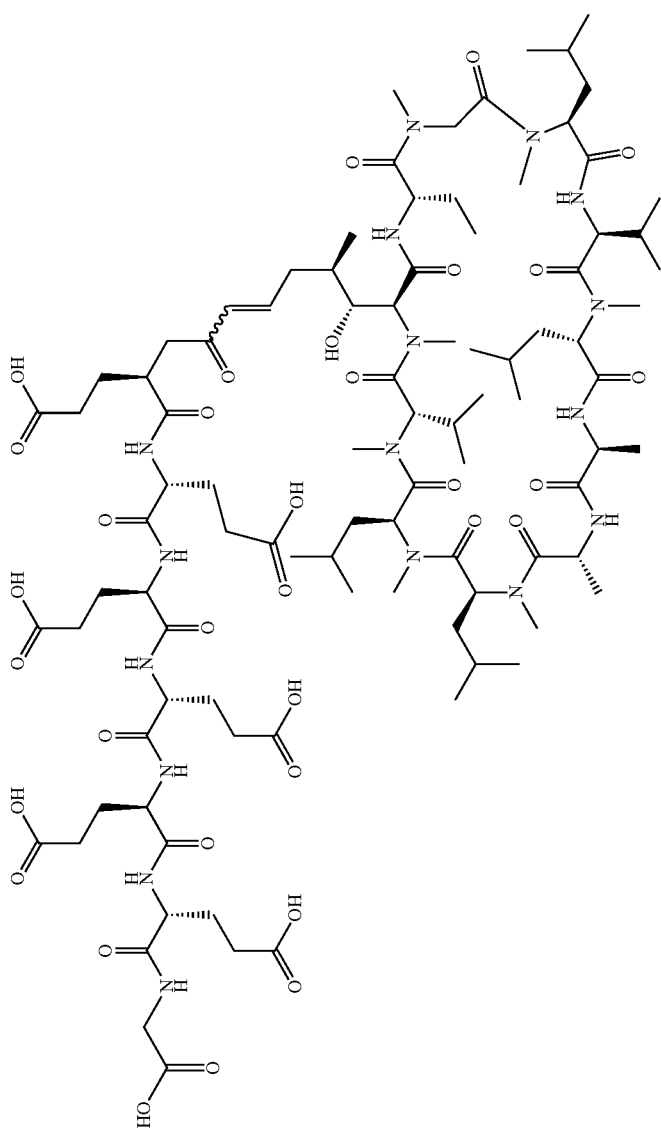

-continued
Cs-3E2
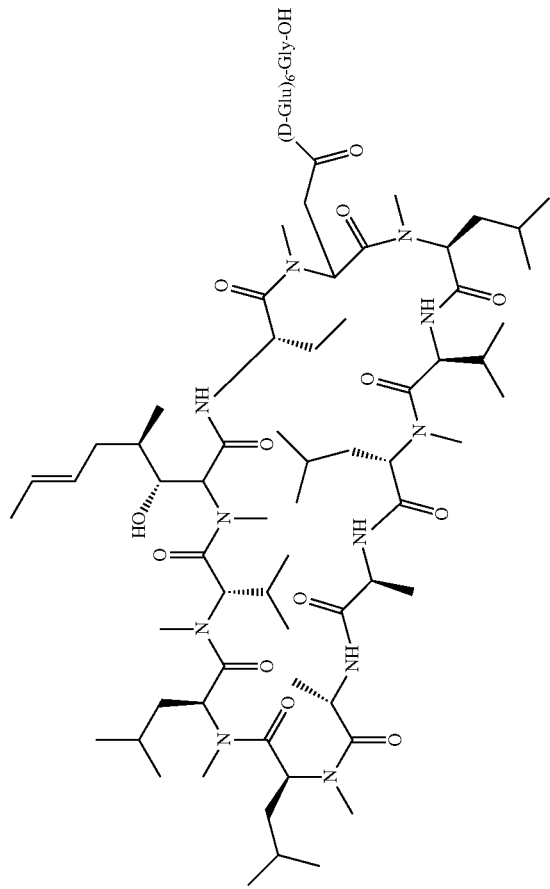
Cs-10M4
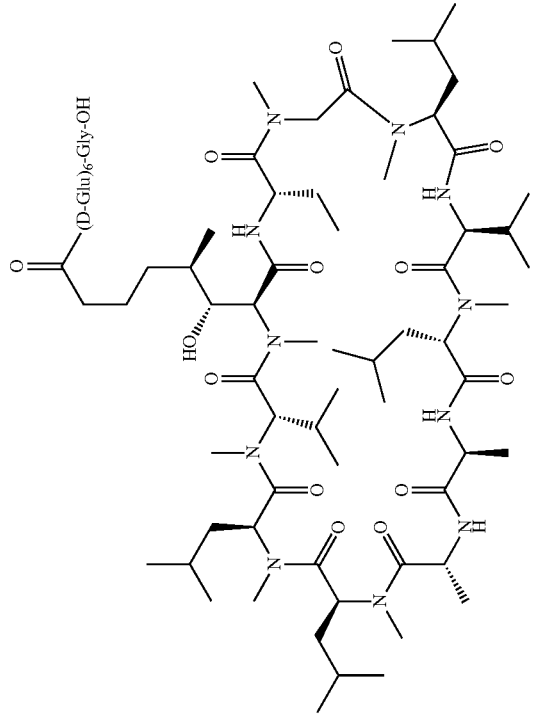

-continued
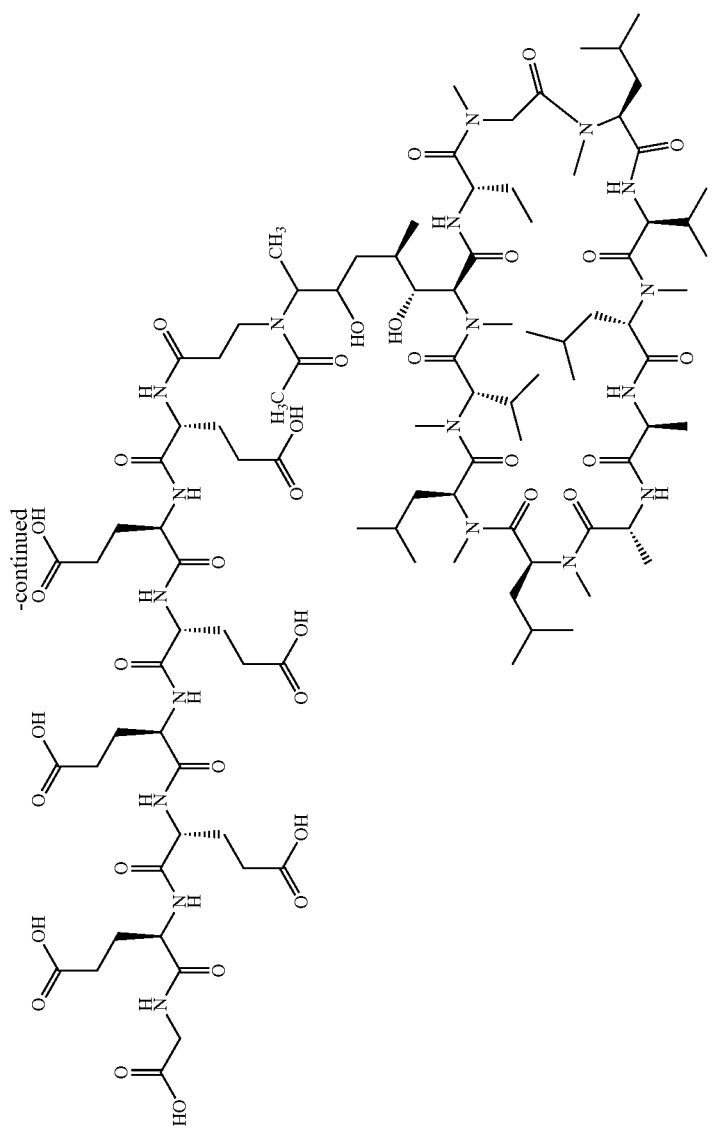
and

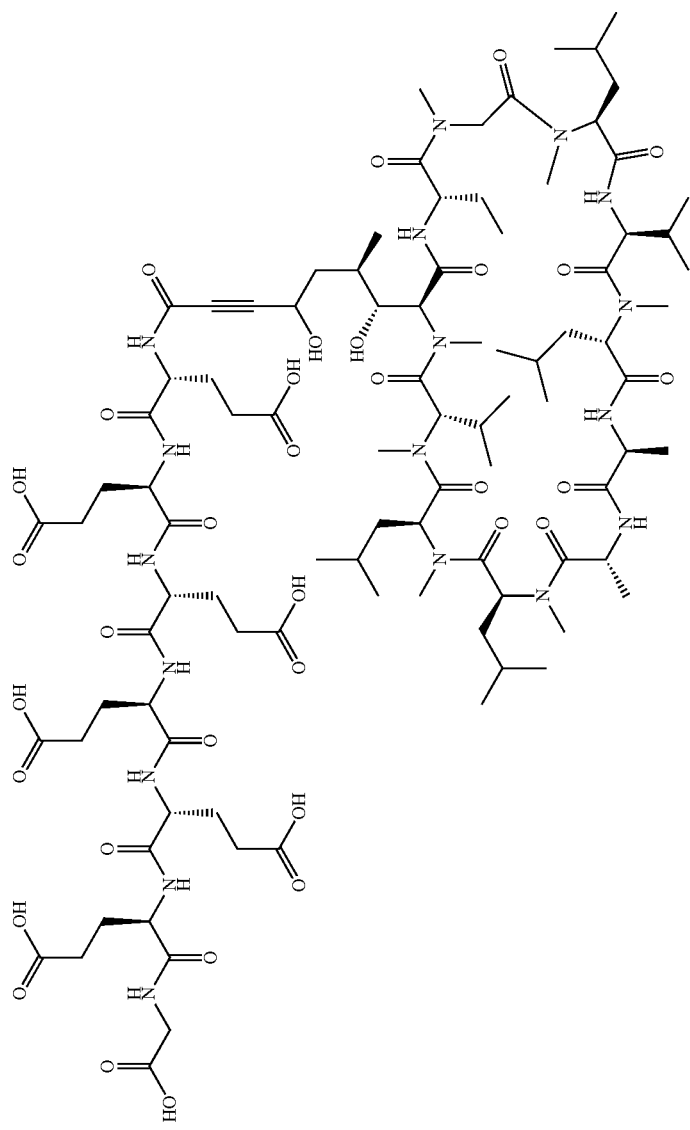
Cs-1Ad2

The present invention furthermore provides a method for concentrating a cyclosporin derivative in an extracellular space of a multicellular object, comprising the steps of:
- providing a cyclosporin derivative according to the invention;
- bringing the cyclosporin derivative into contact with a multicellular object.

By an "extracellular space" are meant all the areas which are located outside the cytosol and the membrane surrounding the cytosol. This also includes the culture solution present for example in cell suspensions.

The multicellular object can be any object which consists of at least two identical or different biological cells. The term "biological cell" covers human, animal and also vegetable and bacterial cells as well as monocellular creatures. If the biological cells are bacterial cells or monocellular creatures, then by the term "multicellular object" is meant a collection of several cells, such as for example a cell colony of a bacterial culture. If the biological cells are human or animal cells, then by the term "multicellular object" is meant a separated body part, such as for example a transplant, in particular an organ, cell, limb or tissue transplant, blood or a blood fraction, such as for example blood plasma or an in-vitro culture of human and/or animal cells, such as for example a two-dimensional tissue culture or a spheroid culture of the cells. If the biological cells are plant cells, then by the term "multicellular object" is meant a part of a plant, such as for example leaves, root or stalk or also a whole plant.

According to a preferred embodiment of the method according to the invention, the multicellular object is a separated organ or body part, blood or a blood fraction, a cell culture or a plant.

The present invention furthermore provides the use of a cyclosporin derivative according to the invention as medicament.

The fields of application of the medicament according to the invention can be the therapy and diagnosis of diseases but also cosmetic in nature, wherein by therapy is meant in the broadest sense also the control of pests in the animal and plant kingdom or the support of healing processes in the animal and plant kingdom but also the influencing of biological processes in the desired manner. Particular advantages lie in veterinary and human medicine, in particular in the application of substances on or in cell suspensions, tissue cultures, transplants or the whole mammal.

The present invention furthermore provides the use of a cyclosporin derivative according to the invention to produce a medicament for the treatment of a chronic inflammatory disease.

According to a preferred embodiment of the use according to the invention, the chronic inflammatory disease is asthma, rheumatoid arthritis, multiple sclerosis, psoriasis or ulcerative colitis.

Finally, the present invention furthermore provides a pharmaceutical composition which comprises a cyclosporin derivative according to the invention.

The pharmaceutical composition according to the invention can be any pharmaceutical composition known to a person skilled in the art to be suitable. For example the cyclosporin derivative according to the invention can be used in a form, selected from the group consisting of injections, infusions, tablets, creams, sprays, capsules, syrups, emulsions, powders, dry chemicals, suppositories or the like.

In a preferred embodiment the pharmaceutical composition is used in the form of sprays or tablets.

Within the framework of the present invention, the cyclosporin derivative can furthermore comprise groups which provide the cyclosporin derivative with further properties which are desirable for the respective intended use for a person skilled in the art. The cyclosporin derivative according to the invention can be bonded to one, but also to more than one, group which can be either identical, similar or different. The inclusion of additional groups in the cyclosporin derivative according to the invention can serve on the one hand to reinforce already-present properties, but on the other hand it is also possible to provide the cyclosporin derivative with new, further properties. It is for example conceivable that the cyclosporin derivative is provided with an indicator in order to monitor its concentration in the desired tissue or in order to be able to classify the desired tissue by means of indicator distribution. It is further conceivable that the cyclosporin derivative is provided with a group which makes possible its concentration in quite specific tissues.

In a preferred embodiment, the cyclosporin derivative therefore comprises an indicator which can in particular be covalently bonded to the cyclosporin derivative. In principle the indicator can, however, be bonded to the cyclosporin derivative in any manner known to a person skilled in the art to be suitable for the purpose according to the invention.

The term "indicator" includes, within the meaning of the invention, substances such as e.g. dyes, voltage-sensitive indicators, pH-sensitive indicators, calcium-sensitive indicators, radioactive elements, NMR labels or else also electron-spin labels and these are repeatedly described in the scientific literature (US 2005/0048671, EP 0649022, U.S. Pat. No. 6,596,499, U.S. Pat. No. 7,090,995, U.S. Pat. No. 4,672,044). The term indicator covers, within the meaning of the invention, individual atoms or molecules which are covalently bonded to the cyclosporin derivative. An indicator or also several indicators can be covalently bonded directly to the cyclosporin derivative. The term "indicator" preferably covers dyes, voltage-sensitive indicators, pH-sensitive indicators, radioactive elements, calcium-sensitive indicators, NMR labels and electron-spin labels.

"Dyes" within the meaning of the invention are substances which can be visually detected by detecting the electromagnetic radiation emitted from or not absorbed by them. These include e.g. dyes such as fluorescein isocyanate (FIC), fluorescein isothiocyanate (FITC), dimethylaminonaphthalene-S-sulfonyl chloride (DANSC), tetramethylrhodamine isothiocyanate (TRITC), lissamine rhodamine-B200-sulfonyl chloride (RB 200 SC), etc. A description of a number of suitable molecules can be found e.g. in DeLuca, "Immunofluorescence Analysis", in "Antibody As A Tool", Marchalonis et al., Ed., John Wiley & Sons, Ltd., pages 189-231, (1985).

"Voltage-sensitive indicators" within the meaning of the invention are substances which, depending on an adjacent electric potential difference or the existing electric potential, change their physical, optical or catalytic properties such that these trigger a detectable signal. Voltage-sensitive indicators such as e.g. DIBAC (Japanese Journal of Pharmacology 86 (2001), 342-350, American Journal of Physiology—Heart & Circulatory Physiology 287 (2004), H985-H993) are known to a person skilled in the art.

"pH-sensitive indicators" within the meaning of the invention are substances which, depending on the pH, change their physical, optical or catalytic properties such that these trigger a detectable signal. Such indicator dyes, such as e.g. phenol red, bromothymol blue, bromophenol blue, etc. are known to a person skilled in the art.

"Calcium-sensitive indicators" within the meaning of the invention are substances which, in the presence of calcium, change their physical, optical or catalytic properties such that these trigger a detectable signal. Calcium-sensitive indicators known to a person skilled in the art are e.g. aequorin and other calcium-sensitive dyes, such as e.g. FURA-2.

"Radioactive elements" within the meaning of the invention produce e.g. gamma radiation, such as e.g. the following isotopes $^{124}J$, $^{125}J$, $^{128}J$, $^{131}J$, $^{132}J$ or $^{51}Cr$, wherein $^{125}J$ is particularly preferred. Others, such as e.g. $^{11}C$, $^{18}F$, $^{15}O$ or $^{13}N$, can be detected by means of their positron radiation and corresponding detectors (positron-emission tomography) and others, such as e.g. $^{111}In$, can be detected by means of electron capture.

"NMR labels" within the meaning of the invention are substances in which atoms with an odd number of nucleons (sum of the protons and neutrons) are contained. Such atomic nuclei, such as e.g. $^{13}C$, $^{15}N$ or $^{19}F$, have a nuclear spin and thus a nuclear magnetic moment.

"Electron-spin labels" serve, within the meaning of the invention, to measure "electron paramagnetic resonance" by means of electron-spin resonance. The resonant microwave absorption of a sample is measured in an external magnetic field. Thus molecules can be detected which have a permanent magnetic moment (unpaired electrons) (Physics in Medicine & Biology 43 (1998), U 3-U 4, Clinical Chemistry & Laboratory Medicine 46 (2008), 1203-1210).

The cyclosporin derivative according to the invention can contain one or also more than one indicator which can be identical but also different in nature.

The use of indicators is particularly advantageous if the cyclosporin derivative according to the invention is to be used for the preparation of a medicament for use in a therapeutic process such as, for example, a diagnostic procedure (e.g. anamnesis investigation, physical examination, use of imaging processes such as X-ray/MRT or analysis with laboratory values of blood and other bodily fluids). If the cyclosporin derivative according to the invention also contains one or more indicators, the distribution space of the cyclosporin derivative can be perceived using these indicators. Indicators can also be used to quantify the cyclosporin derivative.

In a further preferred embodiment, the cyclosporin derivative according to the invention is also free from a protease interface, such as an amino acid linker, which can for example serve to bond the individual groups. If individual groups are not bonded directly, but via a splittable linker, this could, under certain circumstances—for example an unintended side-effect when administering several medicaments—lead to an unintended cleavage and thus to the loss of the group bonded via the linker in each case.

BRIEF DESCRIPTION OF THE DRAWINGS

The present invention will now be described in more detail with the help of the following examples and figures. The examples and figures have a purely illustrative character and in no way limit the scope of the present invention.

There are shown in.

DESCRIPTION OF THE PREFERRED EMBODIMENTS OF THE INVENTION

EXAMPLES

Example 1

Synthesis of Cs-1H1

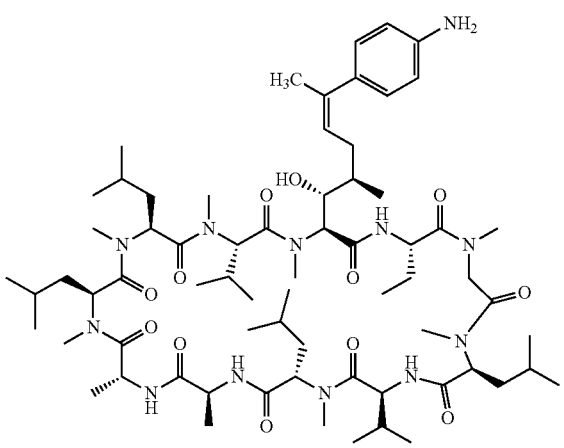

Cs-1H1

Figure 1:
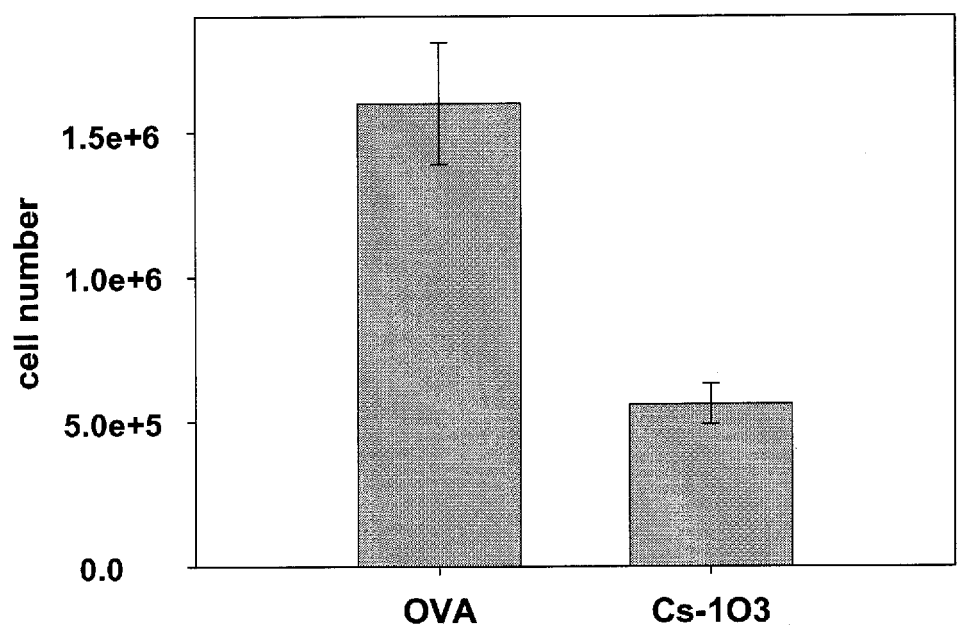
FIG. 1 the influence of Cs-103 on the number of CD4-positive T cells which migrated through ovalbumin sensitization into the bronchial lining.

100 mg CsA (0.075 mmol) was dissolved in 11 ml of a mixture of DMF/H$_2$O/Et$_3$N in the ratio 8:1:1 under protective gas (argon). Then, 0.4 equivalents each of Pd(OAc)$_2$, PPh$_3$ and Bu$_4$NCl and 20 equivalents of p-bromoaniline were added. After heating the mixture at 103° C. for 5 hours, the mixture was cooled to room temperature and 0.5 equivalents of AcOEt were added. The reaction mixture was then washed three times with saline solution. Then, the AcOEt fraction was filtered over MgSO$_4$ and evaporated under vacuum. The product was separated from impurities by means of preparative HPLC.

Example 2

Synthesis of Cs-1WZ2

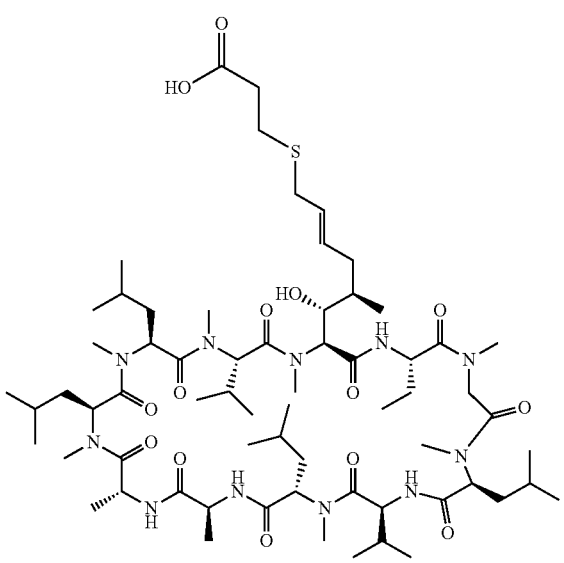

Cs-1WZ2

O-acetyl-CsA was synthesized according to the instruction by R. Traber et al. (Helv. Chim, Acta 1982, 65, 1655-1677). 50 mg O-acetyl-CsA was dissolved in 20 ml $CCl_4$. A catalytic quantity of AIBN and 1 equivalent of NBS were then added. Then, the mixture was kept under reflux for two hours. The solvent was then evaporated and the residue was taken up with 100 ml AcOEt. Then, the AcOEt solution was washed successively with 5% $KHSO_4$ solution, saturated $NaHCO_3$ solution and saline solution and then dried over $MgSO_4$. After filtering off and evaporation under vacuum, the residue was taken up in a solution of 3 equivalents of methyl-3-mercaptopropionate and 5 equivalents of diisopropylethamine, after which 5 ml DMF was added. Then, stirring was carried out for three hours at room temperature. DMF was then removed under vacuum and 5 ml 0.1 M LION in 50% methanol was added to the residue. After three hours, the reaction was brought to pH 2.5 by means of HCl and the product was then isolated by means of preparative HPLC.

Example 3

Synthesis of Cs-1A02

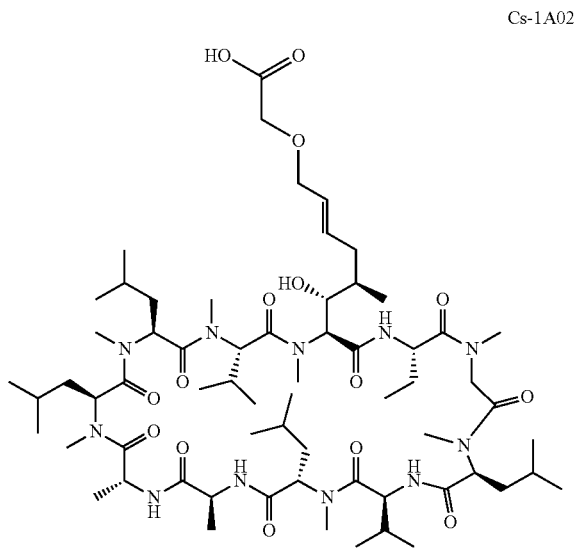 [SMILES: CC[C@@H]1NC(=O)[C@H]([C@H](O)[C@H](C)C/C=C/COCC(=O)O)N(C)C(=O)[C@H](C(C)C)N(C)C(=O)[C@H](CC(C)C)N(C)C(=O)[C@H](CC(C)C)N(C)C(=O)[C@@H](C)NC(=O)[C@H](C)NC(=O)[C@H](CC(C)C)N(C)C(=O)[C@H](C(C)C)NC(=O)[C@H](CC(C)C)N(C)C(=O)CN(C)C1=O]

Cs-1A02

60 mg of the precursor Cs-1A01 was produced according to the instruction by Eberle et al. (J. Org. Chem. 1992, 57, 2689). Then, the product was taken up with a solution of 20 mg butyl bromoacetate and 5 mg benzyltriethylammonium chloride in 1 ml dichloromethane, mixed with 2 ml 30% NaOH solution and stirred for two hours at room temperature. After dilution with 10 ml water, the product was extracted twice with ether. After drying of the organic phase by means of $MgSO_4$ and filtration, evaporation was carried out under vacuum and the residue was mixed with 5 ml 0.1 M LiOH in 50% methanol and stirred for three hours at room temperature. After acidification to pH 2.5 by means of HCl, the product Cs-1A02 was isolated by means of preparative HPLC.

Example 4

Production of Cs-101

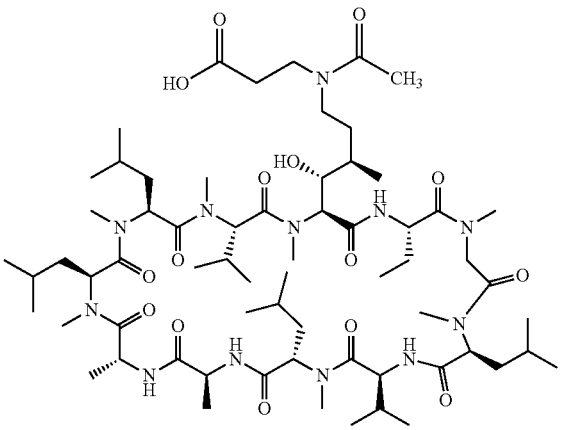

Cs-101

150 mg of the starting product O-acetyl-CsA-aldehyde was produced according to the instructions by J. Liu et al. (Anal. Biochem 2006, 356, 100-107) and then mixed with 250 mg H-β-Ala-OH in 30 ml methanol. After mixing for 10 minutes, 8.5 mg $NaBH_3CN$, dissolved in 500 μl methanol, was added and stirring was carried out overnight. After lowering the pH to approximately 1.5 with HCl, the methanol was evaporated under vacuum and the residue was taken up in saline solution and the obtained mixture extracted three times with AcOEt. Then, it was washed with 5% $KHSO_4$ solution, saturated $NaHCO_3$ solution and saline solution. After drying over $MgSO_4$ and filtering, drying was carried out under high vacuum. The residue was then taken up in a mixture, consisting of 15.4 μl AcOH, 104 mg HATU and 145 μl DIPEA, and 1 ml DMF. After mixing for two hours at room temperature, AcOEt was added and the mixture was washed twice successively with saturated $NaHCO_3$, 5% $KHSO_4$ and saline solution. After drying with $MgSO_4$ and filtering, the solvent was evaporated under vacuum. The residue was taken up in 3 ml THF, mixed with 3 ml 0.2 M LiOH, and stirred for 4 hours. After acidification to a pH of approximately 1.5 with HCl, the product was able to be isolated by means of preparative HPLC.

Example 5

Production of Cs-106

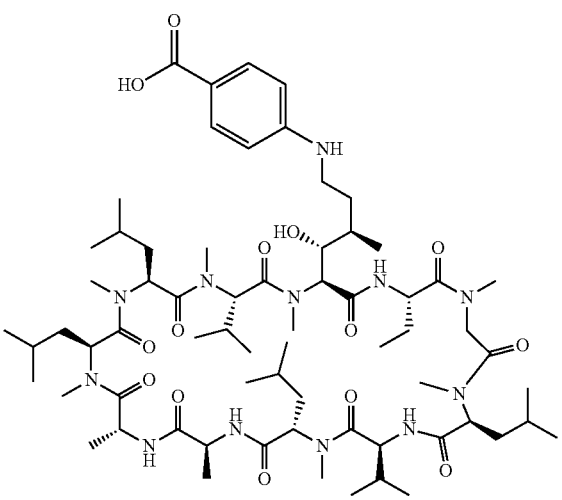

Cs-106

40 mg of the starting product O-acetyl-CsA-aldehyde was produced according to the instruction by J. Liu et al. (Anal. Biochem. 2006, 356, 100-107) and then dissolved in 10 ml methanol. 22 mg 4-aminobenzoic acid and 3 mg NaBH$_3$CN were then added to the solution. After stirring overnight at room temperature, the solution was adjusted to a pH of 1.5 by means of HCl. Then, the methanol was evaporated and the residue was taken up with saline solution. Extraction was then carried out three times with AcOEt and the combined extracts were washed successively with 5% KHSO$_4$, saturated NaHCO$_3$ and saline solution. After drying over MgSO$_4$ and filtering, evaporation was carried out under vacuum. The residue was taken up in a mixture of 3 ml THF and 3 ml 0.2 M LiOH and stirred for 4 hours. After acidification to a pH of approximately 1.5 by means of HCl, the product was isolated by means of preparative HPLC.

Example 6

Production of Cs-1011

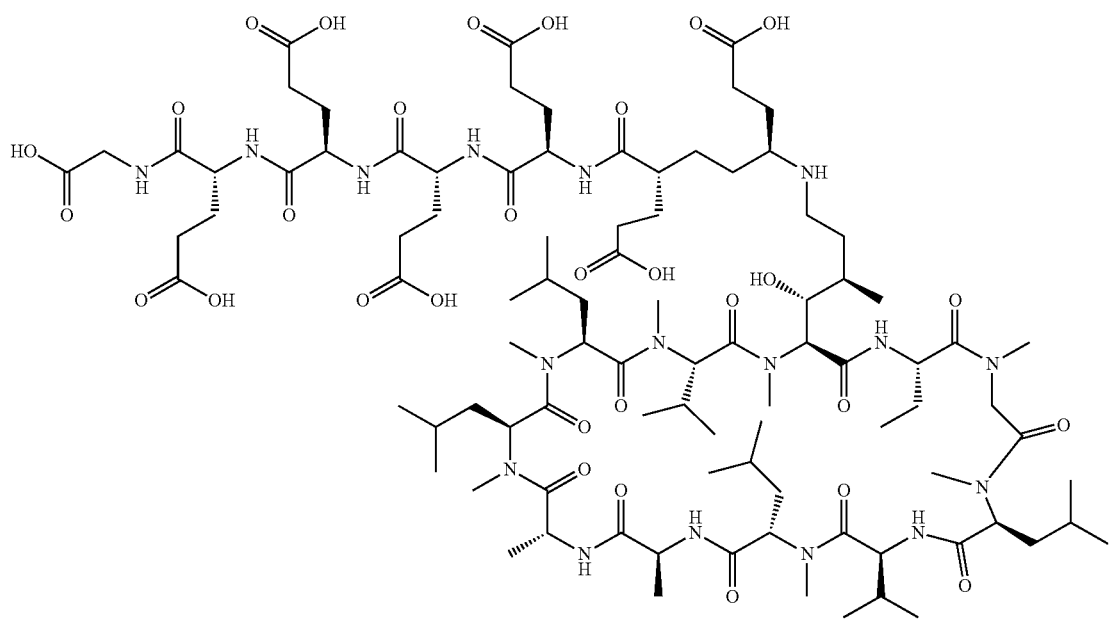

Cs-1011

40 mg of the starting product O-acetyl-CsA-aldehyde was produced according to the instruction by J. Liu et al. (Anal. Biochem. 2006, 356, 100-107) and then dissolved in 10 ml methanol. Then, 3 equivalents of H-(D-Glu)$_6$-Gly-OH (synthesized by means of solid-phase peptide synthesis, starting from D-Glu(Ot-Bu)-OH) and 3 mg NaBH$_3$CN, were added to the solution which was stirred overnight at room temperature. The solution was then adjusted to a pH of 1.5 by means of HCl. Then, the methanol was evaporated and the residue was taken up in a mixture of 3 ml THF and 3 ml 0.2 M LiOH. Then, stirring was carried out for 4 hours at room temperature. After acidification to a pH of approximately 1.5 by means of HCl, the product was isolated by means of preparative HPLC.

Example 7
Production of Cs-1S1

Cs-1S1

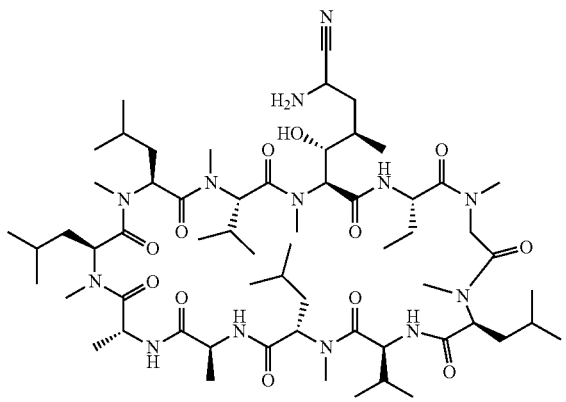

50 mg of the starting product O-acetyl-CsA-aldehyde was produced according to the instruction by J. Liu et al. (Anal. Biochem. 2006, 356, 100-107) and then dissolved in 2 ml methanol. Then, a solution of 3 mg NH$_4$Cl and 3 mg KCN, dissolved in 25% NH$_3$, was slowly added to the solution at 5° C. After 4 hours of stirring at room temperature, evaporation was carried out under vacuum and the product was isolated by means of preparative HPLC.

Example 8
Production of Cs-1Ad1

Cs-1Ad1

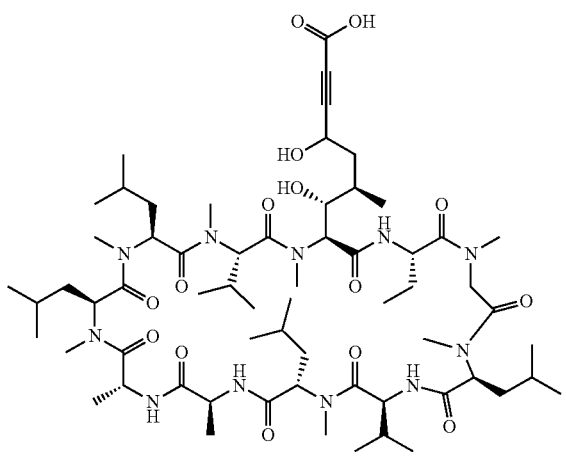

60 mg of the starting product O-acetyl-CsA-aldehyde was produced according to the instruction by J. Liu et al. (Anal. Biochem. 2006, 356, 100-107) and then dissolved in THF and cooled to −78° C. A mixture of diisopropylamine in THF and N-butyllithium was stirred separately for 30 min at −78° C. The two mixtures were combined at −78° C. and stirred until room temperature was reached. Then, the THF supernatant was removed under vacuum and the residue was taken up in AcOEt. The AcOEt extract was washed twice successively with 5% KHSO$_4$ solution, saturated NaHCO$_3$ solution and saline solution. After drying over MgSO$_4$ and filtering, evaporation was carried out under vacuum. The residue was taken up in a mixture of 3 ml THF and 3 ml 0.2 M LiOH and stirred for 4 hours. After acidification to a pH of approximately 1.5 by means of HCl, the product was isolated by means of preparative HPLC.

Example 9
Production of CsM4

CsM4

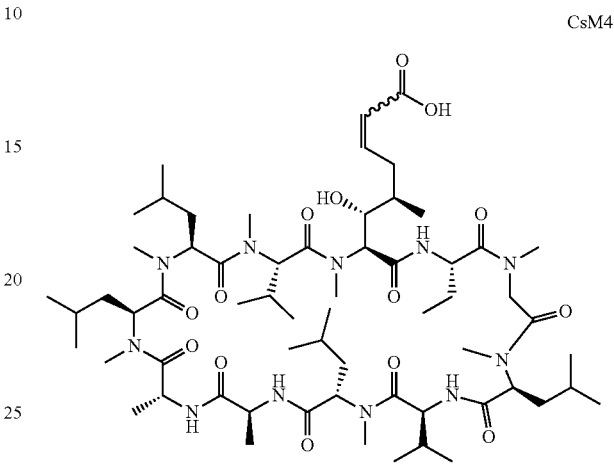

Cyclosporin A (CsA) was kept under reflux for 45 hours with 0.1 equivalents of Hoveyda-Grubbs catalyst ($2^{nd}$ generation) and 20 equivalents of diethyl maleate in toluene. After removal of the toluene under vacuum, the residue was dissolved in DCM/MeOH (10:0.5) and filtered through silica gel. After removal of the organic solvent under vacuum, the residue was dissolved in 5 ml THF and mixed with a 0.2 M LiOH solution. After stirring overnight and neutralization of the solution with HCl, the product was able to be separated off by means of preparative HPLC.

Example 10
Production of Cs-10M3

Cs-10M3

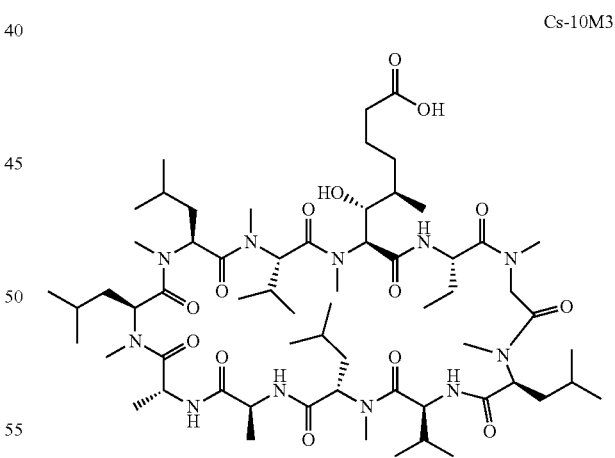

Cyclosporin A (CsA) was kept under reflux for 45 hours with 0.1 equivalents of Hoveyda-Grubbs catalyst ($2^{nd}$ generation) and 20 equivalents of diethyl maleate in toluene. After removal of the toluene under vacuum, the residue was dissolved in DCM/MeOH (10:0.5) and filtered through silica gel. After removal of the organic solvent under vacuum, the residue was dissolved in 5 ml methanol and palladium activated carbon catalyst was added under H$_2$. After completion of hydrogenation, filtering was carried out and 2 ml THF as well as 2 ml 0.2 M LiOH solution were added. After stirring overnight, neutralization with HCl was carried out and the product was separated off by means of preparative HPLC.

Example 11

Production of Cs-1E1

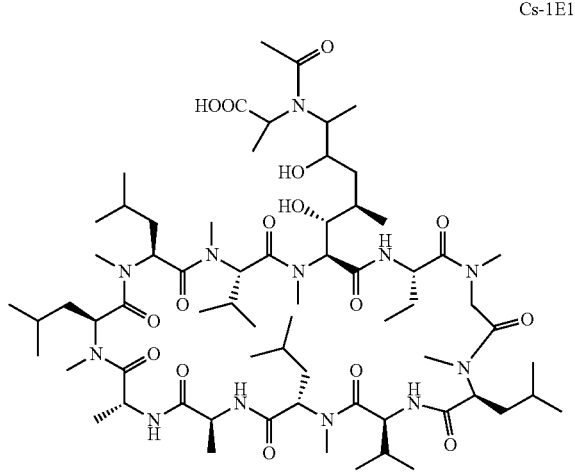 [SMILES: CC[C@@H]1NC(=O)[C@H]([C@H](O)[C@H](C)CC(O)C(C)N(C(C)=O)C(C)C(=O)O)N(C)C(=O)[C@H](C(C)C)N(C)C(=O)[C@H](CC(C)C)N(C)C(=O)[C@H](CC(C)C)N(C)C(=O)[C@@H](C)NC(=O)[C@H](C)NC(=O)[C@H](CC(C)C)N(C)C(=O)[C@H](C(C)C)NC(=O)[C@H](CC(C)C)N(C)C(=O)CN(C)C1=O]

Cs-1E1

O-acetyl-CsA was synthesized according to the instruction by R. Traber et al. (Helv. Chim. Acta 1982, 65, 1655-1677) and then dissolved in dichloromethane (DCM). After addition of 1.1 equivalents of m-chloroperbenzoic acid, stirring was carried out for two hours at room temperature. Then, the DCM was removed under vacuum and the residue was taken up with 10 equivalents of H-Ala-Ot-Bu and DMF and stirred at 50° C. for 5 hours. The DMF was then removed under vacuum and the residue was taken up with AcOEt. The AcOEt extract was washed twice successively with 5% KHSO$_4$ solution, saturated NaHCO$_3$ solution and saline solution. After drying over MgSO$_4$ and filtering, evaporation was carried out under vacuum and drying under high vacuum. The residue was then mixed with pre-activated acetic acid (three equivalents of acetic acid, three equivalents of HATU, 6 equivalents of DIPEA in DMF; activated for 5 minutes in total) and stirred for two hours at room temperature. DMF was then removed under vacuum and the residue was taken up with AcOEt. Then, the AcOEt extract was washed successively with 5% KHSO$_4$ solution, saturated NaHCO$_3$ solution and saline solution. After drying over MgSO$_4$ and filtering, evaporation was carried out under vacuum and drying under high vacuum. The residue was then stirred with 0.1 M LiOH until the end of the hydrolysis. The product was then isolated by means of preparative HPLC.

Example 12

Production of Cs-1H2

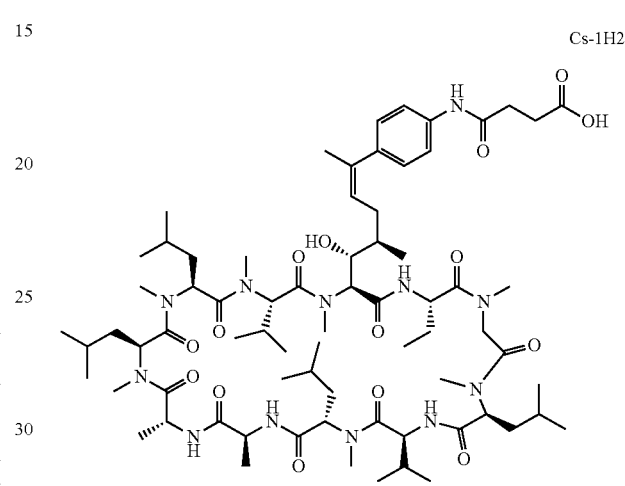

Cs-1H2

80 mg succinic anhydride and 223 µl triethylamine were added to a solution of 8 mg Cs-1H1 (Example 1) in 1 ml DMF. This mixture was stirred for two days at room temperature. The product Cs-1H2 was able to be isolated directly from the mixture by means of preparative HPLC.

Example 13

Production of Cs-1H2-2

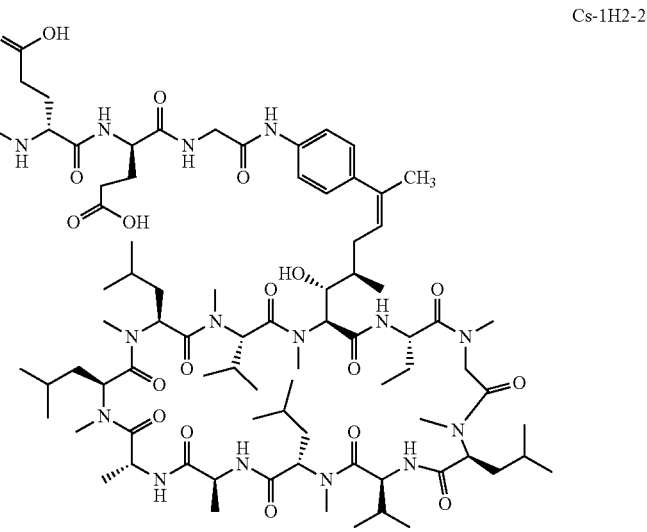

Cs-1H2-2

100 mg Ac-(D-Glu(OMe))$_6$-Gly-OH (synthesized by means of solid-phase peptide synthesis) was dissolved in 5 ml DMF and activated for 5 minutes with 1.1 equivalents of HATU and 3 equivalents of DIPEA. Then, Cs-1H1 (Example 1) was added. After stirring the mixture for two hours at room temperature, the solvent was removed under vacuum. 0.1 M LiOH, dissolved in 50% methanol, was added to the residue and mixed until the methyl ester was completely hydrolyzed. The end-product (Cs-1H2-2) was able to be obtained by means of preparative HPLC.

Example 14

The cyclosporin derivatives Cs-1E3, Cs-1S2 and Cs-109 shown below were also obtained using the method of Example 13, wherein other educts were used as appropriate:

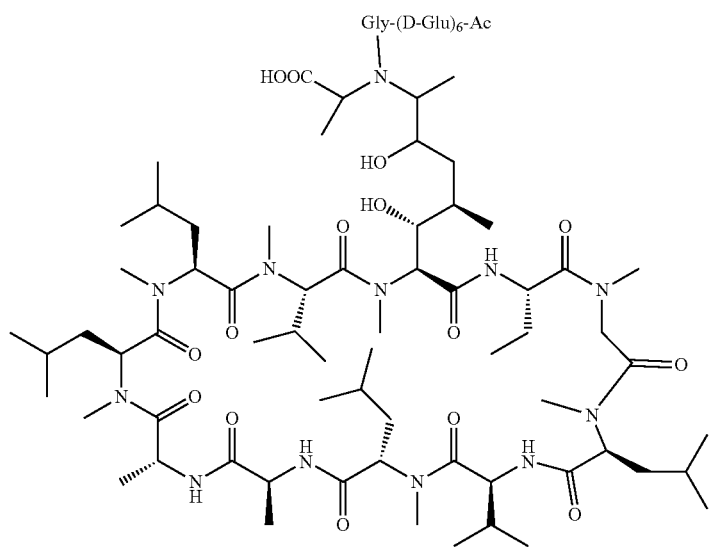

Cs-1E3

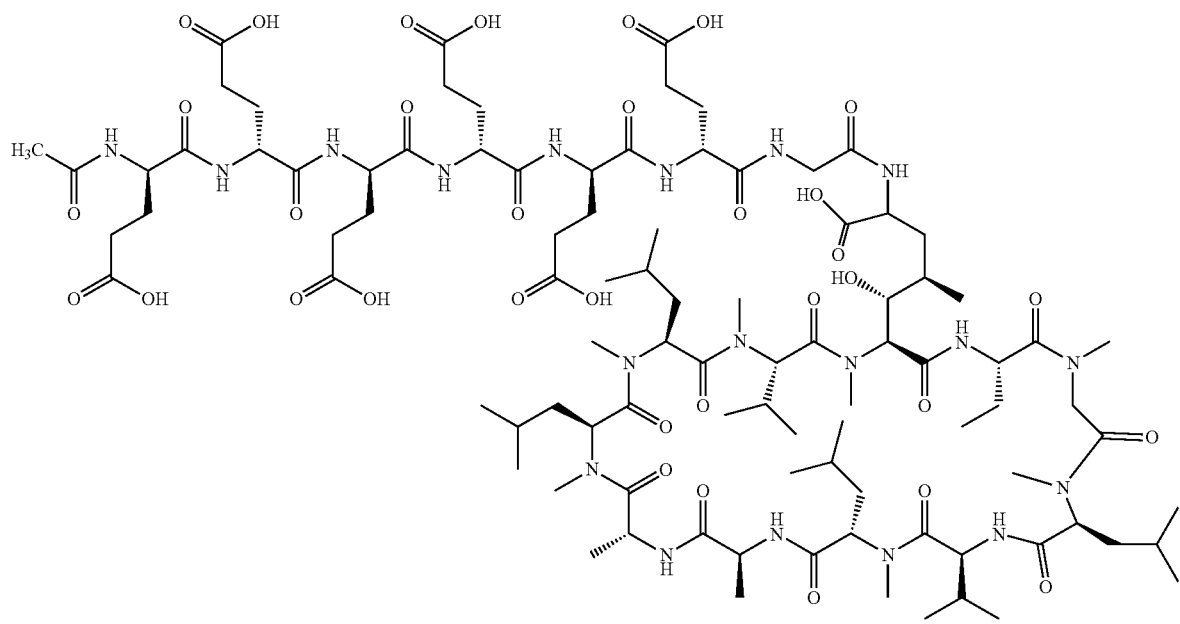

Cs-1S2

Cs-109
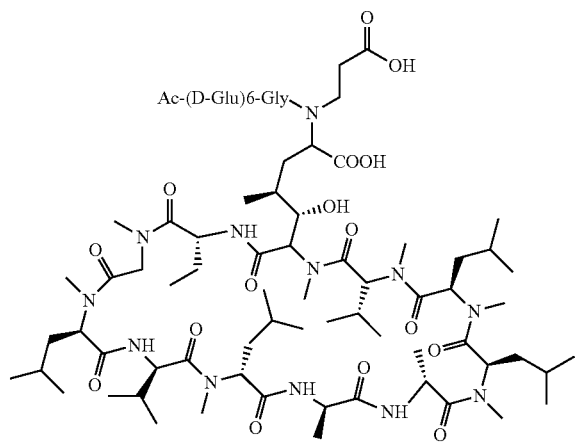
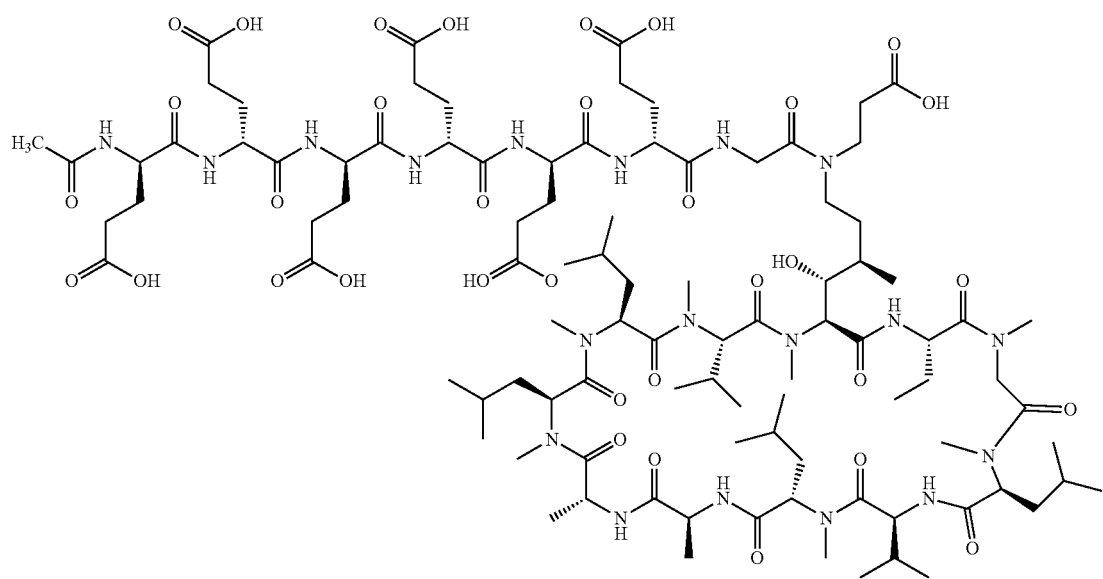
Cs-109

Example 15

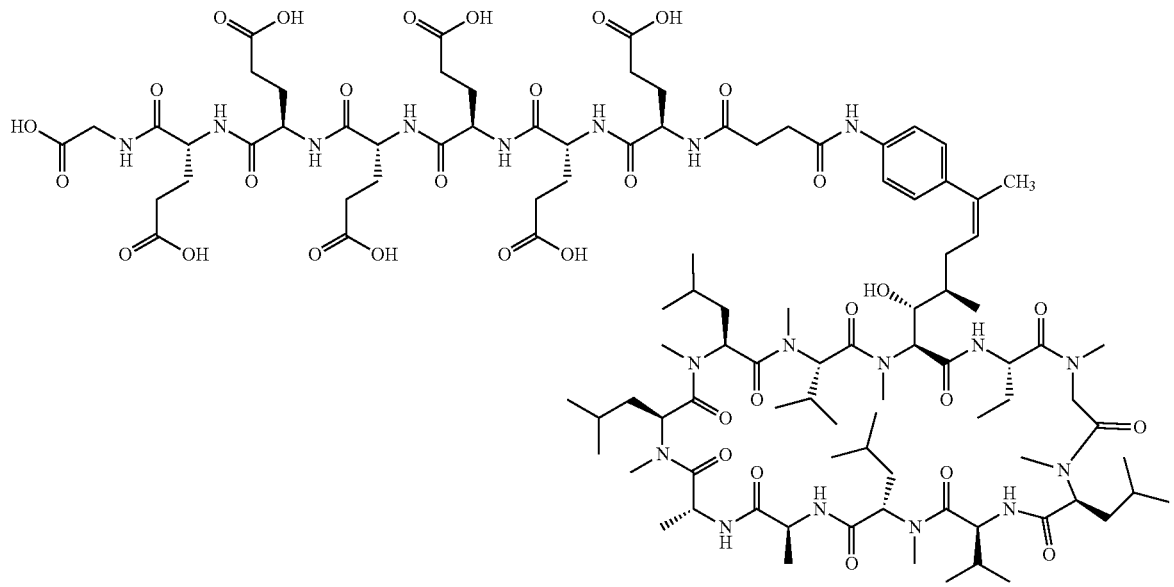

Cs-1H4

50 mg Cs-1H2 (Example 12), one equivalent of HATU and three equivalents of DIPEA in 3 ml DMF were stirred for 20 min at room temperature. Then, 1 equivalent of H-(D-Glu)$_6$-Gly-OH (synthesized by means of solid-phase peptide synthesis) dissolved in 2 ml DMF was added and the solution was stirred overnight. After filtering, the product was able to be isolated by means of preparative HPLC.

The cyclosporin derivatives Cs-1WZ3, Cs-1A03, Cs-103, Cs-107, CsM5, Cs-10M4, Cs-1E2, and Cs-1Ad2 shown below were also obtained using the method of Example 13, wherein other educts were used as appropriate:

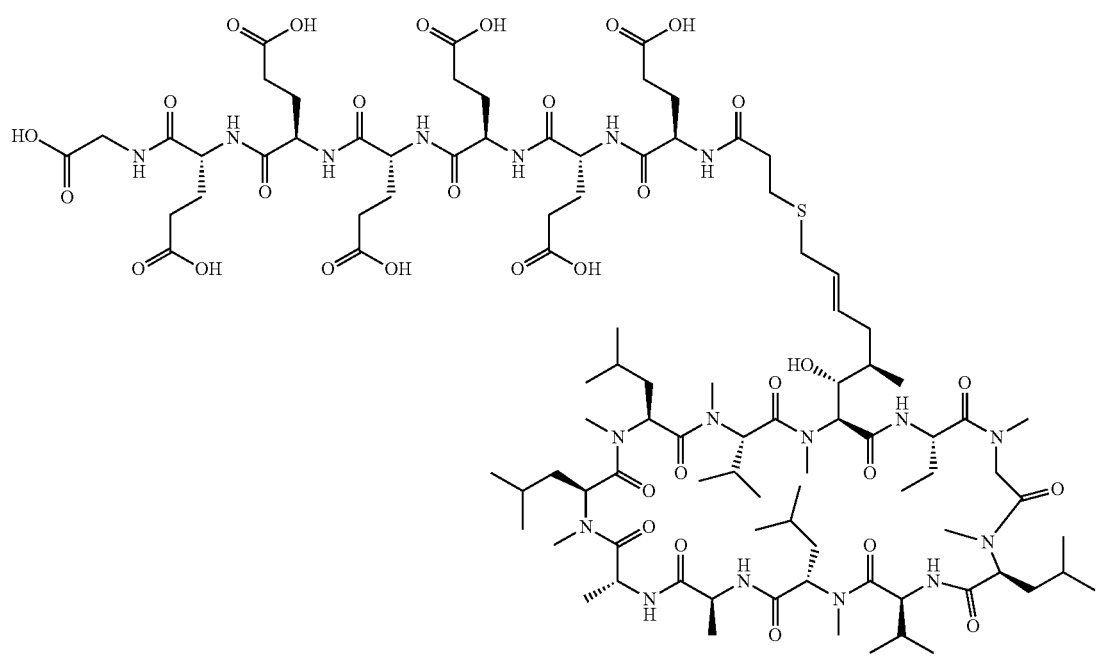

Cs-1WZ3

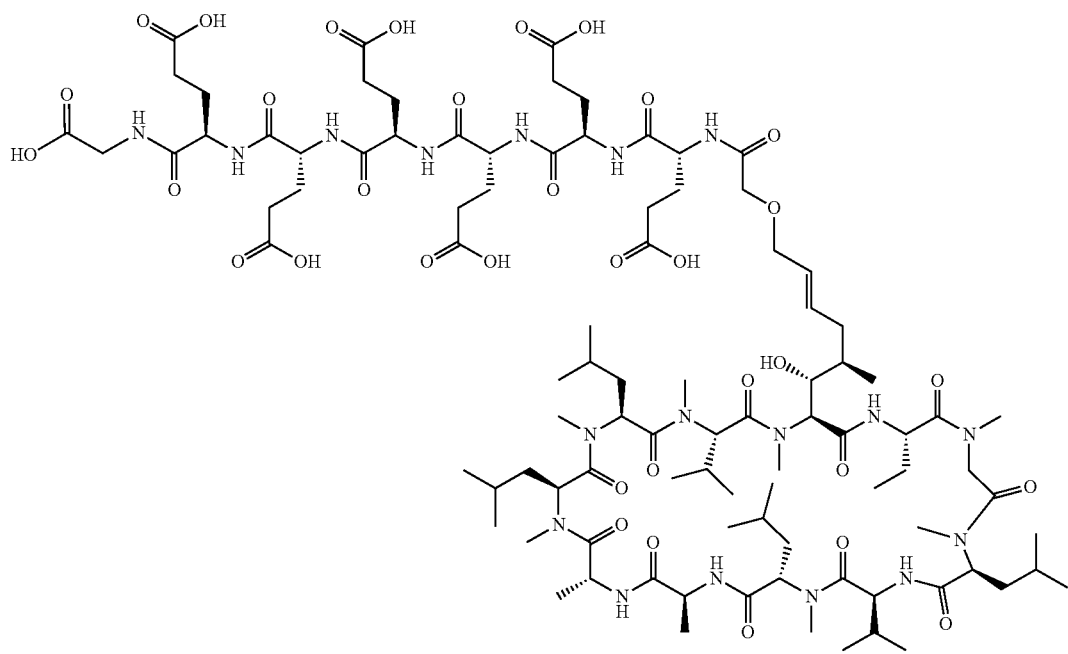
Cs-1A03
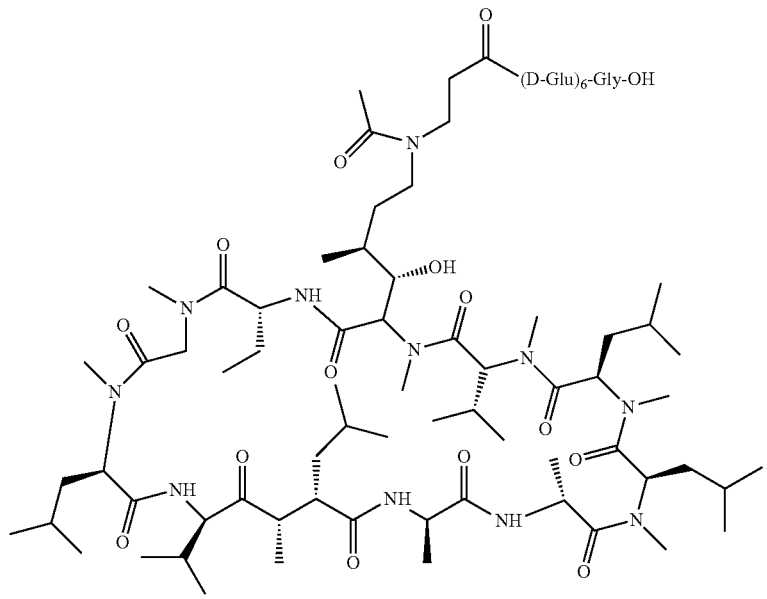
Cs-1O3

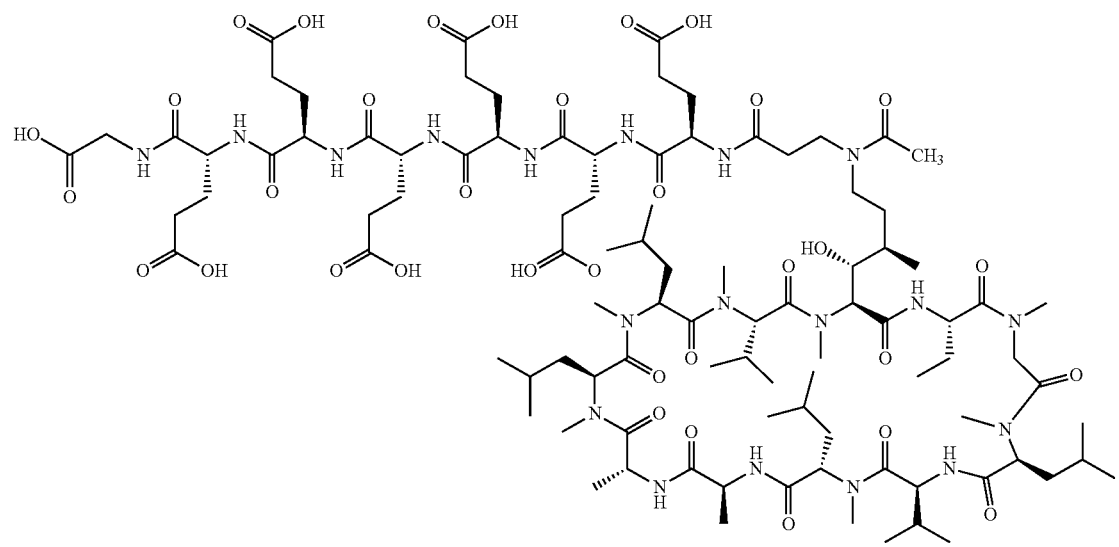
Cs-103
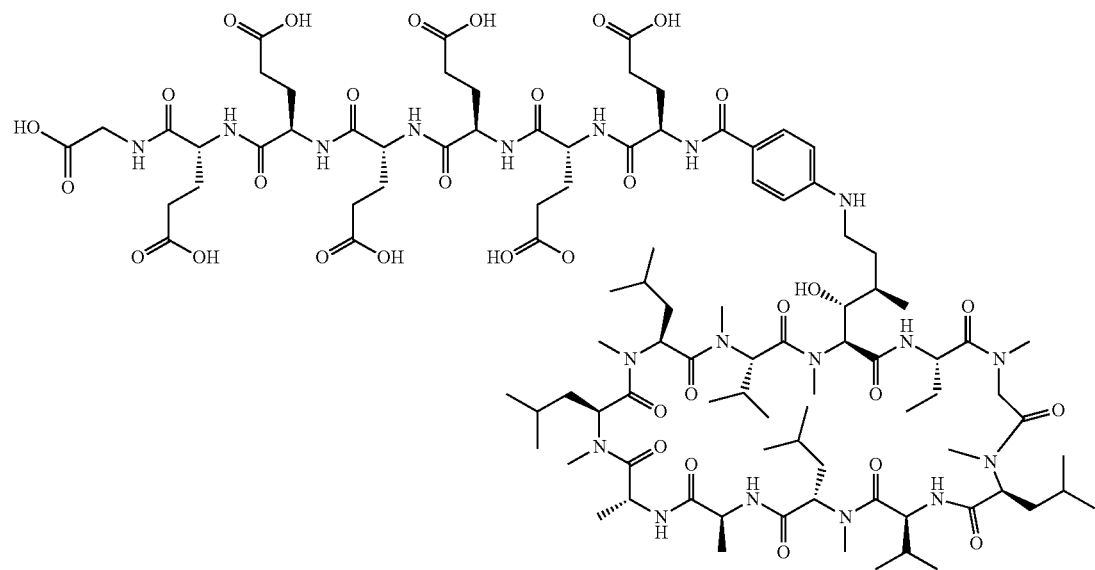
Cs-107

-continued
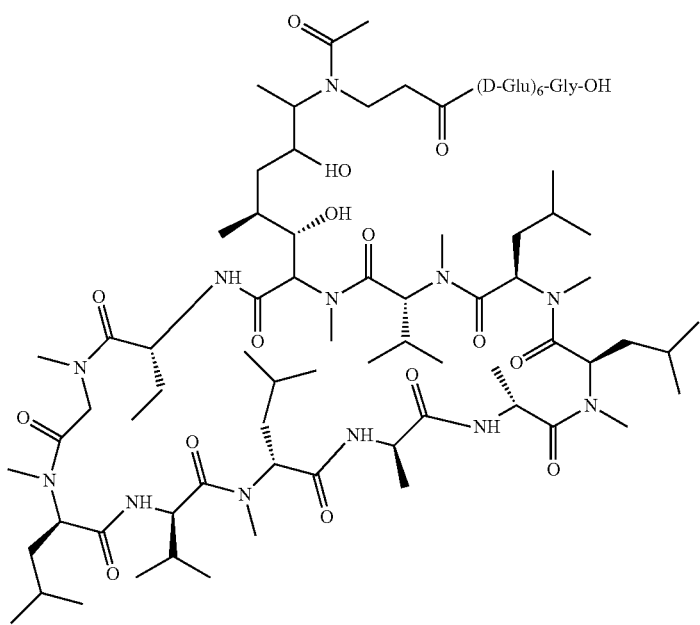
Cs-1E2
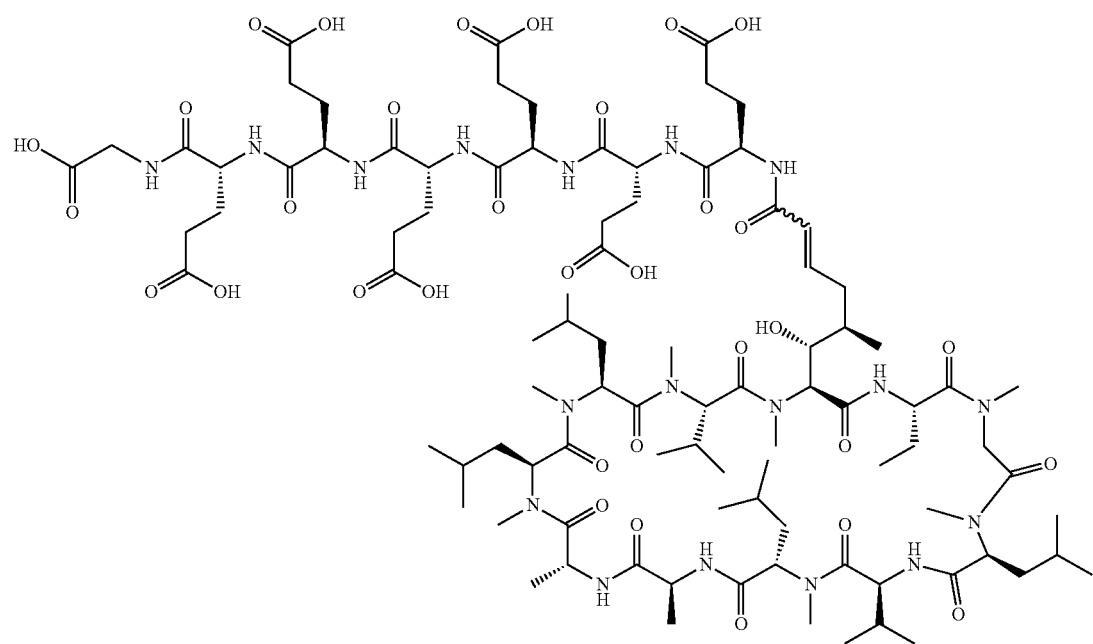
CsM5

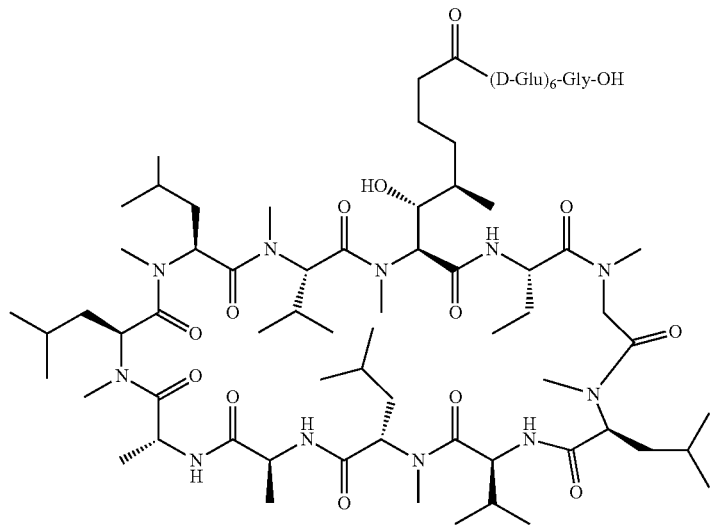
Cs-10M4
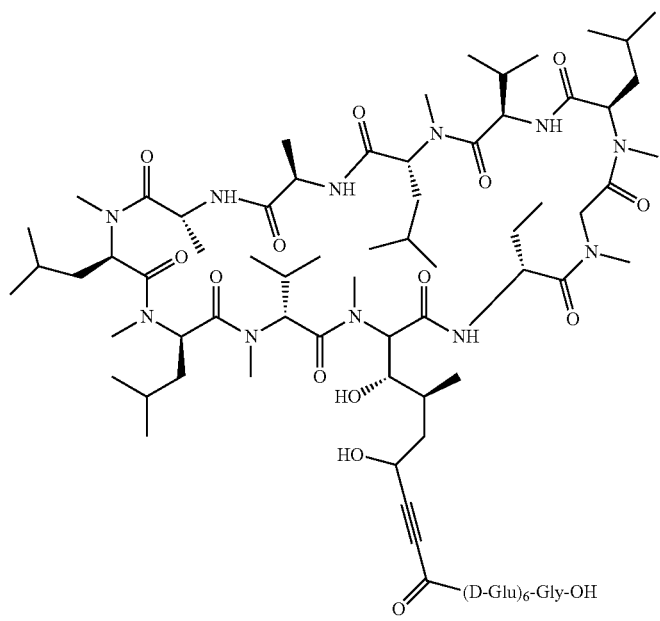
Cs-1Ad2

-continued

Cs-1E2

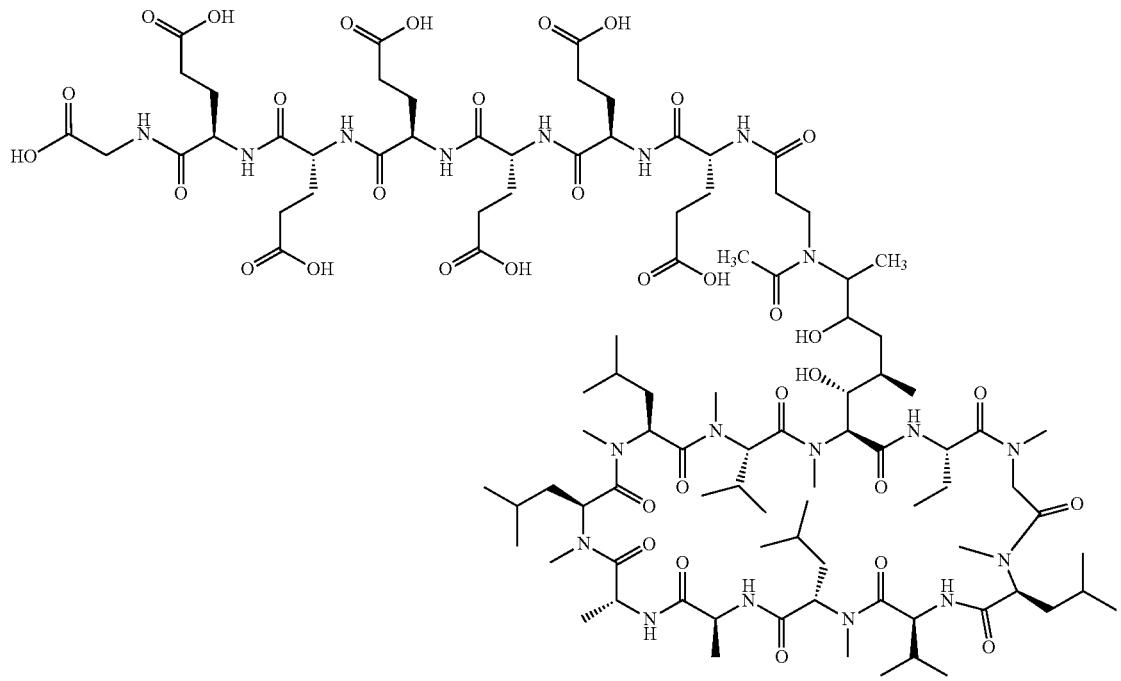

and

Cs-1Ad2

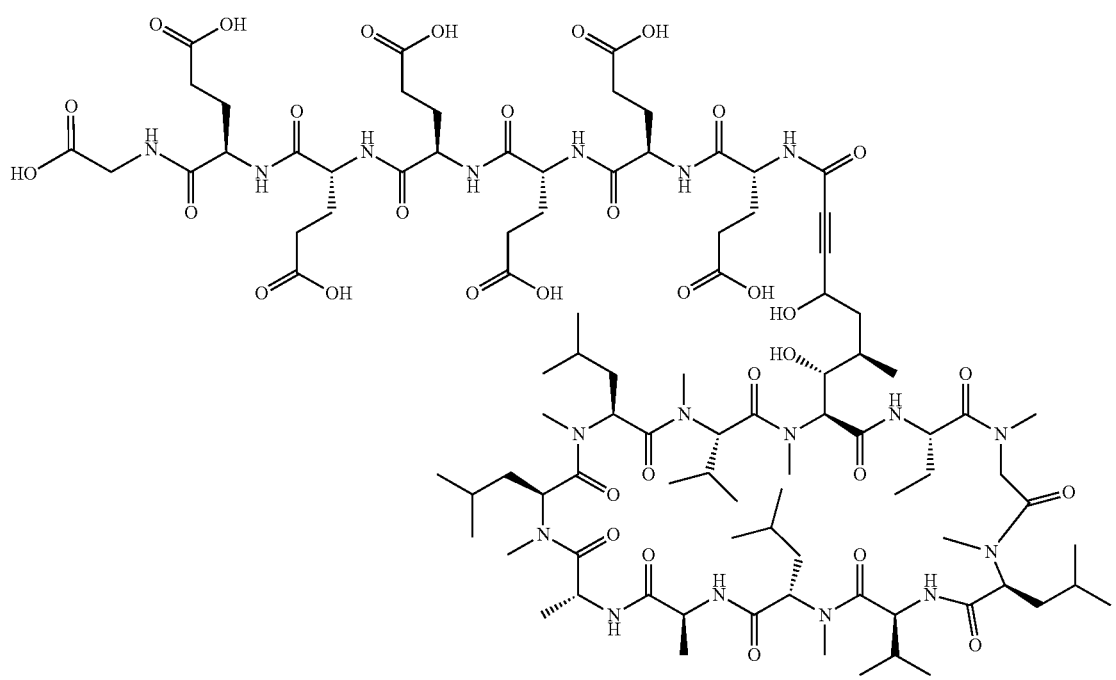

Example 16

Production of TAMRA-labelled Cs-101

16a
TAMRA-Labelled Trifunctional Linker MM-50

114 mg HATU, 154 µl DIPEA and 82 mg HOAt were added to a solution of 5(6)-carboxytamra (130 mg) in 5 ml DMF. The solution was then mixed for 20 minutes at room temperature and added to a solution of 200 mg of the trifunctional linker MM-50 (Malesevic M, Lücke C, Jahreis G (2005), Simple and efficient synthesis of new trifunctional templates). Peptides 2004, Proceedings of the Third International and Twenty-Eighth European Peptide Symposium, Kenes International, Israel, 391-392) in 5 ml DMF. After mixing the solution for two hours at room temperature and filtering, DMF was removed under vacuum. After separation of the product by means of RP HPLC a mass of 1105.2

[M+H]+ (theoretical: m/z calc. 1104.5) could be determined by means of MALDI mass spectrometry.

16b

Coupling of the TAMRA-Labelled Trifunctional Linker to Cs-101

50 mg Cs-101 (Example 4), one equivalent of HATU and three equivalents of DIPEA in 3 ml DMF were stirred for 20 min at room temperature. Then, 1 equivalent of the trifunctional linker dissolved in 2 ml DMF was added and the solution was stirred overnight. After filtering, the product was able to be isolated by means of preparative HPLC.

focussing aid, T-PFS, in order to prevent a so-called focus drift. An objective with phase contrast (40.0× Plan Fluor oil immersion NA 1.30) was used for the pictures, as well as the microscope's own software EZ-C1 3.7. The fluorophor 5-(6)-carboxytetramethylrhodamine was excited by a Melles & Griot 561 nm laser.

The cells were firstly washed twice with 2 ml PBS pH 7.4 (Dulbecco) and then taken up in 2 ml MIK medium (phenol red-free DME medium, FCS-free, with 20 mM HEPES pH 7.2 and 0.01% carbenicillin) and incubated for 20 min at 37° C. and 5% $CO_2$. During the taking of the pictures the cells

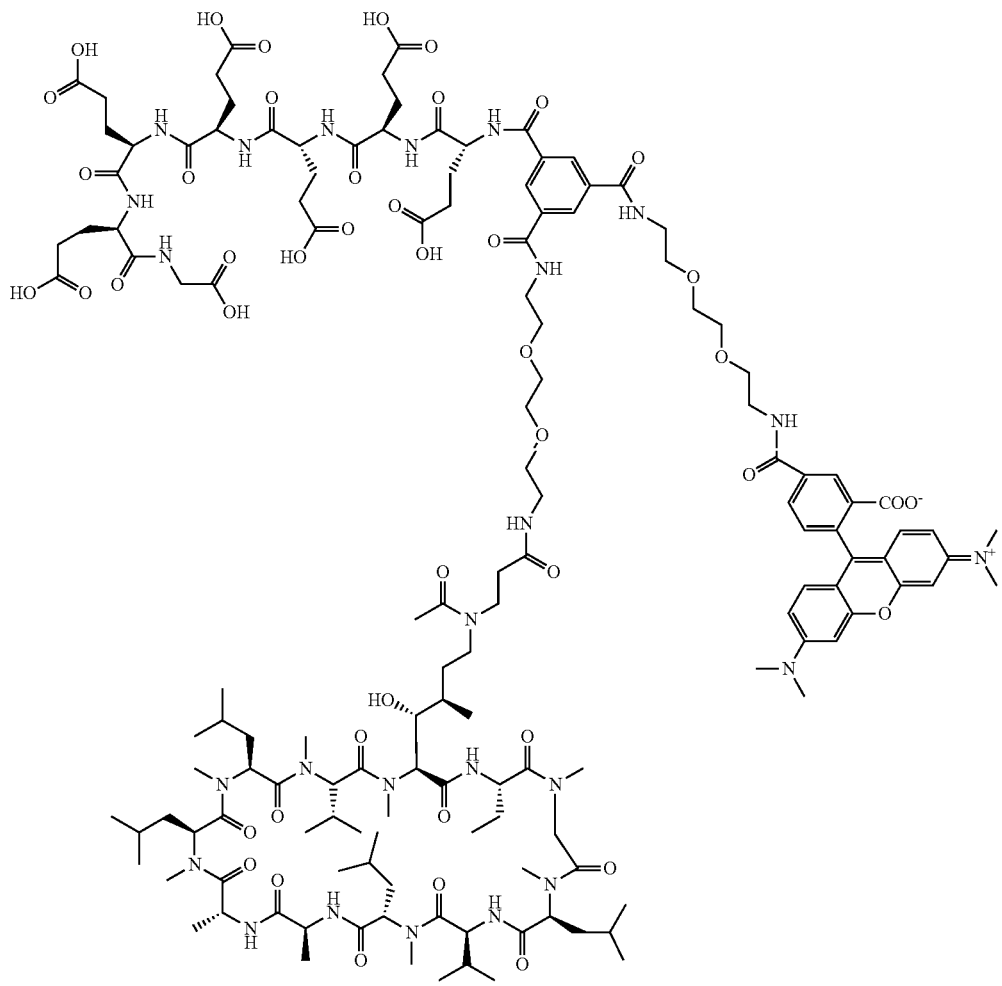

Example 17

Uptake of Chemically Modified CsA Compounds by Hela Cells

The advantage of the present discovery becomes clear upon investigating the behaviour during transport of the cyclosporin derivative TAMRA-Cs-1S2. The uptake of chemically modified, fluorescing CsA derivatives into living eukaryotic cells is shown on a cell line by means of confocal laser scan microscopy. For the experiment, $10^5$ Hela cells were sown in Ibidi® Petri dishes (μ-Dish, 35 mm, high) and incubated for 1-2 days in DME medium (high glucose) at 37° C. and 5% $CO_2$.

Examination was by means of an inverted microscope (Nikon ECLIPSE C1TE2000-E) which was equipped with a were in an incubator for microscopes (Stage Top Incubator INU series from Tokai Hit®) at 37° C. and 5% $CO_2$. The investigation was started by adding 250 nM CsA derivative dissolved in DMSO and diluted in MIK medium. In the fluorescence light the Hela cells are visible as fluorescent cells. The cyclosporin derivative provided with an acid peptide does not accumulate within the Hela cells.

Example 18 a) Preparation and Production of Mononuclear Mice Cells

A mouse spleen removed by surgery (BALE/c line) was crushed between two object glasses in order to prepare suitable cell suspensions. The thus-obtained suspension was then filtered through a nylon sieve in order to separate off coarse constituents. The thus-obtained cells were centrifuged together with a lymphocyte-separation medium (Mediatech) in order to obtain mononuclear cells. Cell cultures of these cells were then incubated in microtiter plates (8×12 cavities) at a cell density of $6 \times 10^5$ cells per cavity in EHAA medium/ 5% FCS (Click's medium) in the presence of 10 µg/ml concanavalin A (ConA) with 2 µM Cs-103, with unmodified cyclosporin A (Sigma) or with 1% ethanol (diluent). After a culture time of 48 hours 1 µCi 3H-thymidine was added per cavity and incubation continued for a further 6 hours. The cells of every cavity were then harvested (TomTec 96-well harvester) and the radioactivity of the cells was measured (Tri-Lux beta-plate counter).

b) Asthma Studies

An immune response to ovalbumin was provoked by administering ovalbumin together with aluminium hydroxide. The immune response can be tracked with the help of the T helper cells population (CD4+) which has migrated into the bronchial lining and the eosinophilic granulocytes which have migrated in.

Female mice (BALE/c line) were sensitized by intraperitoneal (i.p.) administration of 50 µg ovalbumin (OVA) dissolved in phosphate buffer (PBS) plus 100 µL aluminium hydroxide (alum) with a total volume of 200 µL per mouse on day 0.100 µg OVA in PBS (50 µL total volume) in each case was then administered intranasally to the OVA/alum-sensitized mice under mild anaesthesia (isoflurane) on days 7 to 10. From these animals groups were formed which additionally received on days 7, 9, and 11 either 250 µg Cs-103 in PBS (i.p.), PBS only (diluent) or no further addition (-). On day 12 all the animals were killed by $CO_2$ exposure and cells of the bronchial tract were obtained by bronchial lavage (BAL) by means of a cannula introduced into the trachea washing three times each with 1 ml cold PBS. The obtained cells of the BAL were then double dyed (a) with Cy-Chrome-conjugated anti-mouse CD4-antibodies and (b) with FITC-conjugated anti-mouse CD62L-antibodies. The cells were then analyzed by means of FACS. Effector/Memory CDC T cells were distinguished as $CD4^+/CD62L^-$ lymphocytes and eosinophilic cells with the help of their scattered light properties (FSC/SSC). The results are summarized in FIGS. 1 to 3.

FIG. 1 shows the influence of Cs-103 on the number of CD4-positive T cells which migrated through ovalbumin sensitization into the bronchial lining. The animals sensitized with OVA served as control. It can be seen from FIG. 1 that the administration of Cs-103 very significantly reduced the number of CD4-positive T cells.

Figure 2:
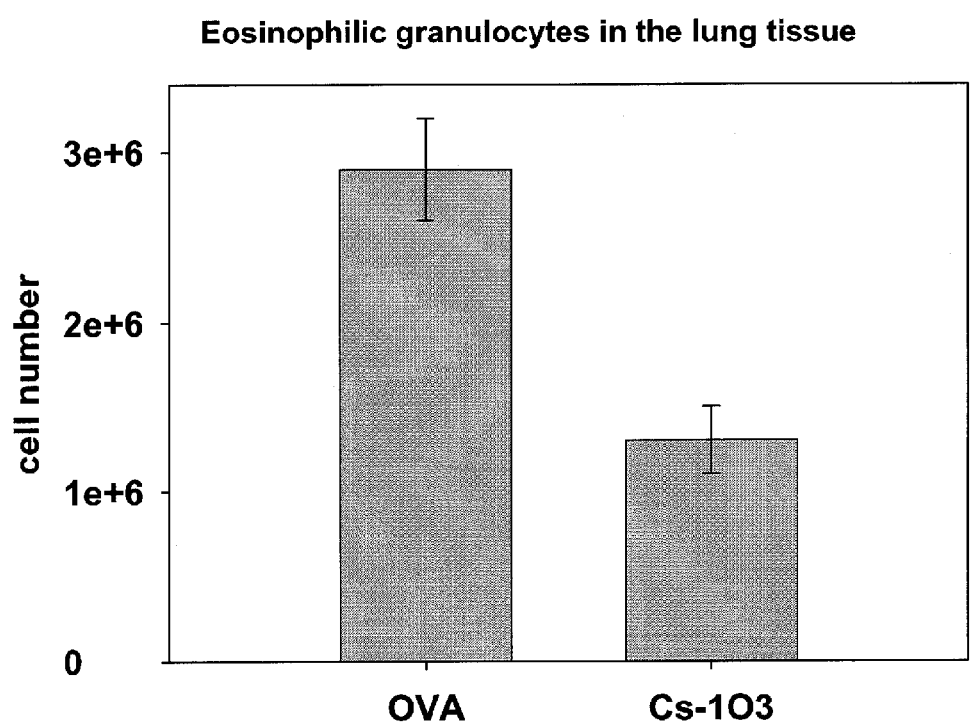
FIG. 2 the influence of 250 µg Cs-103 on the number of eosinophilic granulocytes (eosinophiles) which migrated through ovalbumin sensitization into the bronchial lining.

FIG. 2 shows the influence of 250 µg Cs-103 on the number of eosinophilic granulocytes (eosinophiles) which migrated through ovalbumin sensitization into the bronchial lining. The animals sensitized with OVA served as control. It can be seen from FIG. 1 that the administration of Cs-103 very significantly reduced the number of eosinophilic granulocytes.

Figure 3:
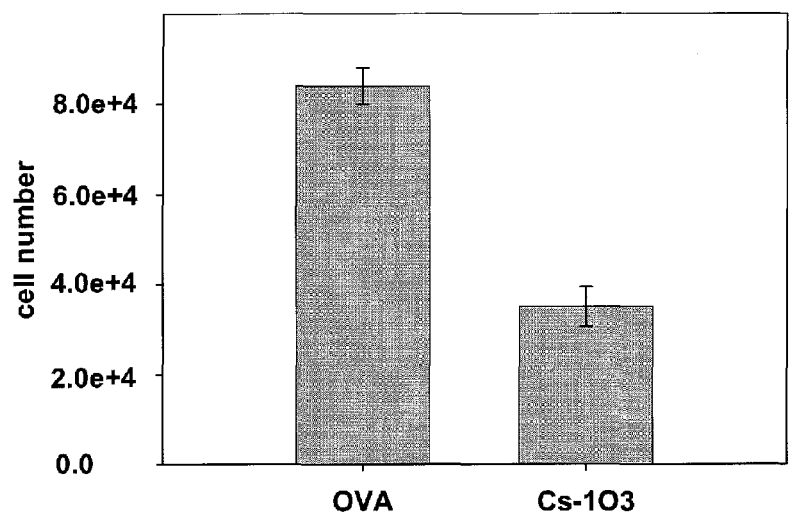
FIG. 3 the influence of 250 µg Cs-103 on the number of eosinophilic granulocytes (eosinophiles) which migrated through ovalbumin sensitization into the bronchial lining and can be detected in the lung lavage fluid.

As a control check, the number of eosinophilic granulocytes in the lung lavage fluid was determined (cf. FIG. 3). As can be seen from FIG. 3, here too the administration of 250 µg Cs-103 very significantly reduced the number of eosinophilic granulocytes.

b) Toxicity Test

Figure 4:
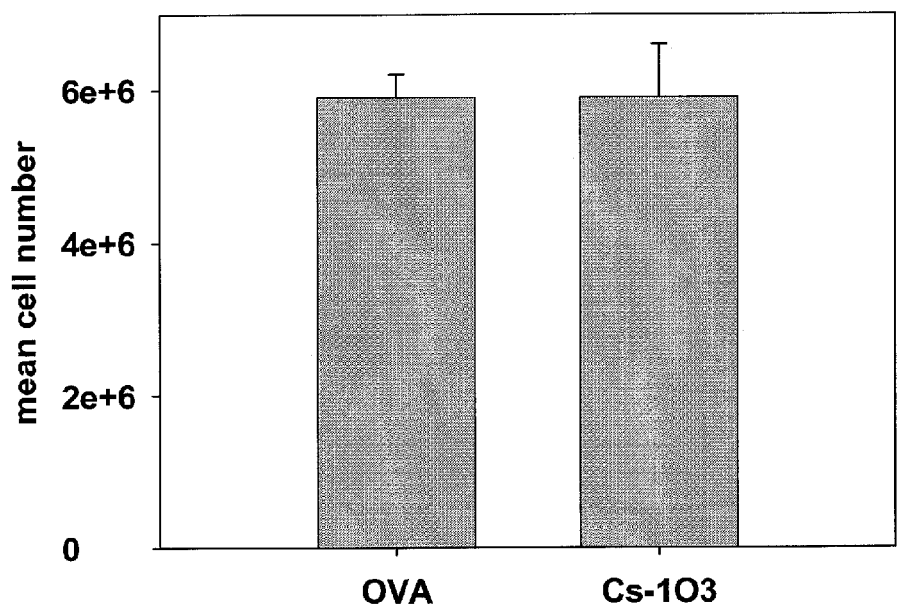
FIG. 4 the number of leukocytes in the blood before and after administering three doses ($1^{st}$, $3^{rd}$ and $5^{th}$ day) of 250 µg Cs-103 to each animal (determination on the $6^{th}$ day)
Figure 5:
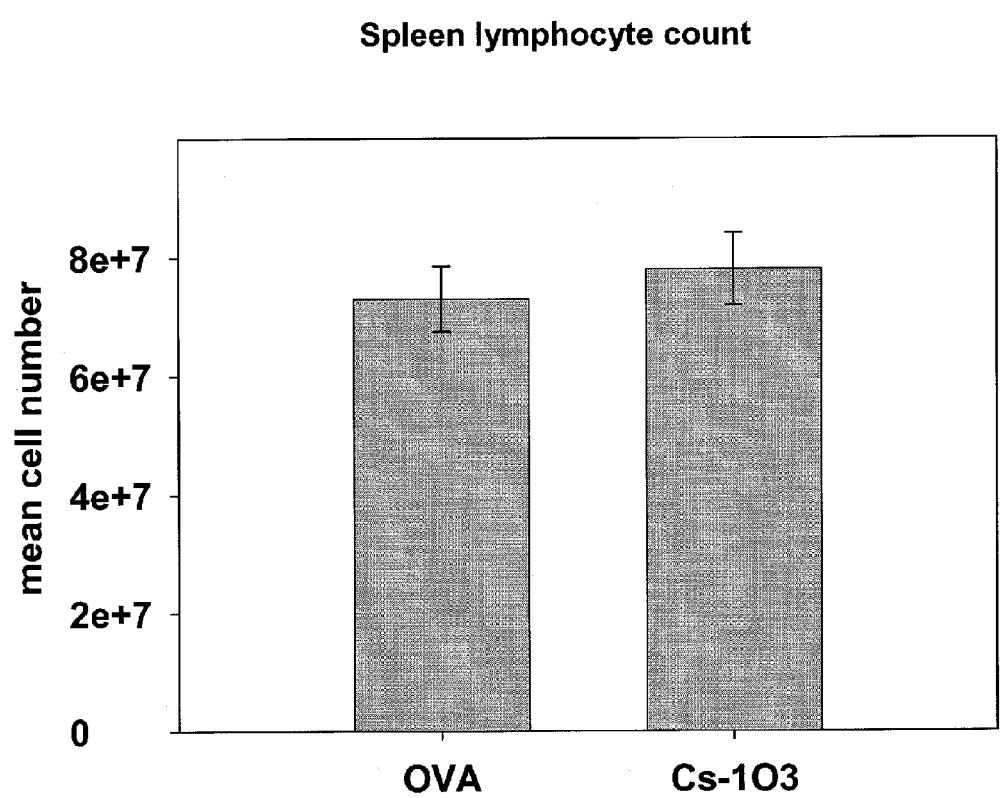
FIG. 5 the number of leukocytes in the spleen before and after administering three doses ($1^{st}$, $3^{rd}$ and $5^{th}$ day) of 250 µg Cs-103 to each animal (determination on the 6th day).

As the leukocyte count in blood and spleen increases in the case of inflammatory diseases, the number of these cells was used as toxicity marker. As FIGS. 4 and 5 show, the selected compound Cs-103 (after administering three doses of 250 µg Cs-103, on the $1^{st}$, $3^{rd}$ and $5^{th}$ day, and cell count determination on the $6^{th}$ day) is harmless in this assay.

It is understood that the foregoing description is that of the preferred embodiments of the invention and that various changes and modifications may be made thereto without departing from the spirit and scope of the invention as defined in the appended claims.

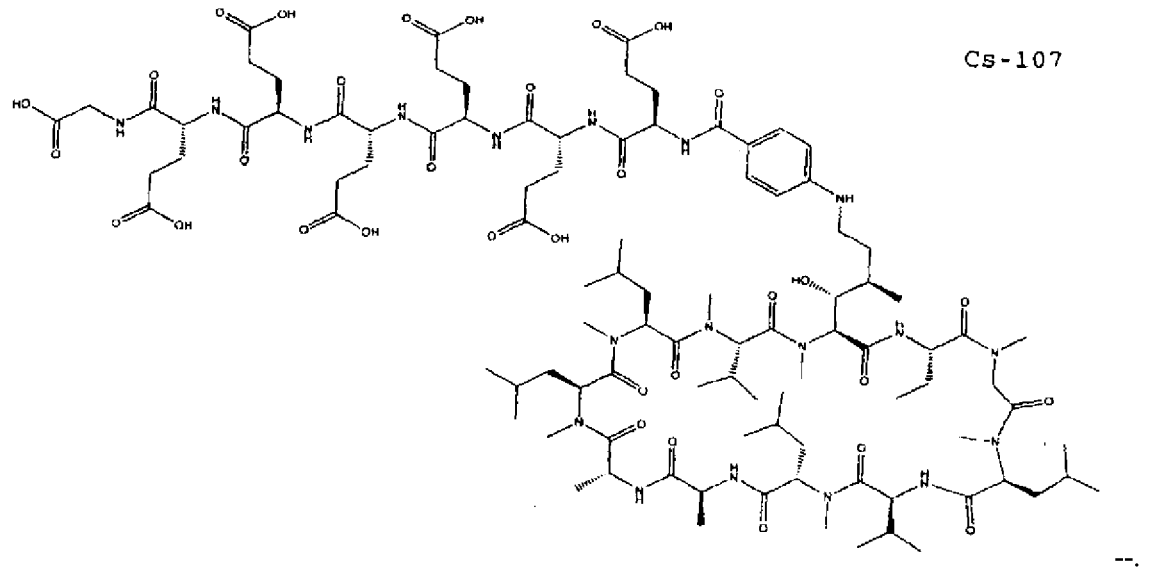

What is claimed is:
1. A cyclosporin derivative of general Formula I

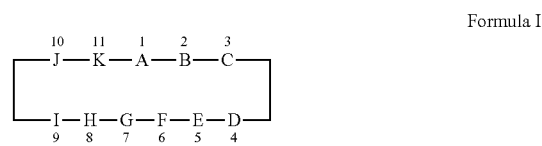

Formula I or a pharmaceutically acceptable salt thereof, wherein in Formula I
A is an amino acid residue of Formula II,

Formula II in which $R_1$ corresponds to a residue of Formula III

Formula III which is covalently bonded via the carbon atom a, or in which $R_1$ corresponds to a residue of Formula V

Formula V which is covalently bonded via the carbon atom a, or in which $R_1$ corresponds to a residue of Formula VIII

Formula VIII which is covalently bonded via the carbon atom a, wherein the C=O group in Formula II is covalently bonded to an alpha-amino group of B via an amide bond and the N—R$_o$ group in Formula II is covalently bonded to a carboxyl group of K via an amide bond, B is an amino acid residue which is selected from the group consisting of:

alpha-aminobutyric acid,
alanine,
threonine,
valine,
norvaline and
alpha-aminobutyric acid, alanine, threonine, valine or norvaline modified in the side chain with a hydroxyl group, C is a sarcosine residue, D is an amino acid residue which is selected from the group consisting of:

leucine,
N-methyl leucine,
valine,
gamma-hydroxy-N-methyl leucine and
gamma-hydroxy leucine, E is an amino acid residue which is selected from the group consisting of:

valine,
norvaline and
a modified valine or norvaline in which a carbon atom in the side chain is substituted by a hydroxyl group, F is an amino acid residue which is selected from the group consisting of:

leucine,
N-methyl leucine,
gamma-hydroxy-N-methyl leucine and
gamma-hydroxy leucine, G is an alpha-aminobutyric acid residue or an alanine residue, H is a D-alanine residue, I and J are residues which are selected, independently of one another, from the group consisting of:

leucine,
N-methyl leucine,
gamma-hydroxy-N-methyl leucine and
gamma-hydroxy leucine, and K is an N-methyl valine residue or a valine residue, wherein in Formulae III, V and VIII R$_o$ represents H or CH$_3$, X represents H or
hydroxyl or
a hydroxyl group which is derivatized with an alkanoyl, aryloyl, alkylaminocarbonyl, arylaminocarbonyl, arylalkylaminocarbonyl, alkoxycarbonyl, aryloxycarbonyl, arylalkyloxycarbonyl group or a silyl protecting group, R$_2$ represents
a substituted or unsubstituted monocyclic, bicyclic or tricyclic aryl or heteroaryl ring which is optionally substituted with R$_3$, R$_3$ is selected from the group consisting of:
—Z—CO—Y, and
—CO—Y, R$_4$ represents H or
a substituted or unsubstituted monocyclic, bicyclic or tricyclic aryl or heteroaryl ring which is optionally substituted with R$_3$, Z is selected from the group consisting of:

an unbranched, branched or cyclic alkyl group with 1 to 20 carbon atoms, an unbranched, branched or cyclic alkenyl group with 1 to 20 carbon atoms, and an unbranched, branched or cyclic alkinyl group with 1 to 20 carbon atoms, Y is selected from the group consisting of:

the protected or unprotected amino acid residues Gly, D-Glu, D-Asp, D- and L-Cys(SO$_3$H), and unprotected peptide residues with a chain length of from 2 to 200 amino acid residues, containing one amino acid type or a combination of different amino acid types selected from Gly, D-Glu, D-Asp, D- and L-Cys (SO$_3$H), R$_5$ is selected from the group consisting of:

an alkyl, alkenyl, alkylaminocarbonyl, alkylcarbonyl, alkoxycarbonyl group, the amino acid residues Gly, D-Glu, D-Asp, D- and L-Cys(SO$_3$H), peptide residues with a chain length of from 2 to 200 amino acid residues, containing one amino acid type or a combination of different amino acid types selected from Gly, D-Glu, D-Asp, D- and L-Cys (SO$_3$H), F, Cl, Br and I,
and R$_7$ is selected from the group consisting of:

a carboxyl, amino, thiol, hydroxyl group,

F, Cl, Br, I the protected or unprotected amino acid residues Gly, D-Glu, D-Asp, D- and L-Cys(SO$_3$H), and peptide residues with a chain length of from 2 to 200 amino acid residues, containing one amino acid type or a combination of different amino acid types selected from Gly, D-Glu, D-Asp, D- and L-Cys(SO$_3$H);

wherein the cyclosporin derivative has a negative net charge at pH 6.

2. The cyclosporin derivative according to claim 1, wherein the cyclosporin derivative is selected from the group consisting of Cs-101
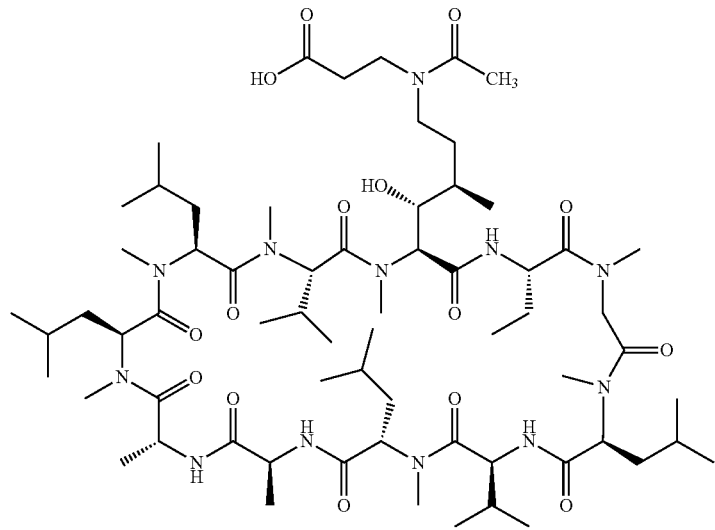
Cs-109
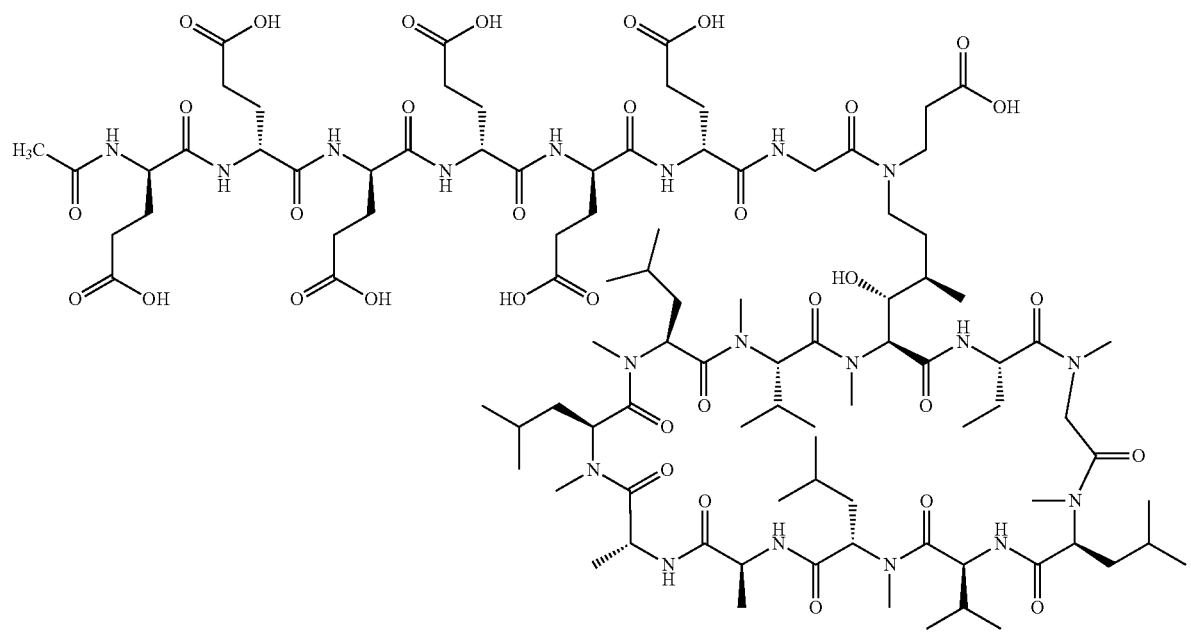
and -continued
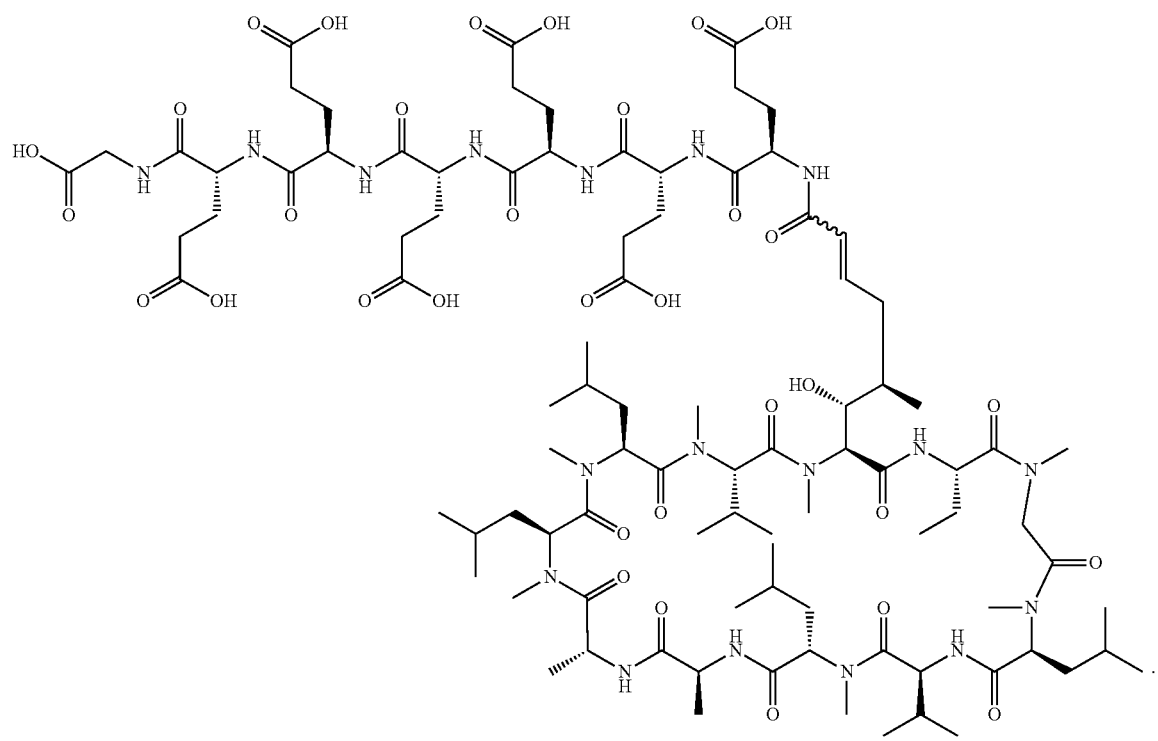
CsM5
3. A cyclosporin derivative selected from the group consisting of:
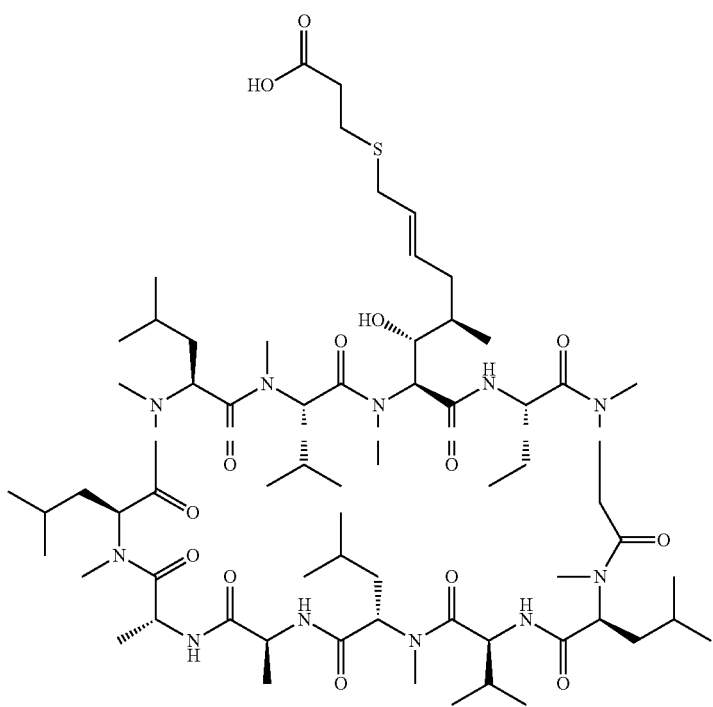
Cs-1WZ2

-continued
CS1A02
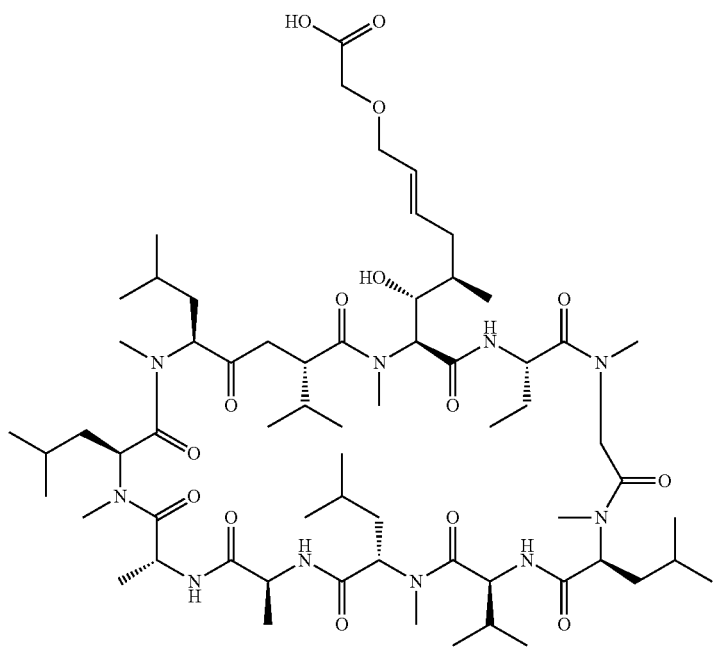
Cs-106
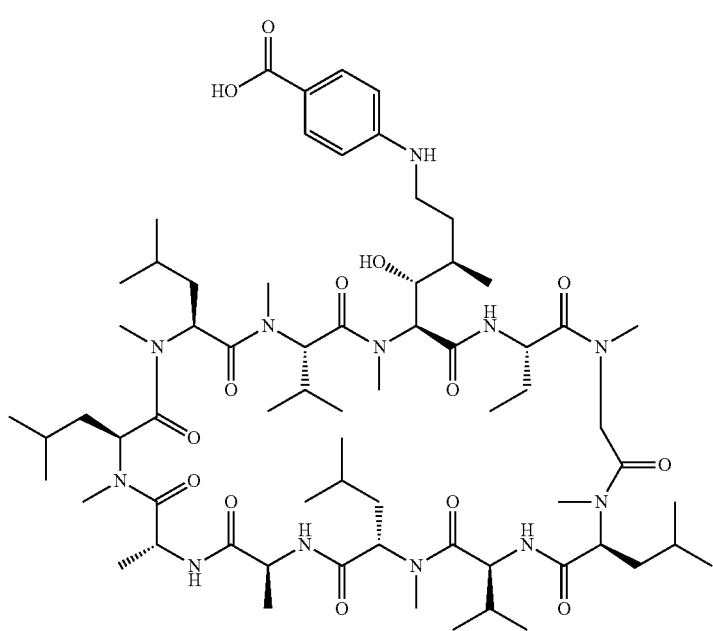

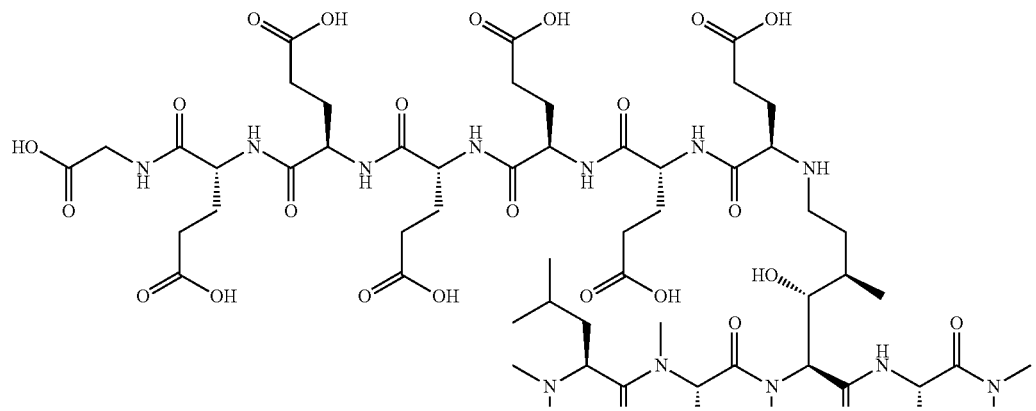
Cs-1011
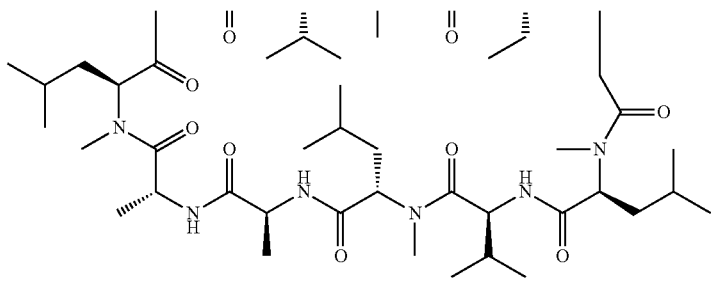
Cs-1H2
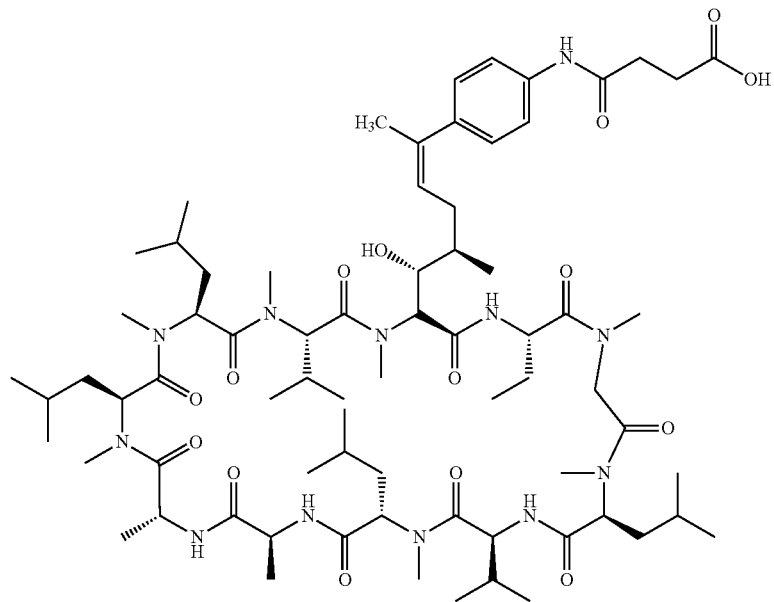
Cs-1H2-2
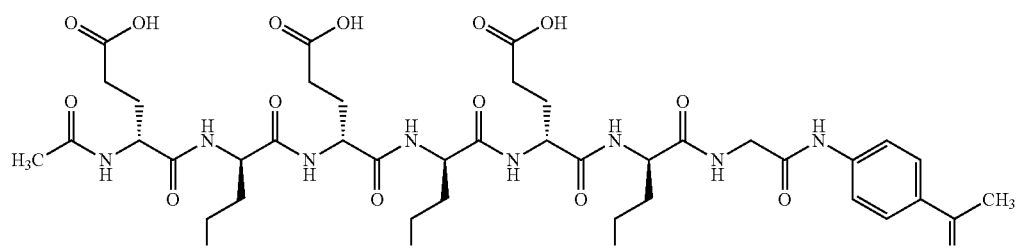

-continued
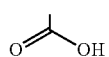
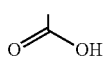
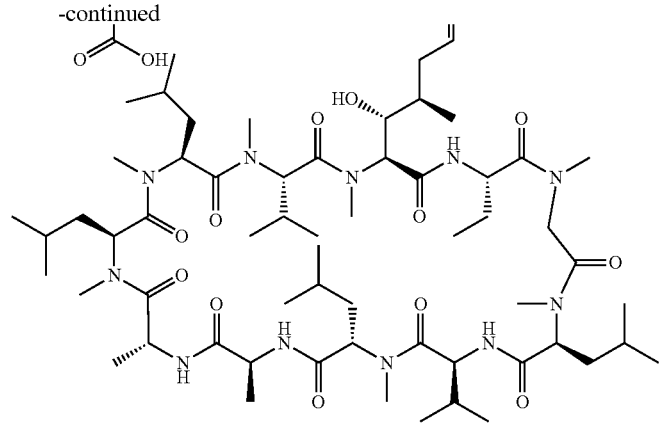
Cs-1WZ3
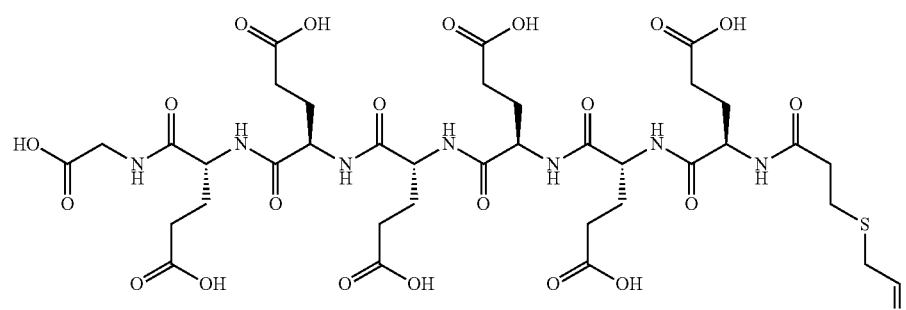
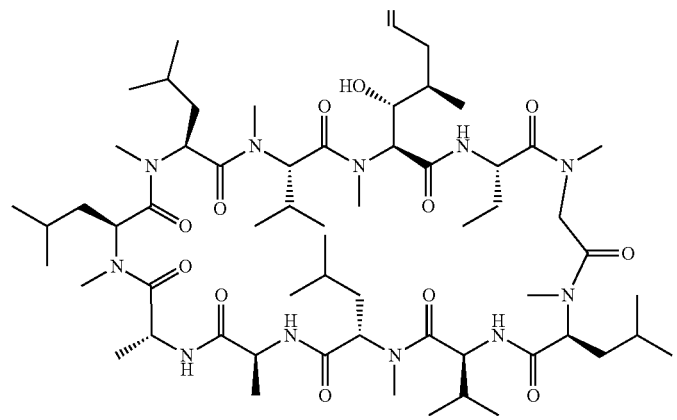
Cs-1A03
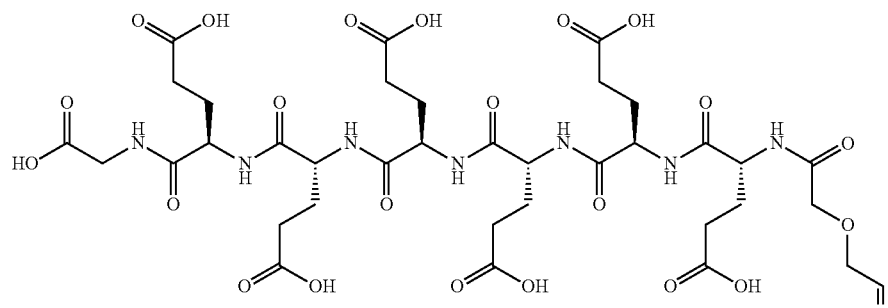

-continued
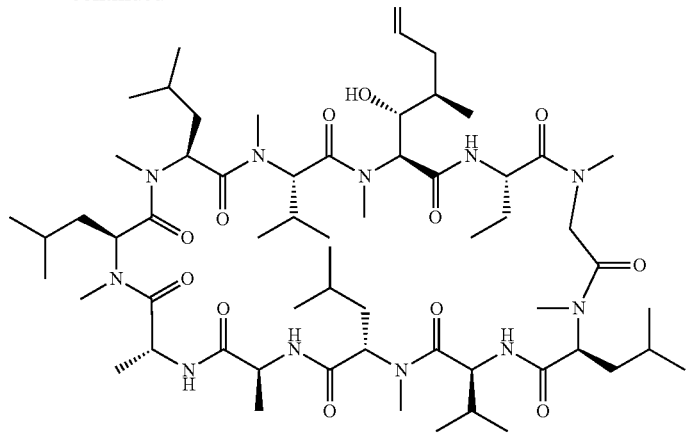
Cs-103
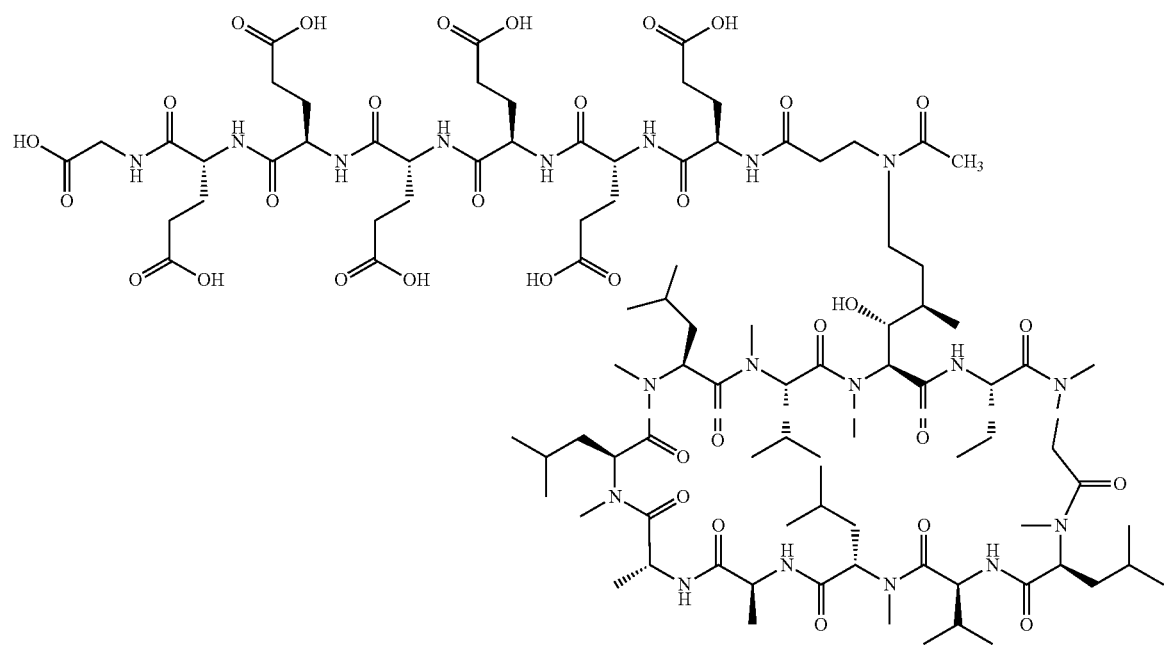
and
Cs-107
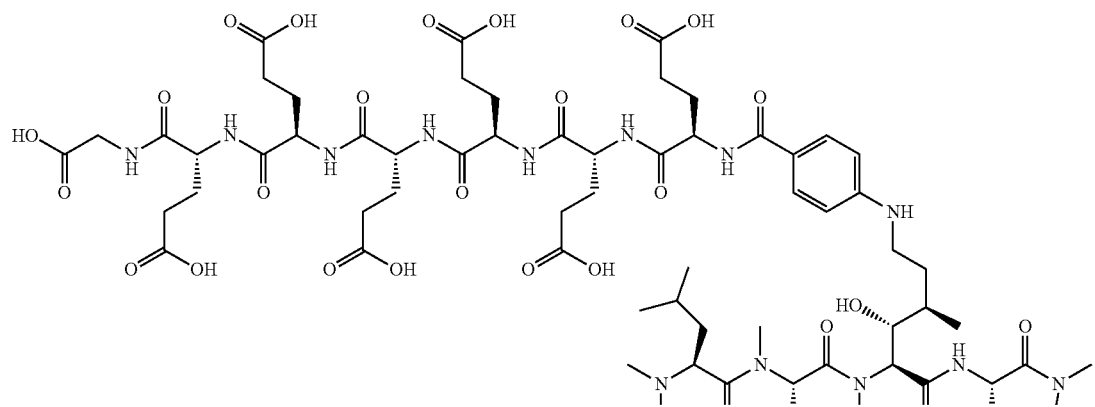

-continued

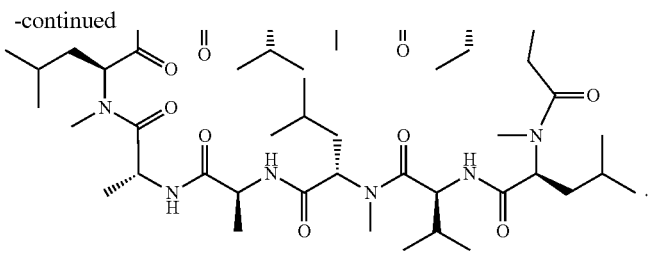

4. A method for concentrating a cyclosporin derivative in an extracellular space of a multicellular object, comprising the steps of:
   providing the cyclosporin derivative of claim 1; and
   bringing the cyclosporin derivative into contact with a multicellular object;
   wherein the multicellular object is a separated organ or body part, blood or a blood fraction, a cell culture or a plant.

5. A medicament comprising the cyclosporin derivative according to claim 1.

6. A method of treatment of a chronic inflammatory disease comprising administering the cyclosporin derivative according to claim 1 to a subject in need thereof.

7. The method according to claim 6, wherein the chronic inflammatory disease is selected from the group consisting of asthma, rheumatoid arthritis, multiple sclerosis, psoriasis and ulcerative colitis.

8. A pharmaceutical composition, comprising the cyclosporin derivative according to claim 1.

* * * * *

UNITED STATES PATENT AND TRADEMARK OFFICE
CERTIFICATE OF CORRECTION

PATENT NO. : 8,618,065 B2
APPLICATION NO. : 13/397256
DATED : December 31, 2013
INVENTOR(S) : G. Fischer et al.

Page 1 of 4

It is certified that error appears in the above-identified patent and that said Letters Patent is hereby corrected as shown below:

On the Title page, under References Cited, FOREIGN PATENT DOCUMENTS, item (56), line 4, please delete "JP   AU-2006200519" and insert -- AU   AU-2006200519 -- therefore.

On Title page 3, left column, line 5 from the bottom, under References Cited, OTHER PUBLICATIONS, item (56), please delete "Cyclosporines" and insert -- Cyclosporins -- therefore.

In the Specification,

At col. 11, please delete the lower chemical structure labeled Cs-1H1 and insert the following chemical structure therefore:

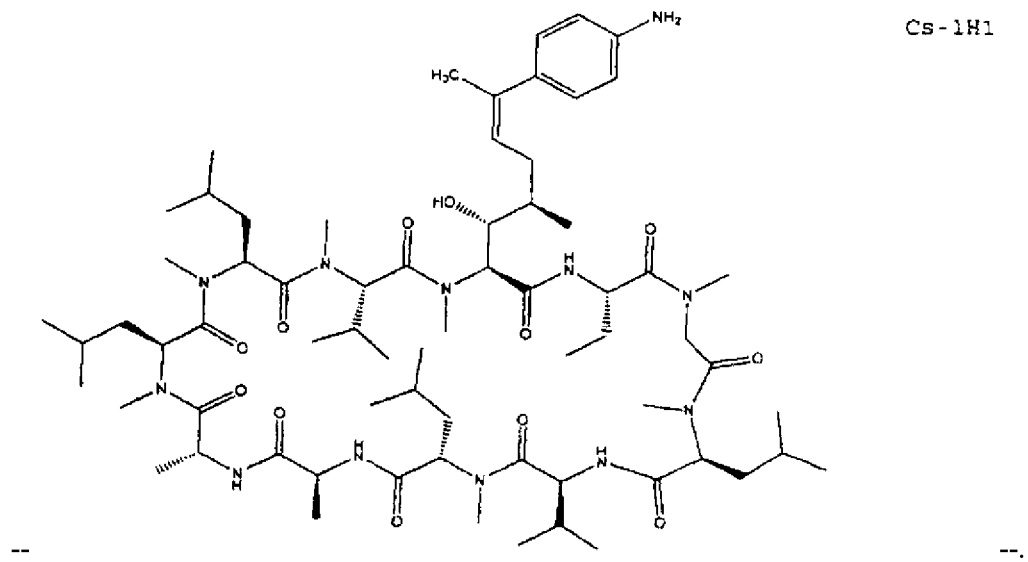

--                                                                              --.

At col. 15, please delete the chemical structure labeled Cs-1011.

At col. 23, please delete the chemical structure labeled Cs-1H2-2.

Signed and Sealed this
Eighteenth Day of November, 2014

Michelle K. Lee
*Deputy Director of the United States Patent and Trademark Office*

CERTIFICATE OF CORRECTION (continued)

At col. 30, please delete the un-labeled chemical structure.

At col. 35, please delete the chemical structure labeled Cs-107.

At col. 41, please delete the chemical structure labeled Cs-3E2.

At col. 43, please add the label -- CS-1E2 -- to the chemical structure.

At col. 51, line 15, delete "LION" and insert -- LiOH -- therefore.

At col. 61, please delete the upper chemical structure labeled Cs-109.

At cols. 65 to 66, please delete the chemical structure labeled Cs-103 at the bottom of the columns.

At cols. 69 to 70, please delete the chemical structure labeled Cs-1E2 at the top of the columns.

At cols. 71 to 72, please delete the chemical structure labeled Cs-1Ad2 at the bottom of the columns.

At col. 77, line 24, please delete "(BALE/c line)" and insert -- (BALB/c line) -- therefore.

At col. 77, line 41, please delete "CDC" and insert -- $CD4^+$ -- therefore.

At cols. 87 to 88, please delete the chemical structure fragments labeled Cs-1011 at the top of the columns and insert the following chemical structure therefore:

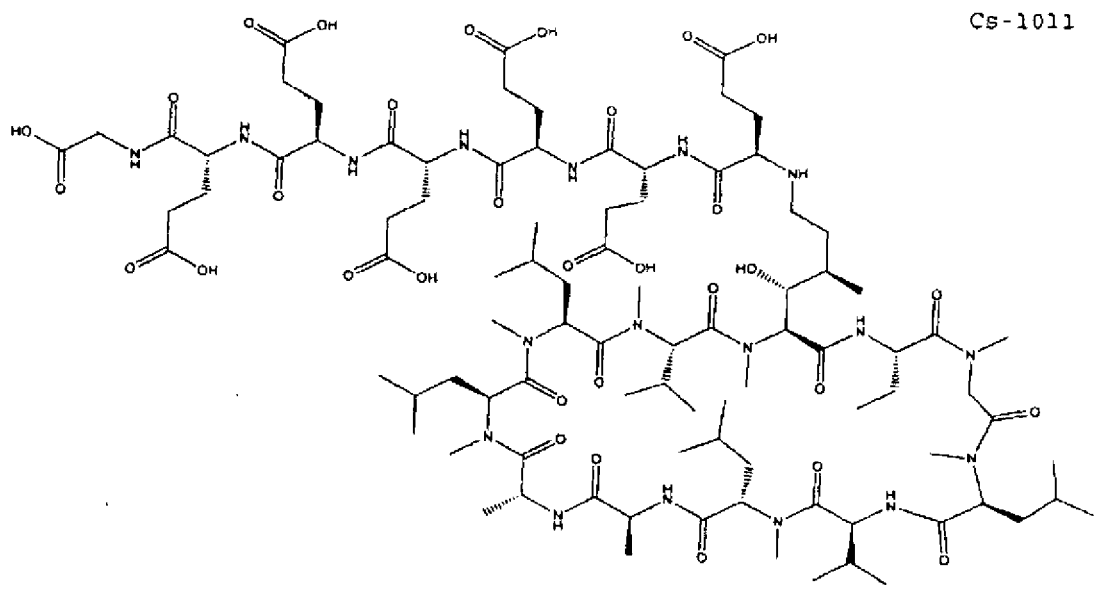

-- --.

CERTIFICATE OF CORRECTION (continued)
U.S. Pat. No. 8,618,065 B2

At cols. 87 to 88, please delete the chemical structure fragments labeled Cs-1H2-2 at the bottom of the columns.

At cols. 89 to 90, please delete the un-labeled chemical structure fragments at the top of the columns and insert the following chemical structure therefore:

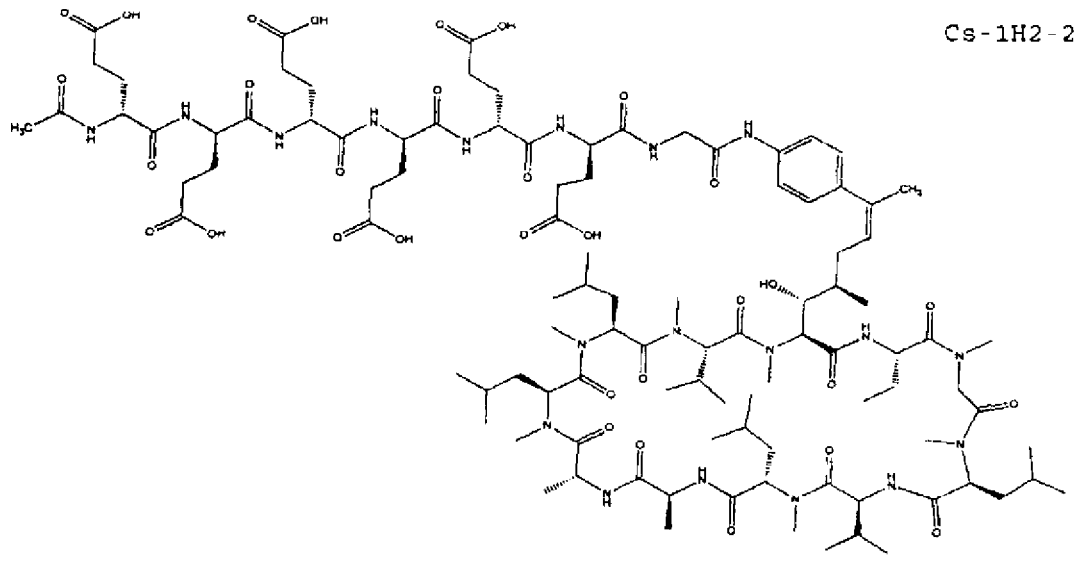

--                                                                                  --.

At cols. 89 to 90, please delete the chemical structure fragments labeled Cs-1WZ3 in the middle of the columns and insert the following chemical structure therefore:

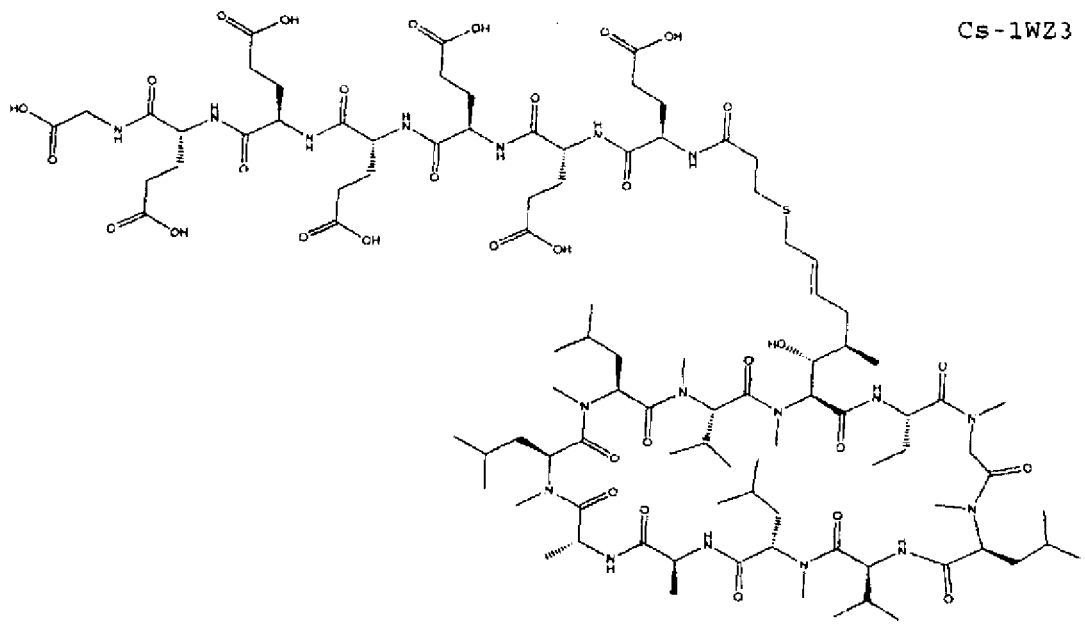

--                                                                                  --.

At cols. 89 to 90, please delete the chemical structure fragments labeled Cs-1A03 at the bottom of the columns.

At col. 92, please delete the chemical structure fragment at the top of the column and insert

CERTIFICATE OF CORRECTION (continued)
U.S. Pat. No. 8,618,065 B2 the following chemical structure therefore:

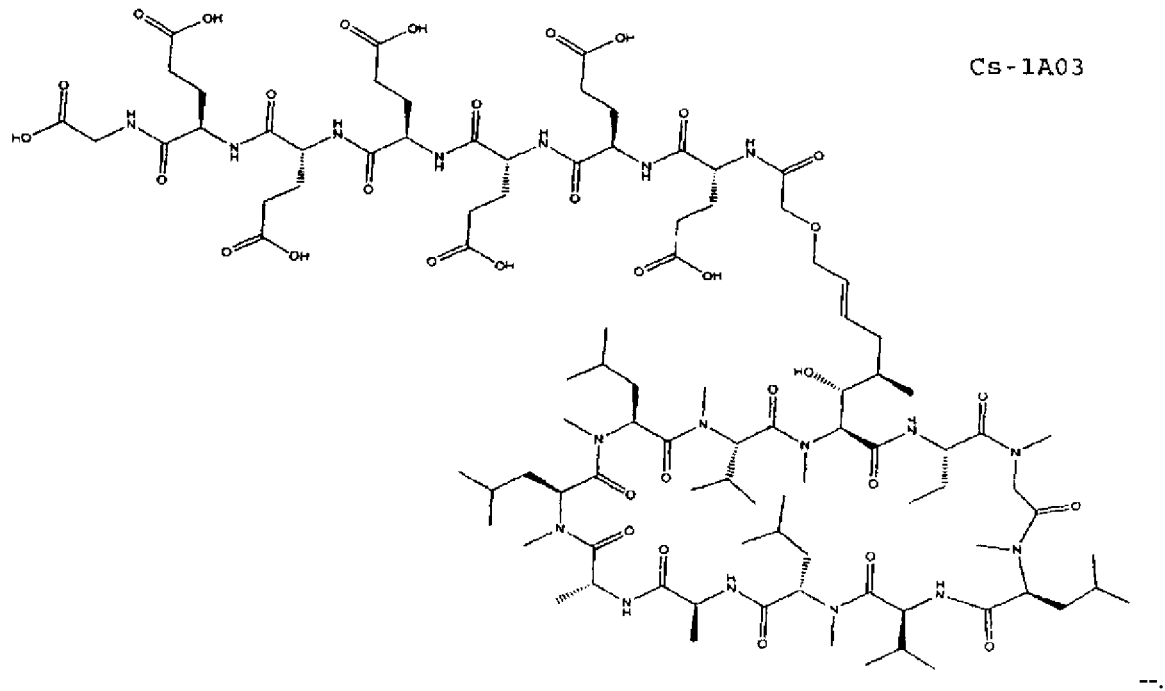

At cols. 91 to 92, please delete the chemical structure fragment labeled Cs-107 at the bottom of the columns.

At col. 94, please delete the chemical structure fragment at the top of the column and insert the following chemical structure therefore: